(12) United States Patent
Townsend et al.

(10) Patent No.: US 6,342,501 B1
(45) Date of Patent: Jan. 29, 2002

(54) PYRROLO[2,3-D] PYRIMIDINES AS ANTIVIRAL AGENTS

(75) Inventors: Leroy B. Townsend; John C. Drach, both of Ann Arbor, MI (US)

(73) Assignee: The Regents of the University of Michigan, Ann Arbor, MI (US)

(*) Notice: Subject to any disclaimer, the term of this patent is extended or adjusted under 35 U.S.C. 154(b) by 0 days.

(21) Appl. No.: 09/229,391

(22) Filed: Jan. 11, 1999

Related U.S. Application Data

(63) Continuation-in-part of application No. 08/690,472, filed on Jul. 26, 1996, now abandoned, which is a continuation of application No. 08/357,762, filed on Dec. 15, 1994, now Pat. No. 5,543,413, which is a continuation of application No. 08/201,695, filed on Feb. 25, 1994, now abandoned.

(51) Int. Cl.$^7$ ...................... C07D 487/04; A61K 31/52; A61P 31/22

(52) U.S. Cl. ...................... 514/258; 544/280

(58) Field of Search ........................... 514/258; 544/280

(56) References Cited

U.S. PATENT DOCUMENTS

| | | |
|---|---|---|
| 4,680,176 A | 7/1987 | Berns et al. |
| 4,709,011 A | 11/1987 | Cohen et al. |
| 4,892,865 A | 1/1990 | Townsend et al. |
| 4,927,830 A | 5/1990 | Townsend et al. |
| 4,968,686 A | 11/1990 | Townsend et al. |
| 5,399,580 A | 3/1995 | Daluge |
| 5,543,413 A | 8/1996 | Townsend et al. |
| 5,679,342 A | 10/1997 | Houghton et al. |

FOREIGN PATENT DOCUMENTS

| | | |
|---|---|---|
| WO | WO 94/13676 | 6/1994 |
| WO | WO 95/23151 | 8/1995 |

OTHER PUBLICATIONS

"Fields Virology, Third Ed.", B. N. Fields et al Eds., Lippincott–Raven, Philadelphia, ,p. 18, 431, 2228.*
"The Condensed Chemical Dictionary", 9th Ed., Gessner G. Hawley Ed., Van Nostrand, New York, p 25.*
"Webster's New World Dictionary, College Ed." no author listed, World Publishing, 1962, p. 396.*
"Fields Virology, Third Ed.", B. N. Fields et al eds., Lippincott–Raven, Philadelphia, 1996, p. 431.*
Thomas E. Renau et al., "Synthesis of Non–nucleoside Analogs of Toyocamycin, Sangivamycin, and Thiosangivamycin: Influence of Various 7–Substituents on Antiviral Activity" *J. Med.Chem.* 39:873–880 (1996).
Thomas E. Renau et al., "Synthesis of Non–nucleoside Analogs of Toyocaymcin, Sangivamycin, and Thiosangivamycin: The Effect of Certain 4– and 4.6 substituents on the Antiviral Activity of Pyrrolo[2,3–d]pyrimidines" *J. Med. Chem.* 39:3470–3476 (1996).

Sharon M. Bennett et al., "Synthesis and Antiviral Activity of Some Acyclic and C–Acylic Pyrrolo[2,3–d]pyrimidine Nucleoside Analogues" *J. Med. Chem.* 33:2162–2173 (1990).
Ahmed, R. et al., "Viral Persistance" in: Fundamental Virology, 2nd Ed., Fields et al. (Eds.), Raven Press, New York, pp. 241–265 (1991).
Alford, C. A. et al., "Congenital and Perinatal Cytomegalovirus Infections"*Rev. Infect. Dis.* 12(Suppl. 7):S745–S753 (1990).
Alford, C. A. et al., "Cytomegalovirus" in: The Human Herpesviruses, Roizman et al. (Eds.), Raven Press, New York, pp. 227–255 (1993).
"Antiviral Drugs" in: Drug Evaluations Annual 1993 (Chapter 76), American Medical Association, p. 1723 (1993).
Bergstrom, D. E. et al., "Antiviral activity of C–5 substituted tubercidin analogues" *J. Med. Chem.* 27:285–292 (1984).
Biron, K. K. et al., "Metabolic activation of the nucleoside analog 9–[2–hydroxy–1–(hydroxymethyl)ethoxy]methyl guanine in human diploid fibroblasts infected with human cytomegalovirus" *PNAS USA* 82:2473–2477 (1985).

(List continued on next page.)

*Primary Examiner*—Mukund J. Shah
*Assistant Examiner*—Thomas C McKenzie
(74) *Attorney, Agent, or Firm*—Antoinette F. Konski; McCutchen, Doyle, Brown & Enersen, LLP

(57) ABSTRACT

This invention relates to a novel class of 4,5,6,7-substituted non-nucleoside, non-phosphorylatable pyrrolo[2,3-d] pyrimidines which exhibit both significantly lower levels of cytotoxicity and superior antiviral activity than known nucleoside, non-nucleoside, and non-nucleoside, non-phosphorylatable pyrrolo[2,3-d]pyrimidine derivatives, particularly against human DNA viruses such as cytomegalovirus (HCMV) and herpes simplex virus type 1 (HSV-1). These compounds are represented by the following formula:

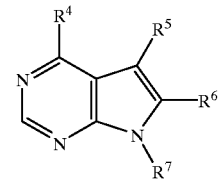

wherein: $R^4$ is $-NR_1R_2$ or oxo; $R^5$ is $-CN$, or $-CSNR_1R_2$, or $-CONR_1R_2$; $R^6$ is $-H$, or halo, or $-NR_1R_2$; wherein $R_1$ and $R_2$ are independently $-H$ or an aliphatic group; and $R^7$ is of the formula $R_3-Ar$, wherein $R_3$ is an aliphatic group and Ar is an unsubstituted aryl or an aryl independently substituted with halo, nitro, amino, or aliphatic groups; provided that when $R^5$ is a $-CN$ or $-CSNH_2$, and $R^6$ is a $-H$ or $-NH_2$, and Ar is a $-C_6H_5$ or a phenyl substituted with only one aliphatic group, $R_3$ is an aliphatic group other than methyl such that $-R_3-$ is not a $-CH_2-$; and pharmaceutically acceptable salts, prodrugs and derivatives thereof.

51 Claims, No Drawings

OTHER PUBLICATIONS

Chrisp, P. et al., "Foscarnet. A review of its antiviral activity, pharmacokinetic properties and therapeutic use in immuno-compromised patients with cytomegalovirus retinitis" *Drugs* 41:104–129 (1991).

Collins, P. et al., "Relative potencies of anti–herpes compounds" *Ann. N.Y. Acad. Sci.* 284:49–59 (1977).

Crumpacker, C. S., "Ganciclovir" *New England J. Med.* 335:721–729 (1996).

Declerq, E. et al., "Antirhinovirus activity of purine nucleosid analogs" *Antimicrob. Agents Chemother.* 29:482–487 (1986).

Drach, J. C. et al., "The selective inhibition of viral DNA synthesis by chemotherapeutic agents: An indicator of clinical usefulness" *Ann. N.Y. Acad. Sci.* 284:396–409 (1997).

Field, A. K. et al., "The end of innocence revisited: Resistance of herpesvirus to antiviral drugs" *Clin. Microbiol. Rev.* 7:1–13 (1994).

Gallant, J. E. et al., "Incidence and natural history of cytomegalovirus disease in patients with advanced immunodeficiency virus disease treated with zidovudine" *J. Infect. Dis.* 166:1223–1227 (1992).

Gibbs, E. P. J. et al., "Bovine herpesviruses. Part I: Bovine herpesvirus 1" *Vet. Bull.* 47:317–343 (1997).

Goldstein, A., "Analysis of a single curve with graded responses" in: Biostatistics: An Introductory Text, Mac-Millan Co., New York, pp. 156–161 (1964).

Gupta, P. K. et al., "Synthesis, cytotoxicity, and antiviral activity of some acyclic analogues of the pyrrolo[2,3–*d*] pyrimidine nucleoside antibiotics tubercidin, toyocamycin, and sangivamycin" *J. Med. Chem.* 32:402–408 (1989).

Hermann, Jr., E. C., "The detection, assay and evaluation of antiviral drugs" *Prog. Med. Virol.* 3:158–192 (1961).

Hirsch, M. S. et al., "Antiviral therapy" *Scientific American*:76–85 (Apr. 1987).

Hitchcock, M. J. et al., "Cidofovir, a new agent with potent anti–herpesvirus activity" *Antiviral Chem. & Chemother.* 7:115–127 (1996).

Hsiung, G. D. et al., "Evaluation of new antiviral agents: II. The use of animal models" *Antiviral Res.* 12:239–258 (1989).

Hu, J. M. et al., "Evaluation of new antiviral agents: I. In vitro perspectives" *Antiviral. Res.* 11:217–232(1989).

Kim, D. W. et al., "C–terminal domain of the hepatitis C virus NS3 protein contains an RNA helicase activity" *Biochem. Biophys. Res. Comm.* 215:160–166 (1995).

Kucera, L. S. et al., "Activity of triciribine and triciribine–5–monophosphate against human immunodeficiency virus types 1 and 2" *AIDS Res. Human Retroviruses* 9:307–314 (1993).

Lain, S. et al., "RNA helicase: A novel activity associated with a protein encoded by a positive strand RNA virus" *Nucl. Acids Res.* 18:7003–7006 (1990).

Lalezari, J. P. et al., "(S)–1–[3–hydroxy–2–(phosphonylmethoxy)propyl ]cytosine (cidofovir): results of a phase I/II study of a novel antiviral nucleotide analogue" *J. Infect. Dis.* 171:788–796 (1995).

Murphy, F. A. et al., "Virus taxonomy"in: Fundamental Virology, 2nd Ed., Fields et al. (Eds.), Raven Press, New York, pp. 9–36 (1991).

Prichard, M. N. et al., "A microtiter virus yield reduction assay for the evaluation of antiviral compounds against human cytomegalovirus and herpes simplex virus" *J. Virol. Meth.* 28:101–106 (1990).

Prichard, M. N. et al., "A three dimensional model to analyze drug–drug interactions" *Antiviral Res.* 14:181–206 (1990).

Prichard, M. N. et al., "Three–dimensional analysis of the synergistic cytotoxicity of ganciclovir and zidovudine" *Antimicrob. Agents & Chemother.* 35:1060–1065 (1991).

Renau, T. E. et al., "Design, synthesis and activity against human cytomeglovirus of non–phosphorlatable analogs of toyocamycin, sangivamycin and thiosangivamycin" *Bioor. & Med. Chem. Lett.* 2:1755–1760 (1992).

Renau, T. E. et al., "Improved synthesis and biological evaluation of an acyclic thiosangivamycin active against human cytomegalovirus" *Antiviral Res.* 19:15–28 (1992).

Renau, T. E. et al., "Relationship between cytotoxicity and conversion of thiosangivamycin analogs to toyocamycin ananlogs in cell culture medium" *Biochem. Pharmacol* 48:801–807. (1994).

Renau, T. E. et al., "Antiherpetic activity, cytotoxicity and metabolism of non–nucleoside analogs related to toyocamycin, sangivamycin and thiosangivamycin" Sixth International Conference on Antiviral Research, Venice, Italy, 25–30 Apr. 1993, *Antiviral Res.*, vol. 20, Suppl. 1 (1993), p. 118 (Abstract No. 138).

Renau, T. E. et al., "Spontaneous oxidation of thiosangivamycin analogs by cell culture medium ameliorates cytotoxicity" 206th National American Chemical Society Meeting, Chicago, IL, 22–27 Aug. 1993, *Abstr. Pap. Am. Chem. Soc.* 206(1–2) MEDI (1993), (Abstract No. 133).

Renau, T. E. et al., "Activity against human cytomegalovirus, cytotoxicity and mode of action fo a non–nucleoside pyrrolo 2,3–*d* pyrimidine" Seventh International Conference on Antiviral Research, Charleston, SC, Mar. 1994, *Antiviral Res.*, vol. 23, Suppl. 1 (1994), p. 91(Abstract No. 104).

Renau, T. E. et al., "Structure–activity relationships of non–nucleoside pyrrolopyrimidine analogs active against human cytomegalovirus" Seventh International Conference on Antiviral Research, Charleston, SC, Mar. 1994, *Antiviral Res.*, vol. 23, Suppl. 1(1994), p. 91(Abstract No. 105).

Roizman, B. et al., "Herpesvirus and their replication" *in*: Fundamental Virology (Chapter 29), Fields et al. (Eds.), Raven Press, New York, pp. 607–636 (1986).

Roizman, B. et al., "Herpes Simplex Viruses and Their Replication" *in*: Fundamental Virology, 2nd Ed., Fields et al. (Eds.), Raven Press, New York, pp. 849–895 (1991).

Saxena, N. K. et al., "Synthesis and antiviral activity of some 7–(2–hydroxyethoxy) methyl pyrazolo [3, 4–*d*] pyrimidine analogues of sangivamycin and toyocamycin" *J. Med. Chem.* 33:1980–1983 (1990).

Shipman, Jr., C. et al., "Evaluation of 4–2–hydroxyethyl)–1–pipraazineëthanesulfonic acids (HEPES) as a tissue culture buffer" *Proc. Soc. Exp. Biol.* 130:305–310 (1969).

Sidwell, R. W. et al., "Use of disposable micro tissue culture plates for antiviral and interferon induction studies" *Appl. Microbiol* 22:797–801 (1971).

Stinski, M. F., "Cytomegalovirus and its replication" *in*: Fundamental Virology, 2nd Ed., Fields et al. (Eds.), Raven Press, New York, pp. 929–950 (1991).

Swayze, E. E. et al., "The improved preparation of a versatile synthon for the synthesis of pyrrolo[2,3–*d* ] pyrimidines" *in*: Nucleic Acid Chemistry: Improved and New Synthetic Procedures, Methods and Techniques, Townsend, L. B. et al., (Eds.), Wiley–Interscience, New York, Part 1V, pp. 16–18 (1991).

Swayze, E. E. et al., "Synthesis, antiproliferative, and antiviral evaluation of certain acyclic 6–substituted pyrrolo[2, 3–*d* ]–pyrimidine nucleoside analogs related to sangivamycin and toyocamycin" *Nucleosides & Nucleotides* 11:1507–1527 (1992).

Turk, S. R. et al., "Pyrrolo [2,3–*d* ] pyrimidine nucleosides as inhibitors of human cytomegalovirus" *Antimicrob. Agents & Chemother.* 31:544–550 (1987).

Watson, J. D. et al., *in*: Molecular Biology of the Gene, Fourth Edition, Benjamin/Cummings Publ. Co., Menlo Park, CA, pp. 904,933 (1987).

White, E. L. et al., "A TIBO derivative, R82913, is a potent inhibitor of HIV–1 reverse trancriptase with heteropolymer templates" *Antiviral Res.* 16:257–266 (1991).

Wingard, J. R. et al., "Cytomegalovirus infections in bone marrow transplant recipients given intensive cytoreductive therapy" *Rev. Infect. Dis.* 12(Suppl. 7):S793–S804 (1990).

\* cited by examiner

PYRROLO[2,3-D] PYRIMIDINES AS ANTIVIRAL AGENTS

CROSS-REFERENCE TO RELATED APPLICATIONS

This application is a continuation-in-part of U.S. patent application Ser. No. 08/690,472, filed Jul. 26, 1997, now abandoned which is a continuation of U.S. patent application Ser. No. 08/357,762, filed Dec. 15, 1994, now U.S. Pat. No. 5,543,413, which is a continuation of U.S. patent application Ser. No. 08/201,695, filed Feb. 25, 1994, now abandoned, the contents of which are hereby incorporated by reference into the present disclosure.

STATEMENT OF RIGHTS TO INVENTIONS MADE UNDER FEDERALLY SPONSORED RESEARCH

This invention was made in part with Government support under contract number NO1-AI72641 awarded by the National Institute of Allergy and Infectious Diseases. The Government has certain rights in this invention.

TECHNICAL FIELD

The present invention relates to new non-phosphorylatable, non-nucleoside pyrrolo[2,3-d] pyrimidines and their use in the treatment of viral infections.

BACKGROUND OF THE INVENTION

Broad spectrum antiviral activity of pyrrolo[2,3-d] pyrimidine nucleosides such as tubercidin, sangivamycin and toyocamycin and some substituted derivatives previously has been reported. Activity of those compounds against specific viruses, such as RNA rhinovirus and DNA herpes simplex virus type 1 and type 2 also has been reported. See, for example, Bergstrom, D. E. et al., *J. Med. Chem.* 27:285–292 (1984); and DeClercq, E. et al., *Antimicrob. Agents Chemother.*, 29:482–487 (1986).

Pyrrolo[2,3-d]pyrimidine nucleosides are particularly attractive as potential antiviral agents because of their stability toward the action of two major enzymes of bioactive purine nucleoside inactivation, deamination by adenosine deaminase and glycosidic bond cleavage by purine nucleoside phosphorylases. Unfortunately, many of the pyrrolo[2,3-d]pyrimidine nucleosides which have been previously described as having potential antiviral activity also exhibit unacceptable levels of cytotoxicity, thereby diminishing their usefulness in treatment of viral infections.

A number of pyrrolo[2,3-d]pyrimidine nucleoside derivatives which exhibit improved antiviral activity and more acceptable levels of cytotoxicity than tubercidin, sangivamycin and thiosangivamycin have been reported. These prior art pyrrolo[2,3-d]pyrimidine nucleoside derivatives are described below.

Townsend et al. (U.S. Pat. No. 4,892,865) disclose the use of, inter alia, several 4-amino-pyrrolo[2,3-d]pyrimidine-5-carbonitriles and 4-aminopyrrolo[2,3-d]pyrimidine-5-thiocarboxamides substituted at the 7-position with 2',3'-dideoxy-2',3'-didehydro-β-D-ribofuranose and 2',3'-dideoxyribofuranose as antiviral agents.

Renau et al. (*Bioorg. & Med. Chem. Lett.*, 2:1755–1760, 1992) disclose the use of, inter alia, 4-amino-pyrrolo[2,3-d]pyrimidine -5-thiocarboxamides and 4-amino-pyrrolo[2,3-d]pyrimidine-5-carbonitriles substituted at the 7-position with β-D-ribofuranose as antiviral agents.

A number of pyrrolo[2,3-d]pyrimidine non-nucleoside derivatives which exhibit improved antiviral activity and more acceptable levels of cytotoxicity than tubercidin, sangivamycin, toyocamycin and thiosangivamycin as well as the nucleoside derivatives described above have been reported. These prior art pyrrolo[2,3-d]pyrimidine non-nucleoside derivatives are described below.

Townsend et al. (U.S. Pat. Nos. 4,927,830 and 4,968,686) disclose the use of, inter alia, several 4-amino-pyrrolo[2,3-d]pyrimidine-5-thiocarboxamides and 4,6-diamino-pyrrolo [2,3-d]pyrimidine-5-thiocarboxamides variously substituted at the 7-position with $-CH_2OCH(CH_2OH)_2$, $-CH_2OCH_2CH_2OH$ and $-CH(CH_2OH)(OCH(CH_2OH)_2)$ as antiviral agents.

Gupta et al. (*J. Med. Chem.*, 32: 402–408, 1989) disclose the use of, inter alia, several 4-amino-pyrrolo[2,3-d] pyrimidine-5-thiocarboxamides and 4-amino-pyrrolo[2,3-d] pyrimidine-5-carbonitriles variously substituted at the 7-position by $-CH_2OCH(CH_2OH)_2$ and $-CH(CH_2OH)(OCH(CH_2OH)_2)$ as antiviral agents.

Gupta et al. (J. Med. Chem., 32:1420–1425, 1989) disclose the use of, inter alia, several 4-amino.-pyrrolo[2,3-d] pyrimidine-5-thiocarboxamides and 4-amino-pyrrolo[2,3-d] pyrimidine-5-carbonitriles substituted at the 7-position by $-CH_2OCH_2CH_2OH$ as antiviral agents.

Renau et al. (*Antiviral Res.*, 19:15–28, 1992) disclose the use of 4-amino-pyrrolo[2,3-d]pyrimidine-5-thiocarboxamide and 4-aminopyrrolo[2,3-d]pyrimidine-5-carbonitrile substituted at the 7-position by $-CH_2-OCH_2-CH_2-OH$ as antiviral agents.

Swayze et al. (*Nucleosides and Nucleosides*, 11:1507–1527, 1992) disclose the use of, inter alia, 4,6-diamino-pyrrolo[2,3-d]pyrimidine -5-thiocarboxamides and 4,6-diamino-pyrrolo[2,3-d]pyrimidine-5carbonitriles variously substituted at the 7-position by $-CH_2-OCH_2-CH_2-OH$ and $-CH_2-OCH(CH_2-OH)_2$ as antiviral agents.

A limited number of pyrrolo[2,3-d]pyrimidine non-nucleoside, non-phosphorylatable derivatives which exhibit improved antiviral activity and more acceptable levels of cytotoxicity than tubercidin, sangivamycin, toyocamycin and thiosangivamycin as well as the nucleoside derivatives described above have been reported.

For example, Renau et al. (*Bioorg & Med Chem. Lett.*, 2:1755–1760, 1992) disclose the use of, inter alia, several 4-amino-pyrrolo[2,3-d]pyrimidine-5-thiocarboxamides and 4-amino-pyrrolo[2,3-d]pyrimidine-5-carbonitriles variously substituted at the 7-position with $-CH_2-OCH_2-CH_2-OH$, $-CH_2-OCH(CH_2-OH)_2$, $CH_3$, $-CH_2-CH=CH_2$, and $-CH_2-CH_2-CH_3$ as antiviral agents.

BRIEF DESCRIPTION OF THE INVENTION

One aspect of the present invention relates to a novel class of 4,5,6,7-substituted non-nucleoside, non-phosphorylatable pyrrolo[2,3-d]pyrimidines which exhibit both significantly lower levels of cytotoxicity and superior antiviral activity than known nucleoside, non-nucleoside, and non-nucleoside, non-phosphorylatable pyrrolo[2,3-d]pyrimidine derivatives, particularly against human DNA viruses such as cytomegalovirus (HCMV) and herpes simplex virus type 1 (HSV-1). Many of these compounds are represented by the following formula:

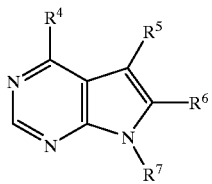

wherein:
R⁴ is —NR₁R₂ or oxo;
R⁵ is —CN, or —CSNR₁R₂, or —CONR₁R₂;
R⁶ is —H, or halo, or —NR₁R₂;
wherein R₁ and R₂ are independently —H or an aliphatic group; and R⁷ is of the formula —R₃Ar, wherein R₃ is an aliphatic group and Ar is an unsubstituted aryl or an aryl independently substituted with halo, nitro, amino, or aliphatic groups; provided that when R⁵ is a —CN or —CSNH₂, and R⁶ is a —H or —NH₂, and Ar is a —C₆H₅ or a phenyl substituted with only one aliphatic group, R₃ is an aliphatic group other than methyl such that —R₃— is not a —CH₂—; and pharmaceutically acceptable salts, prodrugs and derivatives thereof.

The present invention also provides a compound having the structure:

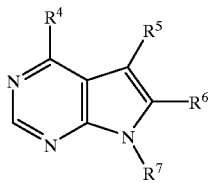

wherein:
R⁴ is —NR₁R₂ or oxo;
R⁵ is —CN or —CSNR₁R₂;
R⁶ is —H, or halo, or —NR₁R₂;
wherein R₁ and R₂ are independently —H or an aliphatic group; and R⁷ is of the formula R₃—Ar, wherein R₃ is an aliphatic group and Ar is an unsubstituted aryl or an aryl independently substituted with halo, nitro, amino, or aliphatic groups; provided that when R⁶ is a —H or —NH₂ and Ar is —C₆H₅ or a phenyl substituted with only one aliphatic group, R₃ is an aliphatic group other than methyl such that —R₃— is not a —CH₂—; and pharmaceutically acceptable salts, prodrugs and derivatives thereof.

In one embodiment, R⁴ is —NH₂; R⁵ is —CN and R⁶ is —H. In another embodiment, R⁴ is —NH₂; R⁵ is —CSNH₂ and R⁶ is —H. In yet another embodiment, R⁴ is —NH₂; R⁵ is —CN and R⁶ is —NH₂. In yet another embodiment, R⁴ is —NH₂; R⁵ is —CN and R⁶ is a halo group. In yet another embodiment, the halo group is a bromo or chloro.

Some embodiments comprise a pyrrolo[2,3-d]pyrimidine compound having the following structural features:
R⁴ is —NH₂; R⁵ is —CN; R⁶ is —H; and R⁷ is —CH(CH₃)—C₆H₄ (1414);
R⁴ is —NH₂; R⁵ is —CN; R⁶ is —H; and R⁷ is —CH₂—C₆H₄-4-F (1429);
R⁴ is —NH₂; R⁵ is —CN; R⁶ is —H; and R⁷ is —CH₂—C₆H₄-4-Cl (1444);
R⁴ is —NH₂; R⁵ is —CN; R⁶ is —H; and R⁷ is —CH₂—C₆H₄-4-NO₂ (1360)
R⁴ is —NH₂; R⁵ is —CN; R⁶ is —H; and R⁷ is —CH₂—C₆H₄-3-NO₂ (1362);
R⁴ is —NH₂; R⁵ is —CN; R⁶ is —NH₂; and R⁷ is —(CH₂)₃—C₆H₅ (1350)
R⁴ is —NH₂; R⁵ is —CSNH₂; R⁶ is —H; and R⁷ is —CH₂—CH₂—C₆H₅ (1446);
R⁴ is —NH₂; R⁵ is —CSNH₂; R⁶ is —H; and R⁷ is —CH₂—CH₂—CH₂—C₆H₅ (1413)
R⁴ is —NH₂; R⁵ is —CN; R⁶ is —H; and R⁷ is —CH₂—CH₂—C₆H₅ (1358 or 1368);
R⁴ is —NH₂; R⁵ is —CN; R⁶ is —NH₂; and R⁷ is —CH(CH₃)—C₆H₅ (1451);
R⁴ is —NH₂; R⁵ is —CN; R⁶ is —NH₂; and R⁷ is —CH₂—C₆H₅ (1369);
R⁴ is —NHCH₃; R⁵ is —CN; R⁶ is —NH₂; and R⁷ is —CH₂—C₆H₄-3-NO₂ (1425);
R⁴ is —NH₂; R⁵ is —CN; R⁶ is —NH₂; and R⁷ is —CH₂—C₆H₄-3-NH₂ (1455);
R⁴ is —NH₂; R⁵ is —CN; R⁶ is —NH₂ and R⁷ is —CH₂—C₆H₄-4-F (1365);
R⁴ is —NH₂; R⁵ is —CN; R⁶ is —NH₂; and R⁷ is —CH₂—C₆H₄-4-Cl (1356);
R⁴ is —NH₂; R⁵ is —CN; R⁶ is —NH₂; and R⁷ is —CH₂—C₆H₄-4-Br (1389);
R⁴ is —NH₂; R⁵ is —CN; R⁶ is —NH₂; and R⁷ is —CH₂—C₆H₄-4-NO₂ (1348);
R⁴ is —NH₂; R⁵ is —CN; R⁶ is —NH₂; and R⁷ is —CH₂—C₆H₄-4-NH₂ (1352)
R⁴ is —NH₂; R⁵ is —CN; R⁶ is —H; and R⁷ is —CH₂—CH═CH—CH₂—C₆H₅ (1372);
R⁴ is —NH₂; R⁵ is —CN; R⁶ is —NH₂; and R⁷ is —CH₂—CH═CH—CH₂—C₆H₅ (1329);
R⁴ is -oxo; R⁵ is —CN; R⁶ is —Br; and R⁷ is —CH₂—C₆H₄-4-CH₃ (1441);
R⁴ is —NH₂; R⁵ is —CN; R⁶ is —Br; and R⁷ is —CH(CH₃)—C₆H₅ (1363);
R⁴ is —NH₂; R⁵ is —CN; R⁶ is —Br; and R⁷ is —CH₂—C₆H₄-4-F (1353);
R⁴ is —NH₂; R⁵ is —CN; R⁶ is —Br; and R⁷ is —CH₂—C₆H₄-4-Cl (1355);
R⁴ is —NH₂; R⁵ is —CN; R⁶ is —Br; and R⁷ is —CH₂—C₆H₄-3-Cl (1461);
R⁴ is —NH₂; R⁵ is —CN; R⁶ is —Br; and R⁷ is —CH₂—C₆H₃-3,4-(Cl)₂ (1462);
R⁴ is —NH₂; R⁵ is —CN; R⁶ is —Br; and R⁷ is —CH₂—C₆H₄-4-Br (1373);
R⁴ is —NH₂; R⁵ is —CN; R⁶ is —Br; and R⁷ is —CH₂—C₆H₄-4-NO₂ (1374);
R⁴ is —NH—CH₃; R⁵ is —CN; R⁶ is —Br; and R⁷ is —CH₂—CH₂—C₆H₅ (1463);
R⁴ is —NH₂; R⁵ is —CN; R⁶ is —Br and R⁷ is —CH₂—CH₂—C₆H₅ (1351);
R⁴ is —NH₂; R⁵ is —CN; R⁶ is —Br; and R⁷ is —(CH₂)₃—C₆H₅ (1347); and
R⁴ is —NH₂; R⁵ is —CN; R⁶ is —Br; and R⁷ is —CH₂—CH═CH—C₆H₅ (1361).

In one embodiment, the present invention provides for a compound having the structure:

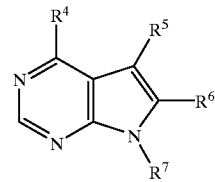

wherein:
R⁴ is —NR₁R₂ or oxo;

$R^5$ is —CONR$_1$R$_2$;
$R^6$ is —H, or halo, or —NR$_1$R$_2$;
wherein R$_1$ and R$_2$ are independently —H or an aliphatic group; and R$^7$ is of the formula R$_3$—Ar, wherein R$_3$ is an aliphatic group and Ar is an unsubstituted aryl or an aryl independently substituted with halo, nitro, amino, or aliphatic groups; and pharmaceutically acceptable salts, prodrugs and derivatives thereof.

In one embodiment, $R^4$ is —NH$_2$; $R^5$ is —CONR$_1$R$_2$ and $R^6$ is a halo group. In another embodiment, R$_1$ and R$_2$ are independently —H or an aliphatic group and the halo group is a chloro or bromo. In yet another embodiment, $R^4$ is —NH$_2$; $R^5$ is —CONH$_2$ and $R^6$ is bromo.

Some embodiments comprise a pyrrolo[2,3-d]pyrimidine compound having the following structural features:
$R^4$ is —NH$_2$; $R^5$ is —CONH$_2$; $R^6$ is —H; and $R^7$ is —CH$_2$C$_6$H$_5$ (659);
$R^4$ is —NH$_2$; $R^5$ is —CONH$_2$; $R^6$ is —H; and $R^7$ is —CH(CH$_3$)—C$_6$H$_5$ (1428);
$R^4$ is —NH$_2$; $R^5$ is —CONH$_2$; $R^6$ is —H; and $R^7$ is —CH$_2$—C$_6$H$_4$-2-CH$_3$ (836);
$R^4$ is —NH$_2$; $R^5$ is —CONH$_2$; $R^6$ is —H; and $R^7$ is —CH$_2$—C$_6$H$_4$-3-CH$_3$ (826);
$R^4$ is —NH$_2$; $R^5$ is —CONH$_2$; $R^6$ is —H; and $R^7$ is —CH$_2$—C$_6$H$_4$-4-CH$_3$ (658);
$R^4$ is —NH$_2$; $R^5$ is —CONH$_2$; $R^6$ is —H; and $R^7$ is —CH$_2$—C$_6$H$_4$-4-C(CH$_3$)$_3$ (854);
$R^4$ is —NH$_2$; $R^5$ is —CONH$_2$; $R^6$ is —H; and $R^7$ is —CH$_2$—C$_6$H$_4$-4-OCH$_3$ (839);
$R^4$ is —NH$_2$; $R^5$ is —CONH$_2$; $R^6$ is —H; and $R^7$ is —CH$_2$—C$_6$H$_4$-4-F (1419);
$R^4$ is —NH$_2$; $R^5$ is —CONH$_2$; $R^6$ is —H; and $R^7$ is —CH$_2$—C$_6$H$_4$-4-NO$_2$ (1412);
$R^4$ is —NH$_2$; $R^5$ is —CONH$_2$; $R^6$ is —H; and $R^7$ is —CH$_2$—C$_6$H$_4$-3-NO$_2$ (1421);
$R^4$ is —NH$_2$; $R^5$ is —CONH$_2$; $R^6$ is —Br; and $R^7$ is —CH$_2$—C$_6$H$_4$-4-Cl (1443)
$R^4$ is —NH$_2$; $R^5$ is —CONH$_2$; $R^6$ is —Br; and $R^7$ is —CH$_2$—C$_6$H$_4$-4-CH$_3$ (1427);
$R^4$ is —NH$_2$; $R^5$ is —CONH$_2$; $R^6$ is —H; and $R^7$ is —CH$_2$—CH$_2$—C$_6$H$_5$ (1396);
$R^4$ is —NH$_2$; $R^5$ is —CONH$_2$; $R^6$ is —Br; and $R^7$ is —CH$_2$—CH$_2$—C$_6$H$_5$ (1409); and
$R^4$ is —NH$_2$; $R^5$ is —CONH$_2$; $R^6$ is —H; and $R^7$ is —CH$_2$—CH$_2$—CH$_2$—C$_6$H$_5$ (1362)

Another embodiment provides for a compound having the structure

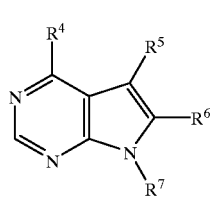

wherein:
$R^4$ is —NR$_1$R$_2$ or oxo;
$R^5$ is —CN, or —CSNR$_1$R$_2$, or —CONR$_1$R$_2$;
$R^6$ is halo;
wherein R$_1$ and R$_2$ are independently —H or an aliphatic group; and R$^7$ is of the formula R$_3$—Ar, wherein R$_3$ is an aliphatic group and Ar is an unsubstituted aryl or an aryl independently substituted with halo, nitro, amino, or aliphatic groups; provided that when $R^6$ is bromo and Ar is —C$_6$H$_5$ or a phenyl substituted with only one aliphatic group, R$_3$ is an aliphatic group other than methyl such that —R$_3$— is not a —CH$_2$—; and its pharmaceutically acceptable salts, prodrugs and derivatives thereof.

In one embodiment, $R^4$ is —NH$_2$; $R^5$ is —CN or —CONR$_1$R$_2$ and $R^6$ is a halo group. In another embodiment, R$_1$ and R$_2$ are independently —H or an aliphatic group and the halo group is a chloro or bromo.

Some embodiments comprise a pyrrolo[2,3-d]pyrimidine compound having the following structural features:
$R^4$ is -oxo; $R^5$ is —CN; $R^6$ is —Br; and $R^7$ is —CH$_2$—C$_6$H$_4$-4-CH$_3$ (1441);
$R^4$ is —NH$_2$; $R^5$ is —CN; $R^6$ is —Br; and $R^7$ is —CH(CH$_3$)—C$_6$H$_5$ (1363);
$R^4$ is —NH$_2$; $R^5$ is —CN; $R^6$ is —Br; and $R^7$ is —CH$_2$—C$_6$H$_4$-4-F (1353);
$R^4$ is —NH$_2$; $R^5$ is —CONH$_2$; $R^6$ is —Br; and $R^7$ is —CH$_2$—C$_6$H$_4$-4-Cl (1443);
$R^4$ is —NH$_2$; $R^5$ is —CN; $R^6$ is —Br; and $R^7$ is —CH$_2$—C$_6$H$_4$-4-Cl (1355);
$R^4$ is —NH$_2$; $R^5$ is —CN; $R^6$ is —Br; and $R^7$ is —CH$_2$—C$_6$H$_4$-3-Cl (1461);
$R^4$ is —NH$_2$; $R^5$ is —CN; $R^6$ is —Br; and $R^7$ is —CH$_2$—C$_6$H$_3$-3,4-(Cl)$_2$ (1462);
$R^4$ is —NH$_2$; $R^5$ is —CN; $R^6$ is —Br; and $R^7$ is —CH$_2$—C$_6$H$_4$-4-Br (1373);
$R^4$ is —NH$_2$; $R^5$ is —CN; $R^6$ is —Br; and $R^7$ is —CH$_2$—C$_6$H$_4$-4-NO$_2$ (1374);
$R^4$ is —NH$_2$; $R^5$ is —CONH$_2$; $R^6$ is —Br; and $R^7$ is —CH$_2$—C$_6$H$_4$-4-CH$_3$ (1427);
$R^4$ is —NH—CH$_3$; $R^5$ is —CN; $R^6$ is —Br; and $R^7$ is —CH$_2$—CH$_2$—C$_6$H$_5$ (1463);
$R^4$ is —NH$_2$; $R^5$ is —CN; $R^6$ is —Br and $R^7$ is —CH$_2$—CH$_2$—C$_6$H$_5$ (1351);
$R^4$ is —NH$_2$; $R^5$ is —CONH$_2$; $R^6$ is —Br; and $R^7$ is —CH$_2$—CH$_2$—C$_6$H$_5$ (1409)
$R^4$ is —NH$_2$; $R^5$ is —CN; $R^6$ is —Br; and $R^7$ is —(CH$_2$)$_3$C$_6$H$_5$ (1347); and
$R^4$ is —NH$_2$; $R^5$ is —CN; $R^6$ is —Br; and $R^7$ is —CH$_2$—CH=CH—C$_6$H$_5$ (1361).

Yet another embodiment provides for a compound having the structure

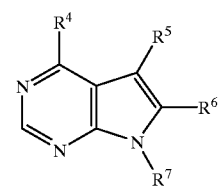

wherein:
$R^4$ is —NR$_1$R$_2$ or oxo;
$R^5$ is —CN, or —CSNR$_1$R$_2$, or —CONR$_1$R$_2$;
$R^6$ is —H, or halo, or —NR$_1$R$_2$;
wherein R$_1$ and R$_2$ are independently —H or an aliphatic group; and R$^7$ is of the formula R$_3$—Ar, wherein R$_3$ is an aliphatic group and Ar is an aryl independently substituted with halo, nitro, amino groups; and pharmaceutically acceptable salts, prodrugs and derivatives thereof.

In one embodiment, $R^4$ is —NH$_2$; $R^5$ is —CN or —CONR$_1$R$_2$; $R^6$ is —H or a halo group. In another embodiment, R$_1$ and R$_2$ are independently —H or an aliphatic group and the halo group is a chloro or bromo.

Some embodiments comprise a pyrrolo[2,3-d]pyrimidine compound having the following structural features:

$R^4$ is —$NH_2$; $R^5$ is —CN; $R^6$ is —H; and $R^7$ is —$CH_2$—$C_6H_4$-4-F (1429);

$R^4$ is —$NH_2$; $R^5$ is —CN; $R^6$ is —H; and $R^7$ is —$CH_2$—$C_6H_4$-4-Cl (1444);

$R^4$ is —$NH_2$; $R^5$ is —CN; $R^6$ is —H; and $R^7$ is —$CH_2$—$C_6H_4$-4-$NO_2$ (1360);

$R^4$ is —$NH_2$; $R^5$ is —CN; $R^6$ is —H; and $R^7$ is —$CH_2$—$C_6H_4$-3-$NO_2$ (1362);

$R^4$ is —$NH_2$; $R^5$ is —$CONH_2$; $R^6$ is —H; and $R^7$ is —$CH_2$13 $C_6H_4$-4-F (1419);

$R^4$ is —$NH_2$; $R^5$ is —$CONH_2$; $R^6$ is —H; and $R^7$ is —$CH_2$—$C_6H_4$-4-$NO_2$ (1412);

$R^4$ is —$NH_2$; $R^5$ is —$CONH_2$; $R^6$ is —H; and $R^7$ is —$CH_2$—$C_6H_4$-3-$NO_2$ (1421)

$R^4$ is —$NH_2$; $R^5$ is —$CONH_2$; $R^6$ is —Br; and $R^7$ is —$CH_2$—$C_6H_4$-4-Cl (1443);

$R^4$ is —$NH_2$; $R^5$ is —CN; $R^6$ is —Br; and $R^7$ is —$CH_2$—$C_6H_4$-4-Cl (1388) or (1355);

$R^4$ is —$NH_2$; $R^5$ is —CN; $R^6$ is —Br; and $R^7$ is —$CH_2$—$C_6H_4$-3-Cl (1461);

$R^4$ is —$NH_2$; $R^5$ is —CN; $R^6$ is —Br; and $R^7$ is —$CH_2$—$C_6H_3$-3,4-$(Cl)_2$ (1462);

$R^4$ is —$NH_2$; $R^5$ is —CN; $R^6$ is —Br; and $R^7$ is —$CH_2$—$C_6H_4$-4-Br (1373);

$R^4$ is —$NH_2$; $R^5$ is —CN; $R^6$ is —Br; and $R^7$ is —$CH_2$—$C_6H_4$-4-$NO_2$ (1331);

$R^4$ is —$NH_2$; $R^5$ is —CN; $R^6$ is —Br; and $R^7$ is —$CH_2$—$C_6H_4$-3-$NO_2$ (1374);

$R^4$ is —$NH_2$; $R^5$ is —CN; $R^6$ is —$NH_2$; and $R^7$ is —$CH_2$—$C_6H_4$-4-F (1365);

$R^4$ is —$NH_2$; $R^5$ is —CN; $R^6$ is —$NH_2$; and $R^7$ is —$CH_2$—$C_6H_4$-4-Cl (1356)

$R^4$ is —$NH_2$; $R^5$ is —CN; $R^6$ is —$NH_2$; and $R^7$ is —$CH_2$—$C_6H_4$-4-Br (1389);

$R^4$ is —$NH_2$; $R^5$ is —CN; $R^6$ is —$NH_2$; and $R^7$ is —$CH_2$—$C_6H_4$-4-$NO_2$ (1348);

$R^4$ is —$NH_2$; $R^5$ is —CN; $R^6$ is —$NH_2$; and $R^7$ is —$CH_2$—$C_6H_4$-4-$NH_2$ (1352);

$R^4$ is —$NH_2$; $R^5$ is —CN; $R^6$ is —$NH_2$; and $R^7$ is —$CH_2$—$C_6H_4$-3-$NO_2$ (1425); and $R^4$ is —$NH_2$; $R^5$ is —CN; $R^6$ is —$NH_2$; and $R^7$ is —$CH_2$—$C_6H_4$-4-$NH_2$ (1455).

In one aspect, the present invention provides for a compound having the structure

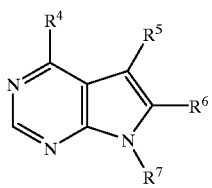

wherein:
$R^4$ is —$NR_1R_2$ or oxo;
$R^5$ is —CN, or —$CSNR_1R_2$, or —$CONR_1R_2$;
$R^6$ is —H, or halo, or —$NR_1R_2$;
wherein $R_1$ and $R_2$ are independently —H or an aliphatic group; and $R^7$ is of the formula $R_3$—Ar, wherein $R_3$ is an aliphatic group and Ar is an unsubstituted aryl or an aryl independently substituted with halo, nitro, amino, or aliphatic groups; provided that $R_3$ is an aliphatic group other than methyl such that —$R_3$— is not a —$CH_2$—; and pharmaceutically acceptable salts, prodrugs and derivatives thereof.

In one embodiment, $R^4$ is —$N_2$; $R^5$ —CN or —$CONR_1R_2$ or —$CSNR_1R_2$; and $R^6$ is —H or —$NH_2$, or a halo group.

In another embodiment, $R^1$ and $R_2$ are independently —H or an aliphatic group and the halo group is a chloro or bromo.

Some embodiments comprise a pyrrolo[2,3-d]pyrimidine compound having the following structural features:

$R^4$ is —$NH_2$; $R^5$ is —CN; $R^6$ is —Br; and $R^7$ is —CH($CH_3$)—$C_6H_5$ (1363);

$R^4$ is —$NH_2$; $R^5$ is —CN; $R^6$ is —$NH_2$; and $R^7$ is —CH($CH_3$)—$C_6H_5$ (1451);

$R^4$ is —$NH_2$; $R^5$ —CN; $R^6$ is —H; and $R^7$ is —$CH_2$—$CH_2$—$C_6H_5$ (1368);

$R^4$ is —$NH_2$; $R^5$ is —$CONH_2$; $R^6$ is —H; and $R^7$ is —$CH_2$—$CH_2$—$C_6H_5$ (1396);

$R^4$ is —$NH_2$; $R^5$ is —$CSNH_2$; $R^6$ is —H; and $R^7$ is —$CH_2$—$CH_2$—$C_6H_5$ (1446);

$R^4$ is —$NH_2$; $R^5$ is —CN; $R^6$ is —$NH_2$; and $R^7$ is —$CH_2$—$CH_2$—$C_6H_5$ (1369);

$R^4$ is —$NH_2$; $R^5$ is —$CSNH_2$; $R^6$ is —H; and $R^7$ is —$CH_2$—$CH_2$—$CH_2$—$C_6H_5$ (1413);

$R^4$ is —$NH_2$; $R^5$ is —$CONH_2$; $R^6$ is —H; and $R^7$ is —$CH_2$—$CH_2$—$CH_2$—$C_6H_5$ (1376);

$R^4$ is —$NH_2$; $R^5$ is —CN; $R^6$ is —H; and $R^7$ is —$CH_2$—$CH_2$—$C_2$—$C_6H_5$ (1362);

$R^4$ is —NH—$CH_3$; $R^5$ is —CN; $R^6$ is —Br; and $R^7$ is —$CH_2$—$CH_2$—$C_6H_5$ (1463);

$R^4$ is —$NH_2$; $R^5$ is —CN; $R^6$ is —Br; and $R^7$ is —$CH_2$—$C_6H_5$ (1351);

$R^4$ is —$NH_2$; $R^5$ is —$CONH_2$; $R^6$ is —Br; and $R^7$ is —$CH_2$—$CH_2$—$C_6H_5$ (1409);

$R^4$ is —$NH_2$; $R^5$ is —CN; $R^6$ is —Br; and $R^7$ is —$(CH_2)_3$—$C_6H_5$ (1347);

$R^4$ is —$NH_2$; $R^5$ is —CN; $R^6$ is —Br; and $R^7$ is —$CH_2$—CH=CH—$C_6H_5$ (1361);

$R^4$ is —$NH_2$; $R^5$ is —CN; $R^6$ is —$NH_2$; and $R^7$ is —$CH_2$—$CH_2$—$C_6H_5$ (1350);

$R^4$ is —$NH_2$; $R^5$ is —CN; $R^6$ is —H; and $R^7$ is —$CH_2$—CH=CH—$C_6H_5$ (1372); and $R^4$ is —$NH_2$; $R^5$ is —CN; $R^6$ is —$NH_2$; and $R^7$ is —$CH_2$—CH=CH—$C_6H_5$ (1329).

The present invention provides for a pharmaceutical composition comprising a therapeutically effective amount of one or more compounds of the above embodiments, their pharmaceutically acceptable salts, prodrugs or derivatives and a pharmaceutically acceptable carrier. Such pharmaceutical compositions can be used to treat or prevent a variety of viral infections such as HCMV, HSV-1, HBV, HCV, among others.

One embodiment of the present invention has a compound having the following structure (1429):

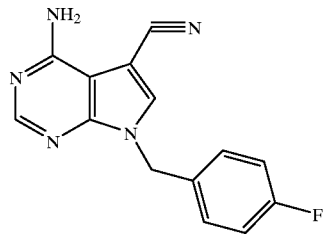

Another embodiment of the present invention has a compound having the following structure (1444):

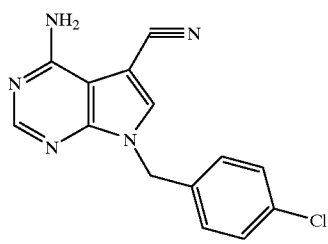

Another embodiment of the present invention has a compound having the following structure (1360):

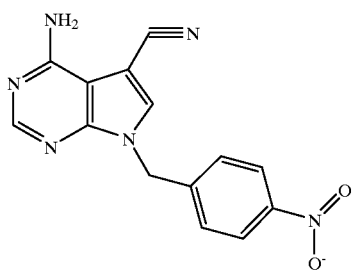

Yet another embodiment of the present invention has a compound having the following structure (1353):

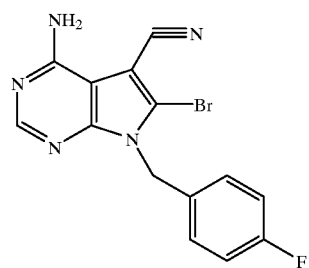

A further embodiment of the present invention has a compound having the following structure (1365):

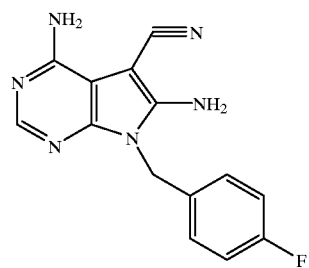

Another embodiment of the present invention has a compound having the following structure (1356):

Another embodiment of the present invention has a compound having the following structure (1389):

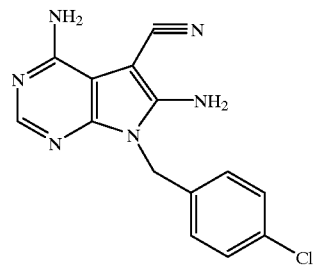

Yet another embodiment of the present invention has a compound having the following structure (1348):

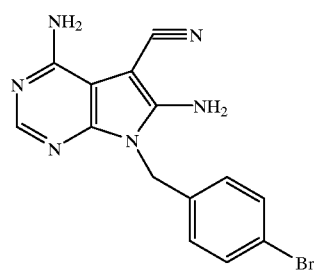

Another embodiment of the present invention has a compound having the following structure (1446):

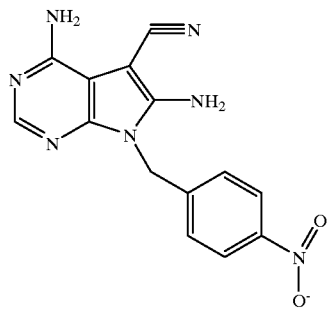

One further embodiment of the present invention has a compound having the following structure (1351):

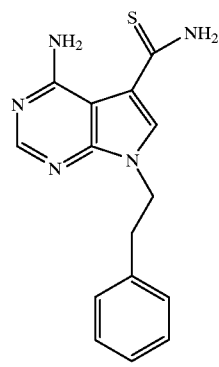

Another embodiment of the present invention has a compound having the following structure (1368):

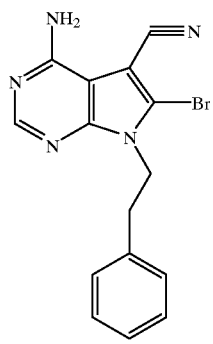

Yet another embodiment of the present invention has a compound having the following structure (1369):

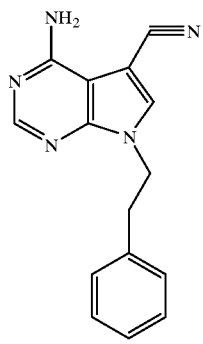

Another specific embodiment of the present invention has a compound having the following structure (1413):

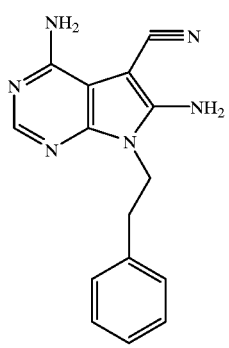

The present invention provides for a method for treating or preventing a viral infection comprising administering an effective amount of one or more compounds of the following structure:

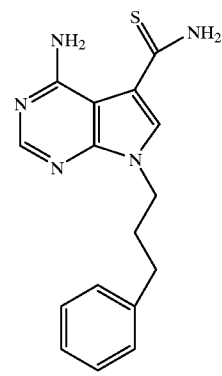

wherein:
  $R^4$ is —$NR_1R_2$ or oxo;
  $R^5$ is —CN, or —$CSNR_1R_2$, or —$CONR_1R_2$;
  $R^6$ is —H, or halo, or —$NR_1R_2$;
  wherein $R_1$ and $R_2$ are independently —H or an aliphatic group; and $R^7$ is of the formula $R_3$—Ar, wherein $R_3$ is an aliphatic group and Ar is an unsubstituted aryl or an aryl independently substituted with halo, nitro, amino, or aliphatic groups; and pharmaceutically acceptable salts, prodrugs and derivatives thereof.

In one embodiment of the above method, the one or more compounds have the following structure:

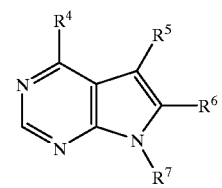

wherein:
  $R^4$ is —$NR_1R_2$ or oxo;
  $R^5$ is —CN or —$CSNR_1R_2$;

$R^6$ is —H, or halo, or —$NR_1R_2$;

wherein $R_1$ and $R_2$ are independently —H or an aliphatic group; and $R^7$ is of the formula $R_3$—Ar, wherein $R_3$ is an aliphatic group and Ar is an unsubstituted aryl or an aryl independently substituted with halo, nitro, amino, or aliphatic groups.

In another embodiment, $R^4$ is —$NH_2$; $R^5$ is —CN and $R^6$ is —H. In another embodiment, $R^4$ is —$NH_2$; $R^5$ is —$CSNH_2$ and $R^6$ is —H. In another embodiment, $R^4$ is —$NH_2$; $R^5$ is —CN and $R^6$ is —$NH_2$. In another embodiment, $R^4$ is ——$NH_2$; $R^5$ is —CN and $R^6$) is a halo group. In another embodiment, the halo group is a bromo or chloro.

Some embodiments comprise a pyrrolo[2,3-d]pyrimidine compound having the following structural features:

$R^4$ is —$NH_2$; $R^5$ is —CN; $R^6$ is —H; and $R^7$ is —CH($CH_3$)—$C_6H_4$ (1414);

$R^4$ is —$NH_2$; $R^5$ is —CN; $R^6$ is —H; and $R^7$ is —$CH_2$—$C_6H_4$-4-F (1429);

$R^4$ is —$NH_2$; $R^5$ is —CN; $R^6$ is —H; and $R^7$ is —$CH_2$—$C_6H_4$-4-Cl (1444);

$R^4$ is —$NH_2$; $R^5$ is —CN; $R^6$ is —H; and $R^7$ is —$CH_2$—$C_6H_4$-4-$NO_2$ (1360);

$R^4$ is —$NH_2$; $R^5$ is —CN; $R^6$ is —H; and $R^7$ is —$CH_2$—$C_6H_4$-3-$NO_2$ (1362);

$R^4$ is —$NH_2$; $R^5$ is —CN; $R^6$ is —$NH_2$; and $R^7$ is —$(CH_2)_3$—$C_6H_5$ (1350)

$R^4$ is —$NH_2$; $R^5$ is —$CSNH_2$; $R^6$ is —H; and $R^7$ is —$CH_2$—$CH_2$—$C_6H_5$ (1446)

$R^4$ is —$NH_2$; $R^5$ is —$CSNH_2$; $R^6$ is —H; and $R^7$ is —$CH_2$—$CH_2$—$CH_2$—$C_6H_5$ (1413);

$R^4$ is —$NH_2$; $R^5$ is —CN; $R^6$ is —H; and $R^7$ is —$CH_2$—$CH_2$—$C_6H_5$ (1368);

$R^4$ is —$NH_2$; $R^5$ is —CN; $R^6$ is —$NH_2$; and $R^7$ is —CH($CH_3$)—$C_6H_5$ (1451);

$R^4$ is —$NH_2$; $R^5$ is —CN; $R^6$ is —$NH_2$; and $R^7$ is —$CH_2$—$CH_2$—$C_6H_5$ (1369);

$R^4$ is —$NHCH_3$; $R^5$ is —CN; $R^6$ is —$NH_2$; and $R^7$ is —$CH_2$—$C_6H_4$-3-$NO_2$ (1425);

$R^4$ is —$NH_2$; $R^5$ is —CN; $R^6$ is —$NH_2$; and $R^7$ is —$CH_2$—$C_6H_4$-3-$NH_2$ (1455);

$R^4$ is —$NH_2$; $R^5$ is —CN; $R^6$ is —$NH_2$; and $R^7$ is —$CH_2$—$C_6H_4$-4-F (1365);

$R^4$ is —$NH_2$; $R^5$ is —CN; $R^6$ is —$NH_2$; and $R^7$ is —$CH_2$—$C_6H_4$-4-Cl (1356);

$R^4$ is —$NH_2$; $R^6$ is —CN; $R^6$ is —$NH_2$; and $R^7$ is —$CH_2$—$C_6H_4$-4-Br (1389);

$R^4$ is —$NH_2$; $R^5$ is —CN; $R^6$ is —$NH_2$; and $R^7$ is —$CH_2$—$C_6H_4$-4-$NO_2$ (1348);

$R^4$ is —$NH_2$; $R^5$ is —CN; $R^6$ is —$NH_2$; and $R^7$ is —$CH_2$—$C_6H_4$-4-$NH_2$ (1352);

$R^4$ is —$NH_2$; $R^6$ is —CN; $R^6$ is —H; and $R^7$ is —CH=CH—$CH_2$—$C_6H_5$ (1372);

$R^4$ is —$NH_2$; $R^5$ is —CN; $R^6$ is —$NH_2$; and $R^7$ is —$CH_2$—CH=CH—$CH_2$—$C_6H_5$ (1329);

$R^4$ is —oxo; $R^5$ is —CN; $R^6$ is —Br; and $R^7$ is —$CH_2$—$C_6H_4$-4-$CH_3$ (1441);

$R^4$ is —$NH_2$; $R^5$ is —CN; $R^6$ is —Br; and $R^7$ is —CH($CH_2$)—$C_6H_5$ (1363);

$R^4$ is —$NH_2$; $R^5$ is —CN; $R^6$ is —Br; and $R^7$ is —$CH_2$—$C_6H_4$-4-F (1353);

$R^4$ is —$NH_2$; $R^5$ is —CN; $R^6$ is —Br; and $R^7$ is —$CH_2$—$C_6H_4$-4-Cl (1355);

$R^4$ is —$NH_2$; $R^5$ is —CN; $R^6$ is —Br; and $R^7$ is —$CH_2$—$C_6H_4$-3-Cl (1461);

$R^4$ is —$NH_2$; $R^5$ is —CN; $R^6$ is —Br; and $R^7$ is —$CH_2$—$C_6H_3$-3,4-$(Cl)_2$ (1462);

$R^4$ is —$NH_2$; $R^5$ is —CN; $R^6$ is —Br; and $R^7$ is —$CH_2$—$C_6H_4$-4-Br (1373);

$R^4$ is —$NH_2$; $R^5$ is —CN; $R^6$ is —Br; and $R^7$ is —$CH_2$—$C_6H_4$-4-$NO_2$ (1374);

$R^4$ is —NH—$CH_3$; $R^5$ is —CN; $R^6$ is —Br; and $R^7$ is —$CH_2$—$CH_2$—$C_6H_5$ (1463);

$R^4$ is —$NH_2$; $R^5$ is —CN; $R^6$ is —Br and $R^7$ is —$CH_2$—$CH_2$—$C_6H_5$ (1351);

$R^4$ is —$NH_2$; $R^5$ is —CN; $R^6$ is —Br; and $R^7$ is —$(CH_2)_3$—$C_6H_5$ (1347); and $R^4$ is —$NH_2$; $R^5$ is —CN; $R^6$ is —Br; and $R^7$ is —$CH_2$—CH=CH—$C_6H_5$ (1361).

In another embodiment of the method, one or more compounds have the following structure:

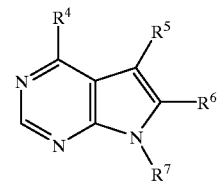

wherein:
$R^4$ is —$NR_1R_2$ or oxo;
$R^5$ is —$CONR_1R_2$;
$R^6$ is —H, or halo, or —$NR_1R_2$;
wherein $R_1$ and $R_2$ are independently —H or an aliphatic group; and $R^7$ is of the formula $R_3$—Ar, wherein $R_3$ is an aliphatic group and Ar is an unsubstituted aryl or an aryl independently substituted with halo, nitro, amino, or aliphatic groups.

In another embodiment, one or more compounds have the following structure:

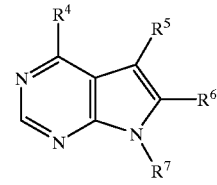

wherein:
$R^4$ is —$NR_1R_2$ or oxo;
$R^5$ is —CN, or —$CSNR_1R_2$, or —$CONR_1R_2$;
$R^6$ is halo;
wherein $R_1$ and $R_2$ are independently —H or an aliphatic group; and $R^7$ is of the formula $R_3$—Ar, wherein $R_3$ is an aliphatic group and Ar is an unsubstituted aryl or an aryl independently substituted with halo, nitro, amino, or aliphatic groups.

In another embodiment of the method, the one or more compounds have the following structure:

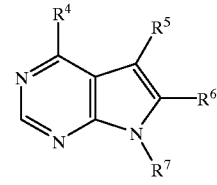

wherein:
$R^4$ is —$NR_1$ $R_2$ or oxo;

R[5] is —CN, or —CSNR$_1$R$_2$, or —CONR$_1$R$_2$;
R[6] is —H, or halo, or —NR$_1$R$_2$;
wherein R$_1$ and R$_2$ are independently —H or an aliphatic group; and R[7] is of the formula R$_3$—Ar, wherein R$_3$ is an aliphatic group and Ar is an aryl independently substituted with halo, nitro, amino groups.

In yet another embodiment of the method, one or more compounds have the following structure:

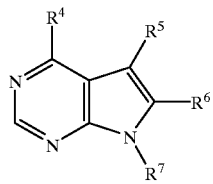

wherein:
R[4] is —NR$_1$R$_2$ or oxo;
R[5] is —CN, or —CSNR$_1$R$_2$, or —CONR$_1$R$_2$;
R[6] R is —H, or halo, or —NR$_1$R$_2$;
wherein R$_1$ and R$_2$ are independently —H or an aliphatic group; and R[7] is of the formula R$_3$—Ar, wherein R$_3$ is an aliphatic group and Ar is an unsubstituted aryl or an aryl independently substituted with halo, nitro, amino, or aliphatic groups.

In one embodiment, the virus is a herpes virus, or hepatitis B virus or hepatitis C virus. In another embodiment, the herpes virus is selected from the group consisting of herpes simplex virus type 1, herpes simplex virus type 2, herpesvirus type 6, varicella-zoster virus, Epstein-Barr virus, herpesvirus saimiri; equine herpesvirus-1, equine herpesvirus-2, and equine herpesvirus-3.

In another embodiment, at least one of the above compounds is used in the prevention or treatment of a viral infection. In another embodiment, at least one of the above compounds is used for the preparation of a medicament for the prevention or treatment of a viral infection. The compounds also can be used in an in vitro assay to identify other therapeutically effective compounds. The compounds can also be used in vitro to predict efficacy against a viral infection in vivo.

A further embodiment of this invention pertains to methods for treating and/or preventing a hepatitis viral infection, e.g, hepatitis B and hepatitis C, comprising contacting the virus with an effective amount of an antiviral pyrrolo[2,3-d]pyrimidine compound of the present invention, alone or in combination with a carrier such as a pharmaceutically acceptable carrier.

The invention also includes pharmaceutically acceptable salts, prodrugs and derivatives, such as esters, of the above-described compounds. [Remington's Pharmaceutical Sciences, Mack Publishing Co., Easton, Pa. (latest edition)].

Another aspect of the invention is a method for inhibiting replication or viral infectivity in a subject by administering an effective amount of one or more of the above-described compounds to the subject.

Still another aspect of the invention is a composition for preventing or treating viral infections containing an effective amount of one or more of the above-described compounds and an acceptable carrier, e.g., a pharmaceutically acceptable carrier.

DETAILED DESCRIPTION OF THE INVENTION

Throughout this application, various references including but not limited to publications, patents, and published patent applications are referred to by an identifying citation. The disclosure of these references, e.g., publications, patents, and published patent specifications referenced in this application are hereby incorporated by reference into the present disclosure to more fully describe the state of the art to which this invention pertains.

The present invention provides several novel non-phosphorylatable, non-nucleoside pyrrolo[2,3-d]pyrimidines which are useful in the treatment or prevention of viral infections.

A. Chemical Structure

The term "nucleoside derivative" as used herein relates to pyrrolo[2,3-d]pyrimidine compounds which have a modified but intact furan ring at N-7 (R[7]). Examples include 2',3'-dideoxy-2',3'-didehydro-β-D-ribofuranose and 2',3'-dideoxy-β-D-ribofuranose.

The term "non-nucleoside derivative" as used herein relates to pyrrolo[2,3-d]pyrimidine compounds which do not have a modified or intact furan ring at N-7 (R[7]) but are substituted at R[7] instead with a variety of aralkyl radicals such as unsubstituted benzyls, substituted benzyls, substituted alkylphenyls, substituted alkenylphenyls, wherein the substitutions comprise a variety of groups such as halo, nitro, amino, alkyl among others.

The term "non-nucleoside, non-phosphorylatable derivative" as used herein relates to pyrrolo[2,3-d]pyrimidine compounds which do not have a modified or intact furan ring at N-7 (R[7]) and are not substituted at R[7] with a radical having an available —OH (hydroxyl) group and thereby cannot be phosphorylated to an active metabolite. Examples of such substituents include various aryl, aralkyl, and oxyhydrocarbyl radicals.

The terms "thioamide" and "thiocarboxamide" are used synonymously herein. Similarly, the terms "nitrile" and "carbonitrile" are used synonymously herein. The terms "selenamide" and "selenocarboxamide" are used synonymously herein to denote compounds having a —CSeNH$_2$ group.

The term "aryl" as used herein is generic to monocyclic aromatic radicals which may be unsubstituted, substituted, or multiply substituted. Examples of such substituents include —CH$_3$, —CH$_2$CH$_3$, —C(CH$_3$)$_3$, —OCH$_3$, and —OCH$_2$CH$_3$. Examples of aryls include —C$_6$H$_5$, methylphenyl (such as —C6 H4-2-CH$_3$, —C$_6$H$_4$-3-CH$_3$, and —C$_6$H$_4$-4-CH$_3$), dimethylphenyl (such as 2,3-dimethylphenyl, 2,4-dimethylphenyl, 2,5-dimethylphenyl, and the like), trimethylphenyl (such as 2,4,6-trimethylphenyl and the like), methoxyphenyl (such as —C$_6$H$_4$-2-OCH$_3$, —C$_6$H$_4$-3-OCH$_3$, and —C$_6$H$_4$-4-OCH$_3$), dimethoxyphenyl (such as 2,3-dimethoxyphenyl, 2,4-dimethoxyphenyl, 2,5-dimethoxyphenyl, and the like), (tert-butyl)phenyl (such as —C$_6$ H$_4$-2-C(CH$_3$)$_3$, —C$_6$H$_4$-3-C(CH$_3$)$_3$, and —C$_6$ H$_4$-4-C(CH$_3$)$_3$), di(tert-butyl)phenyl (such as 2,3-di(tert-butyl)phenyl, 2,4-di(tert-butyl)phenyl, 2,5-di(tert-butyl)phenyl, and the like), methoxymethylphenyl (such as 4-methoxy-2-methylphenyl and the like), and tert-butylmethylphenyl (such as 4-(tert-butyl)-2-methylphenyl and the like).

The term "aralkyl" as used herein is generic to alkyl radicals having an aryl group. Examples of aralkyls include —CH$_2$—C$_6$H$_5$, methylbenzyl (such as —CH$_2$—C$_6$H$_4$-2-CH$_3$, —CH$_2$—C$_6$H$_4$-3-CH$_3$, —CH$_2$—C$_6$ H$_4$-4-CH$_3$), dimethylbenzyl (such 2,3-dimethylbenzyl, 2,4-dimethylbenzyl, 2,5-dimethylbenzyl, and the like), methoxybenzyl (such as —CH$_2$—C$_6$H$_4$-2-OCH$_3$, —CH$_2$—C$_6$H$_4$-3-OCH$_3$, —CH$_2$—C$_6$H$_4$-4-OCH$_3$), dimethoxybenzyl (such as 2,3-dimethoxybenzyl, 2,4-dimethoxybenzyl, 2,5- dimethoxybenzyl, and the like), (tert-butyl)benzyl (such as —CH$_2$—C$_6$H$_4$-2-C(CH$_3$)$_3$, —CH$_2$—C$_6$H$_4$-3-C(CH$_3$)$_3$, —CH$_2$—C$_6$H$_4$-4-C(CH$_3$)$_3$), di(tert-butyl)benzyl (such as 3,3-di(tert-butyl)benzyl, 2,4-di(tert-butyl)benzyl, 2,5-di (tert-butyl)benzyl, and the like), methoxymethylbenzyl (such as 4-methoxy-2-methylbenzyl and the like), tert-butylmethylbenzyl (such as 4-(tert-butyl)-2-methylbenzyl and the like), phenylethyl (such as 1-phenylethyl and 2-phenylethyl), phenylpropyl (such as 3-phenylpropyl and the like), and methoxyphenylethyl (such as 2-(2-methoxyphenyl)ethyl and the like). The substituent groups include halo, nitro, amino groups. Optionally, the amino group could be a derivatized amino group.

Thus the term "substituted aralkyl" includes substituted phenyl and benzyl groups, wherein the phenyl ring is substituted with one or more of the above mentioned groups.

The term "hydrocarbyl" as used herein is generic to radicals derived from hydrocarbons. The term "oxy-hydrocarbyl" as used herein is generic to hydrocarbyl radicals having at least one oxy-group. The term "oxy-group" as used herein is generic to R—O—R linkages, excluding those arising from substituents on aryl groups. Examples of oxy-groups include —CH$_2$—O—CH$_2$—, —CH$_2$—O—C$_6$H$_4$—, and —CH$_2$—O—CH(CH$_3$)—, but not —C$_6$H$_4$-2-OCH$_3$.

The term "aliphatic" as used herein is generic to linear, branched, or multiply-branched acyclic species. Examples of acyl or acyl derivatized groups include —C(=O)H, —C(=O)R, —C(=O)OH, —C(=O)OR, —C(=O)NHR, and the like.

Examples of aliphatic oxy-hydrocarbyls having 2 to 15 carbon atoms, lacking free hydroxyl groups and further lacking acyl or acyl derivatized groups include —CH$_2$—O—CH$_3$, —CH$_2$—O—CH$_2$CH$_3$, —CH$_2$—O—CH$_2$CH$_2$CH$_3$, —CH$_2$—O—CH$_2$CH$_2$—O—CH$_3$, —CH$_2$—O—CH$_2$CH$_2$—O—CH$_2$CH$_3$, —CH$_2$—O—CH$_2$CH$_2$—O—C$_2$CH$_2$—O—CH$_3$, —CH$_2$—CH$_2$—O—CH$_3$, —CH$_2$—CH$_2$—O—CH$_2$CH$_3$, —CH$_2$—O—CH(CH$_2$OCH$_3$)$_2$, —CH$_2$—O—CH(CH$_2$OCH$_2$CH$_3$)$_2$, —CH(CH$_2$OCH$_3$)—O—CH(CH$_2$OCH$_3$)$_2$, and the like.

Examples of oxy-hydrocarbyls having 6 to 30 carbon atoms, at least one aryl or aralkyl group, and only one oxy-group include —CH$_2$—O—C$_6$H$_5$, —CH$_2$—O—CH$_2$C$_6$H$_5$, —CH$_2$—CH$_2$—O—C$_6$H$_5$, —CH$_2$—CH$_2$—O—CH$_2$ C$_6$H$_5$, (methylphenyloxy)methyl (such as (4-methylphenyloxy)methyl and the like), (methylbenzyloxy)methyl (such as (4-methylbenzyloxy) methyl and the like), (methoxyphenyloxy)methyl (such as (4-methoxyphenyloxy)methyl and the like), (methoxybenzyloxy)methyl (such as (4-methoxybenzyloxy) methyl and the like), (tert-butylphenyloxy)methyl (such as (4-tert-butylphenyloxy)methyl and the like), (tert-butylbenzyloxy)methyl (such as (4-butylbenzyloxy)methyl and the like), [(methoxy) (methyl)phenyloxy]methyl (such as (4-methoxy-2-methylphenyloxy)methyl and the like), and [(methoxy)(methyl)benzyloxy] methyl (such as (4-methoxy-2-methylbenzyloxy)methyl and the like).

In a preferred embodiment, the pyrrolo[2,3-d]pyrimidine compound has the following structural characteristics: R$^4$ is —NH$_2$, R$^5$ is —CN, R$^6$ is —H, and R$^7$ is 4-fluorobenzyl or 4-chlorobenzyl or 4-nitrobenzyl. In another preferred embodiment, the pyrrolo[2,3-d]pyrimidine compound has the following structural characteristics: R$^4$ is —NH$_2$, R$^5$ is —CN, R$^6$ is —Br or NH$_2$, and R$^7$ is 4-fluorobenzyl or 4-chlorobenzyl or 4-nitrobenzyl.

In another preferred embodiment, the pyrrolo[2,3-d] pyrimidine compound has the following structural characteristics: R$^4$ is —NH$_2$, R$^5$ is —CN or CSNH$_2$, R$^6$ is —H, or bromo or NH$_2$ and R$^7$ is 2-phenylethyl. In yet another preferred embodiment, the pyrrolo[2,3-d]pyrimidine compound has the following structural characteristics: R$^4$ is —NH$_2$, R$^5$ is —CN or CSNH$_2$, R$^6$ is —H or NH$_2$, and R$^7$ is 3-phenylpropyl.

Compounds of the invention include the following: 4-amino-7-((2-phenyl)eth-2-yl)-pyrrolo[2,3-d]pyrimidine-5-carbonitrile; 4-amino-7-(4-fluorobenzyl)-pyrrolo[2,3-d] pyrimidine-5-carbonitrile; 4-amino-7-(4-chlorobenzyl)-pyrrolo[2,3-d]pyrimidine-5-carbonitrile; 4-amino-7-(4-nitrobenzyl)-pyrrolo[2,3-d]pyrimidine-5-carbonitrile; 4-amino-7-(3-nitrobenzyl)-pyrrolo[2,3-d]pyrimidine-5 -carbonitrile; 4-amino-7-benzyl-pyrrolo[2,3 -d]pyrimidine-5-carboxamide; 4-amino-7-((2-phenyl)-eth-2-yl)-pyrrolo[2,3-d]pyrimidine-5-carboxamide; 4-amino-7-(2-methylbenzyl)-pyrrolo[2,3-d]pyrimidine-5-carboxamide; 4-amino-7-(3-methylbenzyl)-pyrrolo[2,3-d]pyrimidine-5-carboxamide; 4-amino-7-(4-methylbenzyl)-pyrrolo [2,3 -d]pyrimidine-5-carboxamide; 4-amino-7-(4-t-butylbenzyl)-pyrrolo[2,3-d]pyrimidine-5-carboxamide; 4-amino-7-(4-methoxybenzyl)-pyrrolo[2,3-d]pyrimidine-5-carboxamide; 4-amino-7-(4-fluorobenzyl)-pyrrolo[2,3-d] pyrimidine-5-carboxamide; 4-amino-7-(4-nitrobenzyl)-pyrrolo[2,3-d]pyrimidine-5-carboxamide; 4-amino-7-(3-nitrobenzyl)-pyrrolo[2,3-d]pyrimidine-5-carboxamide; 4-oxo-6-bromo-7-(4-methylbenzyl)-pyrrolo[2,3-d] pyrimidine-5-carbonitrile; 4-amino-6-bromo-7-((2-phenyl) eth-2-yl)-pyrrolo[2,3-d]pyrimidine-5-carbonitrile; 4-amino-6-bromo-7-(4-flurobenzyl)-pyrrolo[2,3-d]pyrimidine-5-carbonitrile; 4-amino-6-bromo-7-(4-chlorobenzyl)-pyrrolo [2,3-d]pyrimidine-5-carboxamide; 4-amino-6-bromo-7-(4-chlorobenzyl)-pyrrolo[2,3-d]pyrimidine-5-carbonitrile; 4-amino-6-bromo-7-(3 -chlorobenzyl)-pyrrolo[2,3-d] pyrimidine-5-carbonitrile; 4-amino-6-bromo-7-(3,4-dichlorobenzyl)-pyrrolo[2,3-d]pyrimidine-5-carbonitrile; 4-amino-6-bromo-7-(4-bromobenzyl)-pyrrolo[2,3-d] pyrimidine-5-carbonitrile; 4-amino-6-bromo-7-(4-nitrobenzyl)-pyrrolo[2,3-d]pyrimidine-5-carbonitrile; 4-amino-6-bromo-7-(3-nitrobenzyl)-pyrrolo[2,3-d] pyrimidine-5-carbonitrile; 4-amino-6-bromo-7-(4-methylbenzyl)-pyrrolo[2,3-d]pyrimidine-5-carboxamide; 4-6-diamino-7-((2-phenyl)eth-2-yl)-pyrrolo [2,3-d] pyrimidine-5-carbonitrile; 4,6-diamino-7-(4-flourobenzyl)-pyrrolo[2,3-d]pyrimidine-5-carbonitrile; 4,6-diamino-7-(4-chlorobenzyl)-pyrrolo[2,3-d]pyrimidine-5-carbonitrile; 4,6-diamino-7-(4-bromobenzyl)-pyrrolo[2,3-d]pyrimidine-5-carbonitrile; 4,6-diamino-7-(4-nitrobenzyl)-pyrrolo[2,3-d] pyrimidine-5-carbonitrile; 4,6-diamino-7-(4-aminobenzyl)-pyrrolo[2,3-d]pyrimidine-5-carbonitrile; 4,6-diamino-7-(3-nitrobenzyl)-pyrrolo[2,3-d]pyrimidine-5-carbonitrile; 4,6-diamino-7-(3-aminobenzyl)-pyrrolo[2,3-d]pyrimidine-5-carbonitrile; 4-amino-7-(2-phenyl)ethyl-pyrrolo[2,3-d] pyrimidine-5-carbonitrile; 4-amino-7-(2-phenyl)ethyl-pyrrolo[2,3-d]pyrimidine-5-carboxamide; 4-amino-7-(2-phenyl)ethyl-pyrrolo[2,3 -d]pyrimidine-5-thiocarboxamide; 4-methylamino-6-bromo-7-(2-phenyl)ethyl-pyrrolo[2,3-d] pyrimidine-5-carbonitrile; 4-amino-6-bromo-7-(2-phenyl) ethyl-pyrrolo[2,3-d]pyrimidine-5-carbonitrile; 4-amino-6-bromo-7-(2-phenyl)ethyl-pyrrolo[2,3-d]pyrimidine-5-carboxamide; 4,6-diamino-7-(2-phenyl)ethyl-pyrrolo[2,3-d] pyrimidine-5-carbonitrile;4-amino-7-(3-phenyl)propyl-pyrrolo[2,3-d]pyrimidine-5-thiocarboxamide; 4-amino-7-(3-phenyl)propyl-pyrrolo[2,3-d]pyrimidine-5-carboxamide; 4-amino-7-(3-phenyl)propyl-pyrrolo[2,3-d]pyrimidine-5-carbonitrile; 4-amino-6-bromo-7-(3-phenyl)propyl-pyrrolo [2,3-d]pyrimidine-5-carbonitrile; 4,6-diamino-7-(3-phenyl)

propyl-pyrrolo[2,3-d]pyrimidine-5-carbonitrile; 4-amino-6-bromo-7-(3-phenyl)prop-2-enyl-pyrrolo[2,3-d]pyrimidine-5-carbonitrile; 4-amino-7-(3-phenyl)prop-2-enyl-pyrrolo[2,3-d]pyrimidine-5-carbonitrile; and 4,6-diamino-7-(3-phenyl)prop-2-enyl-pyrrolo[2,3-d]pyrimidine-5-carbonitrile.

B. Formulation and Use of Compounds

The compounds of the present invention exhibit superior antiviral activity and acceptable cytotoxicity for use as therapeutic agents for preventing or treating viral infections. In particular, it has been found that these compounds are effective against HCMV and HSV-1 viruses.

Prior studies indicated that a certain 4-amino-7-[(2-methoxyethoxy)methyl]pyrrolo[2,3-d]pyrimidine-5-thiocarboxamide (a compound disclosd as compound 5b in the U.S. Pat. No. 5,543,413) inhibited HCMV and HSV-1 viral replication by a mechanism other than through inhibition of DNA synthesis because the inhibition was shown to occur through a mechanism early in the replication cycle. Accordingly, it is expected that compounds of the present invention can be effective against RNA viruses such as hepatitis B and hepatitis C as well.

A partial list of mammalian viruses contemplated to be treatable with the compounds of the present invention includes: herpes simplex virus types 1 and 2; human cytomegalovirus; human immunodeficiency virus; human herpesvirus 6 (HHV6); varicella-zoster virus; Epstein-Barr virus (EBV); herpesvirus simiae; equine herpesvirus-1, 2 and 3; neurolymphomatosis (Marek's disease); influenza viruses A, B and C; parainfluenza viruses-1,2,3 and 4; adenovirus; reovirus; respiratory syncytial virus; rhinovirus; coxsackle virus; echo virus; rubeola virus; hepatitis viruses of the types B and C; and papovavirus.

Members of the herpesvirus family (Herpesviridae) share a common virion architecture. A typical herpesvirion consists of (a) a core containing a linear, double-stranded DNA, (b) an icosahedral capsid, approximately 100–120 nm in diameter, containing 162 capsomeres, (c) an amorphous, sometimes asymmetric material that surrounds the capsid, designated as the tegument, and (d) an envelope containing viral glycoprotein spikes on its surface.

Major examples of human pathogens of the herpesviruses family include herpes simplex viruses (HSV) 1, 2, and cercopithecine herpesvirus 1 (B-virus); varicella-zoster (which causes chickenpox and shingles); Epstein-Barr virus (EBV, which causes mononucleosis); lymphocryptovirus; human herpesvirus 6 (HHV6); human herpesvirus 7 (HHV7) and kaposi-associated herpes virus (KHV); or human herpesvirus 8 (HHV8). Human cytomegalovirus (HCMV), also a human herpes virus, is a leading opportunistic pathogen among immunosuppressed individuals (see Alford, C. A.; Britt, W. J. Cytomegalovirus. In *The Human Herpesviruses*. Roizman, B.; Whitley, R. J.; Lopez, C. (Editors.) Raven Press, New York, 1993 pp. 227–255) and neonates (see Alford, C. A. et al., *Rev. Infect. Dis.* 1990, 12, s793–s804 and Gallant, J. E. et al., *J. Infect. Dis.* 1992, 166, 1223–1227).

Animal pathogens include infectious bovine rhinotracheitis virus, bovine mammillitis virus, cercopithecine herpesvirus 1 (B-virus), which are all simplexviruses; pseudorabies virus (PRV, of swine), equine rhinopneumonitis and coital exanthema viruses (varicellaviruses); baboon herpesvirus, pongine (chimpanzee) herpesvirus (lymphocryptovirus); Marek's disease virus (of fowl), turkey herpesvirus; herpesvirus ateles and herpesvirus saimiri (rhadinovirus); among others. For reviews see, Murphy et al., Virus Taxonomy, in Fields et al. (eds.) Fundamental Virology, 1991. Raven Press, New York, p. 9–36; Watson et al., Molecular Biology of the Gene, Fourth Edition, 1987, Benjamin/Cummings Publ. Co., Menlo Park, Calif, p. 904, 933.

Herpesvirus genomes, which are generally 120 to 230 kb long, encode 50 to 200 different proteins. These include a large array of enzymes involved in nucleic acid metabolism (e.g., thymidine kinase, thymidylate synthetase, dUTPase, ribonucleotide reductase, etc.), and DNA synthesis (e.g., DNA polymerase, helicase, primase).

Some herpesviruses such as HSV-1 and HSV-2 have a wide host-cell range, multiply efficiently and rapidly destroy infected cells. Others (e.g. EBV, HHV6) have a narrow host-cell range or, in the case of HCMV, replicate slowly. For reviews see, Roizman et al., Herpes Simplex Viruses and Their Replication, in Fields et al. (eds.) Fundamental Virology, 1991, Raven Press, New York, p. 849–895.

Herpesviruses replicate in the cell nucleus, wherein the nucleolus is displaced, disaggregated and then fragmented, and host chromosomes are marginated, which may lead to chromosome breakage. Host protein synthesis declines very rapidly (for most herpesviruses but not HCMV), host ribosomal RNA synthesis is reduced, and glycosylation of host proteins ceases. Production of progeny is invariably accompanied by the irreversible destruction of the infected cell. For reviews see, Roizman et al., Herpes Simplex Viruses and Their Replication, in Fields et al. (eds.) Fundamental Virology, 1991, Raven Press, New York, p. 849–895.

A variety of disease symptoms and a complex clinical course are caused by herpesviruses. In the case of a first infection in an adult human, the symptoms may be very severe. Herpesviruses can cause recurrent infections, and the disability associated with these recurrences is a significant health problem. The most frequent manifestations of recurrent herpetic disease states were disclosed to involve the orofacial and genital regions and recurrent herpetic keratitis was characterized as a leading cause of blindness in the United States. Herpetic genital infections with a high incidence of subsequent recurrent episodes were noted as being recognized more frequently and being associated with significant morbidity. Cohen et al., U.S. Pat. No. 4,709,011, issued Nov. 24, 1987.

In the case of EBV and HCMV, acute hepatitis is frequently associated with infectious mononucleosis. Mononuclear cells are the major candidate as cells involved in the latent state of HCMV infection, and infectious mononucleosis may follow blood transfusions from seropositive to seronegative individuals. Seronegative individuals may also become infected via transplantation of cells or organs from seropositive donors. For reviews see, Ahmed et al., Viral Persistence, in Fields et al. (eds.) Fundamental Virology, 1991, Raven Press, New York, p. 241–265; Stinski, Cytomegalovirus and Its Replication, in Fields et al. (eds.) Fundamental Virology, 1991, Raven Press, New York, p. 929–950.

A herpesvirus of economic importance in the cattle industry is Bovine Herpesvirus-1 (BHV-1), which has been associated with a variety of clinical disease manifestations, including rhinotracheitis, vulvovaginitis, abortions, conjunctivitis, encephalitis and generalized systemic infections. Gibbs et al., 1977, Bovine herpesviruses. I: Bovine herpesvirus-1. *Vet. Bull.* (*London*) 47: 317–343.

The herpesvirus Pseudorabies virus (PRV), also called Aujeszky's disease virus (ADV), is a disease of all domestic animals, with the exception of the horse, and causes severe damage, especially among pigs and cattle. The pig is the natural host of ADV. Animals are infected via the nasal route and, after a primary virus multiplication in the mucous membranes of upper respiratory and digestive tracts, the virus spreads via nerves to the brain. The infection proceeds acutely to sub-clinically, which is mainly dependent on the virulence of the virus and the age of the pigs. PRV, just as other herpesviruses induces latent infections, namely in the nerve tissues. Bems et al., U.S. Pat. No. 4,680,176, issued Jul. 14, 1987.

Currently, only three drugs have been FDA-approved for the treatment of HCMV infections: gancyclovir (see Crumpacker, C. S. Ganciclovir. *New England J. Med.* 1996, 335, 721–729), foscaret (see Chrisp, P.; Clissold, S. P. Foscarnet. A Review of its Antiviral Activity, Pharmacokinetic Properties and Therapeutic Use in Immunocompromised Patients with Cytomegalovirus Retinitis. *Drugs* 1991, 41, 104–129), and cidofivir (see Hitchcock, M. J. et al., *Antiviral Chem. & Chemother.* 1996; 7: 115–127; Lalezari, J. P. et al., *J. Infect. Dis.* 1995, 171, 788–796.). All of these drugs can lead to side-effects such as renal dysfunction (foscarnet and cidofivir) and granulocytopenia (ganciclovir). Additionally, potential drug resistance and poor oral bioavailability create a need for more potent and selective drugs (see Field, A. K.; Biron, K. K. "The End of Innocence" Revisited: Resistance of Herpesviruses to Antiviral Drugs. *Clin. Microbiol. Rev.* 1994, 7, 1–13).

The hepatitis B virus (HBV) infects hepatocytes and causes acute and chronic liver disease and hepatocellular carcinoma. Infection is typically via contaminated blood or body fluids, and thus HBV infection is prevalent among intravenous drug abusers, homosexuals, and in countries with less developed health care systems where the risk of exposure to contaminated blood products is high. Approximately 90–95% of infected individuals are able to resolve their infection, while the remaining 5–10% develop chronic hepatitis and lapse into a carrier state, with the possibility of later developing liver cirrhosis and/or hepatocellular carcinoma. It has recently been estimated that throughout the world there are approximately 250 million people who are chronic carriers of HBV.

The pathogenic mechanisms responsible for liver cell injury in HBV infection are not well understood, although it is believed that the virus is not directly cytopathic. Since HBV does not readily infect human cells in vitro, however, the virus has been extremely difficult to study. Consequently, as yet there is no effective treatment for an established HBV infection.

Hepatitis C, which is neither hepatitis A nor hepatitis B, forms 95 to 100% of post-transfusion hepatitis and 40 to 50% of sporadic hepatitis and easily becomes chronic, further changing at high rates to cancer of liver via chronic hepatitis or hepatic cirrhosis. Recently, hepatitis C virus (HCV) was identified, and it has been demonstrated that most of hepatitis previously known as non-hepatitis A or non-hepatitis B are caused by this hepatitis C virus.

Although interferon has been known as an agent having inhibitory effect on the proliferation of hepatitis C virus, it is pointed out that there are problems such as its low rate in the effectiveness as little as 30 to 40%, the 60 to 70% recrudescence after discontinuance of the dosage thereof, the appearance of influenza-like symptoms, such as pyrexia, headache and vomiting, and of diverse side effects such as leukopenia, at the high rates. Accordingly, there exists currently no effective treatment or preventive with acceptable efficacy and toxicity profile.

In this regard it will also be appreciated that "treatment" in accordance with the present invention encompasses the treatment of viral infections, as well as prophylactic treatment of patients who are at risk for viral infection, e.g. immuno-compromised patients, such as bone marrow transplant patients.

The term "pharmaceutically acceptable salt, prodrug or derivative," as used herein, related to any pharmaceutically acceptable salt, ester, ether, salt of an ester, solvate, such as ethanolate, or other derivative of a compound of the present invention which, upon administration to a recipient, is capable of providing (directly or indirectly) a compound of this invention or an active metabolite or residue thereof. Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system).

Salts of the compounds of the present invention may be derived from inorganic or organic acids and bases. Examples of acids include hydrochloric, hydrobromic, sulfuric, nitric, perchloric, fumaric, maleic, phosphoric, glycollic, lactic, salicyclic, succinic, toluene-p-sulfonic, tartaric, acetic, citric, methanesulfonic, ethanesulfonic, formic, benzoic, malonic, naphthalene-2-sulfonic and benzenesulfonic acids. Other acids, such as oxalic, while not in themselves pharmaceutically acceptable, may be employed in the preparation of salts useful as intermediates in obtaining the compounds of the invention and their pharmaceutically acceptable acid addition salts. Examples of bases include alkali metal (e.g., sodium) hydroxides, alkaline earth metal (e.g., magnesium) hydroxides, ammonia, and compounds of formula $NW_4^+$, wherein W is $C_{1-4}$ alkyl.

Examples of salts include: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylproprionate, picrate, pivalate. propionate, succinate, tartrate, thiocyanate, tosylate and undecanoate. Other examples of salts include anions of the compounds of the present invention compounded with a suitable cation such as $Na^+$, $NH_4^+$, and $NW_4^+$ (wherein W is a $C_{1-4}$ alkyl group).

For therapeutic use, salts of the compounds of the present invention will be pharmaceutically acceptable. However, salts of acids and bases which are non-pharmaceutically acceptable may also find use, for example, in the preparation or purification of a pharmaceutically acceptable compound.

Esters of the compounds of the present invention include carboxylic acid esters (i e., —O—C(=O)R) obtained by esterification of the 2'-, 3'- and/or 5'-hydroxy groups, in which R is selected from (1) straight or branched chain alkyl (for example, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted by, for example, halogen, $C_{1-4}$alkyl, or $C_{1-4}$alkoxy or amino); (2) sulfonate esters, such as alkylsulfonyl (for example, methanesulfonyl) or aralkylsulfonyl; (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di-($C_{6-24}$)acyl glycerol. In such esters, unless otherwise specified, any alkyl moiety present advantageously-contains from 1 to 18 carbon atoms, particularly from 1 to 6 carbon atoms, more particularly from 1 to 4 carbon atoms, Any cycloalkyl moiety present in such esters advantageously contains from 3 to 6 carbon atoms. Any aryl moiety present in such esters advantageously comprises a phenyl group. Examples of prodrug derivatives of the present invention include, for example, those with chemically protected hydroxyl groups (e.g., with O-acetyl groups).

Ethers of the compounds of the present invention include methyl, ethyl, propyl, butyl, isobutyl, and sec-butyl ethers.

One aspect of the present invention pertains to methods for inhibiting viral replication and/or propagation in vitro, ex vivo or in vivo, by contacting the virus with an effective amount of a compound effective to inhibit viral replication and/or propagation. When the contacting is done in vitro, the compounds are useful to screen for other antiviral compounds that may be used independently or in combination with the compounds disclosed herein. The compounds also are useful for treating and/or preventing a viral infection by administering to an infected host a therapeutically effective amount of a pyrrolo[2,3-d]pyrimidine compound of the present invention. In one embodiment, such methods include administering to an infected host a composition of a pharmaceutically acceptable carrier and a therapeutically effective amount of an antiviral pyrrolo[2,3-d]pyrimidine compound of the present invention.

The term "effective amount" is to include a prophylactically effective amount and refers to an amount effective in treating or preventing a viral infection in a patient either as monotherapy or in combination with other agents. The term "treating" as used herein refers to the alleviation of symptoms of a particular disorder in a patient or the improvement of an ascertainable measurement associated with a particular disorder or a reduction in viral titer in the host. One of skill in the art can determine when a host has been "treated" by noting a reduction in viral load or an alleviation in symptoms associated with viral infection. The term "prophylactically effective amount" refers to an amount effective in preventing viral infection in a host. As used herein, the term "host" refers to a mammal, such as a mouse, bovine, rat or a human patient.

The term "biologically acceptable carrier" refers to a carrier or adjuvant that may be administered to a host or patient, together with a compound of this invention, and which does not destroy the pharmacological activity thereof and is nontoxic when administered in doses sufficient to deliver an effective amount of the antiviral compound. Examples of suitable carriers include liquid phase carriers, such as sterile or aqueous solutions, as well as those described below.

As shown below, the compounds of this invention are potent antiviral drugs and as such, when combined with carriers, provide compositions for inhibiting viral reproduction and proliferation in vitro, ex vivo or in vivo. However, it should be understood, although not explicitly stated, that other virus, such as HHV-6 and HIV can be inhibited by the compounds of this invention. Methods of determining efficacy against these viruses are provided below. In addition RNA virus can be inhibited by the compounds of this invention.

The compounds of this invention also can be employed in combination with other therapeutic agents for the inhibition of the replication or propagation of the above virus and associated conditions. Combination therapies according to the present invention comprise the administration of at least one compound of the present invention and at least one other pharmaceutically active ingredient. The active ingredient(s) and pharmaceutically active agents may be administered simultaneously in either the same or different pharmaceutical formulations or sequentially in any order. The amounts of the active ingredient(s) and pharmaceutically active agent (s) and the relative timings of administration will be selected in order to achieve the desired combined therapeutic effect. Preferably the combination therapy involves the administration of one compound according to the invention and one of the agents mentioned herein below. The term "operative combination" is intended to include any chemically compatible combination of a compound of the present invention with other compounds of the present invention or other compounds outside the present invention (such as ganciclovir, AZT, and foscarnet), as long as the combination does not eliminate the antiviral activity of the compound of the present invention.

Examples of other active ingredients include agents that are effective for the treatment of viral infections or associated conditions are (1-alpha, 2-beta, 3-alpha)-9-[2,3-bis (hydroxymethyl)cyclobutyl]guanine[(−)BHCG, SQ-34514], oxetanocin-G(3,4-bis-(hydroxymethyl)-2-oxetanosyl] guanine), acyclic nucleosides (e.g., acyclovir, valaciclovir, famciclovir, ganciclovir, penciclovir), acyclic nucleoside phosphonates (e.g., (S)-1-(3-hydroxy-2-phosphonylmethoxypropyl)cytosine (HPMPC), ribonucleotide reductase inhibitors such as 2-acetylpyridine 5-[(2-chloroanilino)thiocarbonyl] thiocarbonohydrazone, 3'-azido-3'-deoxythymidine, other 2',3'-dideoxynucleosides such as 2',3'-dideoxycytidine, 2',3'-dideoxyadenosine, 2',3'-dideoxyinosine, 2',3'-didehydrothymidine, protease inhibitors such as ritonovir, indinavir, 141W94, nelfinavir, sanquinavir, and 3S-[3R*(1S*,2R*)]-[3-[[(4-aminophenyl) sulphonyl](2-methylpropyl)-amino]-2hydroxy-1-phenylmethyl)propyl]carbamic acid, tetrahydro-3-furanyl ester (141W94), oxathiolane nucleoside analogues such as (−)-cis-1-(2-hydroxymethyl)-1,3-oxathiolane-5-yl)-cytosine (lamivudine) or cis-1-(2-(hydroxymethyl)-1,3-oxathiolan-5-yl)-5-fluorocytosine (FTC), 3'-deoxy-3'-fluorothymidine, 5-chloro-2',3'-dideoxy-3'-fluorouridine, (−)-cis-4-[2-amino-6(cyclopropylamino)-9H-purin-9-yl]-2-cyclopentene-1-methanol, ribavirin, 9-[4-hydroxy-2-(hydroxymethyl)but-1-yl]-guanine (H2G), tat inhibitors such as 7-chloro-5-(2-pyrryl)-3H-1,4-benzodiazepin-2-(H)one (Ro5-3335), 7-chloro-1,3-dihydro-5-(1H-pyrrol-2-yl)-3H-1,4-benzodiazepin-2-amine (Ro24-7429), interferons such as (α-interferon, renal excretion inhibitors such as probenecid, nucleoside transport inhibitors such as dipyridamole; pentoxifylline, N-acetylcysteine (NAC), Procysteine, (α-trichosanthin, phosphonoformic acid, as well as immunomodulators such as interleukin II or thymosin, granulocyte macrophage colony stimulating factors, erythropoetin, soluble $CD_4$ and genetically engineered derivatives thereof, or non-nucleoside reverse transcriptase inhibitors such as nevirapine (BI-RG-587), loviride (α-APA) and delavuridine (BHAP), and phosphonoformic acid.

The compounds of the invention could also be used to treat HCMV and HSV-1 infections in AIDS patients already receiving the antiviral drug zidovudine (AZT) and/or 3TC. Combination therapies with AZT may provide the advantage of less toxicity over the combination of ganciclovir with AZT. The combination of the compounds of this invention with AZT may produce less cytotoxicity (ie. antagonism) in cultured human cells than either agent used alone. In contrast, combination of ganciclovir with AZT may produce greater cytotoxicity in human cells than the use of either of those drugs alone.

For the purposes of this invention, a "cell" is intended to include, but not be limited to a mammalian cell, e.g., a mouse cell, a bovine cell, a rat cell, a woodchuck cell, a simian cell, or a human cell. Viruses which are effectively treated by the compounds, compositions and methods of this invention include DNA and RNA viruses, particularly herpes-type viruses. Examples of herpes-type viruses, or herpesviridae, are herpes simplex virus 1 (HSV-1), herpes simplex virus 2 (HSV-2), varicella-zoster virus (VZV), Epstein-Barr virus (EBV), human cytomegalovirus (HCMV), human herpes virus 6 (HHV-6), human herpes virus 7 (HHV-7), and human herpes virus 8 (HHV-8). The compounds of the present invention are particularly useful in the treatment of HCMV and HSV-1 infections, and associated pathologies such as restenosis. They also are suitably used in the treatment of hepatitis associated disorders such as hepatocellular carcinoma (See, U.S. Pat. No. 5,679,342).

Effective amounts are easily determined by those of skill in the art and will vary with the cell, virus being effected and the purpose of the treatment. For example, when utilizing the drug in cell culture, it is important that the amount of drug not be cytotoxic to the cells.

"Suitable conditions" include in vitro, ex vivo or in vivo. When the method is practiced in vitro, contacting may be effected by incubating the cells with an effective antiviral amount of the compound, effective to inhibit viral reproduction and proliferation in the cell or culture of cells. The compound can be added directly to the culture media or combined with a carrier prior to addition to the cells. In vitro, the method is particularly useful for inhibiting viral reproduction, proliferation and therefore infection in laboratory cell cultures. Ex vivo, the compounds are useful to inhibit viral reproduction and proliferation in blood and plasma prior to reintroduction into a patient.

The use of the compounds and methods in vitro also provides a powerful bioassay to screen for novel drugs or compounds which provide similar or enhanced antiviral activity. Using the methods set forth below, the drug to be tested is assayed under the same conditions as a compound of this invention. Antiviral and cytotoxicity of the test drug can then be compared to a compound of this inventive group.

Although the compounds are shown below to be particularly effective against HCMV and HSV-1, it is within the scope of this invention that other viruses are effectively treated with the compounds of this invention by use of methods described herein and others well known to those of skill in the art. Other viruses that can be treated as defined herein and within the scope of the present invention include all members of the herpes family, and human immunodeficiency virus (HIV) and hepatitis viruses, for example, hepatitis B virus (HBV). Methods of determining the efficiency of any of the compounds of this invention against HBV are well known in the art; see for example, the methods shown in U.S. Pat. No. 5,399,580 to Daluge.

An additional member of the hepatitis virus family that can be treated as defined herein is hepatitis C virus (HCV). U.S. Pat. No. 5,679,342, issued to Houghton et al. describes in detail methods for employing an extracorporeal cell system infected with HCV to screen for the compounds most active against HCV. In brief, the method comprises: (a) providing a composition containing the compound of this invention to be tested; (b) providing an extracorporeal cell system capable of being infected by HCV; (c) providing a biological sample containing infective HCV; (d) incubating the compositions of (a) and (c) with the cell system of (b) under conditions that would, in the absence of (a), allow infection of HCV in the cell system; and (e) detecting inhibition of viral infection after incubation. Preferred cell systems as disclosed in U.S. Pat. No. 5,679,342, include hepatocytes, macrophages, more preferably Kupffer macrophages, and B lymphocytes. Cell lines derived from organs of hepatocytic origin also are suitable for use in the assay described above. One can also use the above noted assay to test for the inhibition of viral replication by incubating the compositions of (a) and (b) under conditions that would, in the absence of (a), allow replication of HCV in the cell line and then detecting inhibition of viral replication after incubation.

Another method well known in the art for testing the antiviral activity of compounds against HCV is the helicase inhibition assay described, for example, in Lain et al., (1991) *Nucleic Acids Res.* 69:1720–1726 and Kim et al., (1995) *Biochem. Biophys, Res. Comm.* 160–166.

When the method is practiced in vivo in a subject such as a human patient, the compound can be added to a pharmaceutically acceptable carrier and systemically or topically administered to the subject, such as a human patient or a mammal such as a mouse, a rat, a woodchuck, or a simian.

It should be understood that by preventing or inhibiting viral proliferation, infection and replication in a subject or individual, the compositions and methods of this invention also provide methods for treating, preventing or ameliorating the symptoms or disorders associated with the viral infection, such as inclusion disease, blindness. mononucleosis, restenosis (HCMV); chickenpox, shingles (varicella-zoster virus); infectious mononucleosis, glandular, fever, and Burkittis lymphoma (Epstein-Barr virus); cold sores (herpes simplex virus 1); genital herpes (herpes simplex virus 2); roseola infantum (human herpes virus 6, human herpes virus 7); kaposi sarcoma (human herpes virus 8). Thus, this invention also provides methods of ameliorating, preventing, or treating disorders or symptoms associated with viral infection, e.g., HCMV, HSV-1 and herpes viral infection, e.g., restenosis, opportunistic infections (such as retinal infections, gastrointestinal infections, pneumonia, CNS infections or liver damage) and in utero infections, by administering to the subject an effective amount of a compound of this invention under suitable conditions such that the disorder or symptom is ameliorated, prevented, or treated.

Restenosis is the narrowing of the blood vessels which can occur after injury to the vessel wall, for example injury caused by balloon angioplasty or other surgical techniques, and is characterized by excessive proliferation of smooth muscle cells in the walls of the blood vessel treated. Restenosis following angioplasty (RFA) occurs in patients who have been treated for coronary artery disease by balloon angioplasty It is thought that in many patients suffering from RFA, viral infection, particularly by CMV and/or HHV-6, of the patient plays a pivotal role in the proliferation of the smooth muscle cells in the coronary vessel treated. Thus, the compounds of this invention can be used in methods to prevent or treat restenosis in a susceptible subject or patient Administration in vivo can be effected in one dose, continuously or intermittently throughout the course of treatment. Methods of determining the most effective means and dosage of administration are well known to those of skill in the art and will vary with the composition used for therapy, the target virus, the purpose of the therapy, the target cell being treated, and the subject being treated. Single or multiple administrations can be carried out with the dose level and pattern being selected by the treating physician. Suitable dosage formulations and methods of administering the compounds can be found below.

The compounds of the present invention all exhibit antiviral activity against HCMV, herpes viral infection and HSV-1, many with acceptable cytotoxicity. It will be appreciated that compounds of the present invention which exhibit relatively high antiviral activity versus cytotoxicity, i.e. good selectivity, are preferred. It will also be appreciated that antiviral treatment in accordance with the present invention encompasses the treatment of viral infections, as well as prophylactic treatment which may be desired in certain situations, e.g. in immunocompromised patients, such as bone marrow and organ transplant patients as well as patients harboring HIV who are particularly susceptible to HCMV, herpes viral, or HSV-1 infection.

The compounds and compositions of the present invention can be used in the manufacture of medicaments and in antiviral treatment of humans and other animals by administration in accordance with conventional procedures, such as an active ingredient in pharmaceutical compositions. Techniques and formulations may be found, for example, in Remmington's Pharmaceutical Sciences, Mack Publishing Co., Easton, Pa. (latest edition).

In general a suitable dose for each of the above-named viral infections, is in the range of about 0.1 to about 250 mg per kilogram body weight of the recipient per day, preferably in the range of about I to 100 mg per kilogram body weight per day and most preferably in the range of about 5 to about 20 mg per kilogram body weight per day. Unless otherwise indicated, all weights of active ingredient are calculated as the parent compound of the formula of the present invention; for salts or esters thereof, the weights would be increased proportionately. The desired dose is preferably presented as two, three, four, five, six or more sub-doses administered at appropriate intervals throughout the day. These sub-doses may be administered in unit dosage forms, for example, containing about 10 to about 1000 mg, preferably about 20 to about 500 mg, and most preferably about 100 to about 400 mg of active ingredient per unit dosage form. It will be appreciated that appropriate dosages of the compounds and compositions of the invention may depend on the type and severity of the viral infection and can vary from patient to patient. Determining the optimal dosage will generally involve the balancing of the level of therapeutic benefit against any risk or deleterious side effects of the antiviral treatments of the present invention.

Ideally, the active ingredient should be administered to achieve peak plasma concentrations of the active compound of from about 0.25 to about 100 uM, preferably about 0.5 to about 70 uM, most preferably about 1 to about 50 uM. This may be achieved, for example, by the intravenous injection of about 0.1 to about 5% solution of the active ingredient, optionally in saline, or orally administered, for example, as a tablet, capsule or syrup containing about 0.1 to about 250 mg per kilogram of the active ingredient. Desirable blood levels may be maintained by a continuous infusion to provide about 0.01 to about 5.0 mg/kg/hour or by intermittent infusions containing about 0.4 to about 15 mg per kilogram of the active ingredient.

While it is possible for the active ingredient to be administered alone, it is preferable to present it as a pharmaceutical formulation comprising at least one active ingredient, as defined above, together with one or more pharmaceutically acceptable carriers, such as diluents or excipients which may include, for example, fillers, extenders, wetting agents, disintegrants, surface-active agents, or lubricants, depending on the nature and mode of administration and the dosage forms. Each carrier must be "acceptable" in the sense of being compatible with the other ingredients of the formulation and not injurious to the patient. The pharmaceutical formulation may optionally include other therapeutic agents.

Formulations include those suitable for oral, rectal, nasal, topical (including transdermal, buccal and sublingual), vaginal, parenteral (including subcutaneous, intramuscular, intravenous and intradermal) and pulmonary administration. The formulations may conveniently be presented in unit dosage form and may be prepared by any methods well known in the art of pharmacy. Such methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then if necessary shaping the product.

Formulations of the present invention suitable for oral administration may be presented as discrete units such as capsules, cachets or tablets, each containing a predetermined amount of the active ingredient; as a powder or granules; as a solution or suspension in an aqueous or nonaqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface-active or dispersing agent. Molded tablets may be made by molding in a suitable machine a mixture of the powdered compound moistened with an inert liquid diluent. The tablets may optionally be coated or scored and may be formulated so as to provide; slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions for topical administration according to the present invention may be formulated as an ointment, cream, suspension, lotion, powder, solution, paste, gel, spray, aerosol or oil. Alternatively, a formulation may comprise a patch or a dressing such as a bandage or adhesive plaster impregnated with active ingredients and optionally one or more excipients or diluents.

The active compound can be provided in the form of pharmaceutically acceptable salts. As used herein, the term pharmaceutically acceptable salts or complexes refers to salts or complexes of the nucleosides that retain the desired biological activity of the parent compound and exhibit minimal, if any, undesired toxicological effects. Nonlimiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acids, naphthalenedisulfonic acids, and polygalacturonic acid; (b) base addition salts formed with cations such as sodium, potassium, zinc, calcium, bismuth, barium, magnesium, aluminum, copper, cobalt, nickel, cadmium, sodium, potassium, and the like, or with an organic cation formed from N,N-dibenzylethylenediamine, ammonium, or ethylenediamine; or (c) combinations of (a) and (b); e.g., a zinc tannate salt or the like.

The active compound, or pharmaceutically acceptable derivative or salt thereof can also be mixed with other active materials that do not impair the desired action, or with materials that supplement the desired action, such as antibiotics, antifungals, antiinflammatories, or other antivirals, including anti-HBV or anti-HIV agents.

For infections of the eye or other external tissues, e.g., mouth and skin. the formulations are preferably applied as a topical ointment or cream containing the active ingredient in an amount of, for example, about 0.075 to about 20% w/w, preferably about 0.2 to about 25% w/w and most preferably about 0.5 to about 10% w/w. When formulated in an ointment, the active ingredient may be, employed with either a paraffinic or a water-miscible ointment base. Alternatively, the active ingredients may be formulated in a cream with an oil-in-water cream base.

If desired, the aqueous phase of the cream base may include, for example, at least about 30% w/w of a polyhydric alcohol, Le., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active ingredient through the skin or other affected areas. Examples of such dermal penetration enhances include dimethylsulfoxide and related analogues.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Emulgents and emulsion stabilizers suitable for use in the formation of the present invention include Tween 60, Span 80, cetostearyl alcohol, myristyl alcohol, glyceryl monostearate and sodium lauryl sulphate.

The choice of suitable oils or fats for the formation is based on achieving the desired cosmetic; properties, since the solubility of the active compound in most oils likely to be used in pharmaceutical emulsion formulations is very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the active ingredient. The active ingredient is preferably present in such formulation in a concentration of about 0.5 to about 20% advantageously about 0.5 to about 10% particularly about 1.5% w/v.

Formulations for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active ingredient, such carriers as are known in the art to be appropriate.

Formulations suitable for nasal administration, wherein the carrier is a solid, include a coarse powder having a particle size, for example, in the range of about 20 to about 500 microns which is administered in the manner in which snuff is taken, i.e., by rapid inhalation through the nasal passage from a container of the powder held close up to the nose. Suitable formulations wherein the carrier is a liquid for administration as, for example, a nasal spray or a nasal drops, include aqueous or oily solutions of the active ingredient.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. The formulations may be presented in unit-dose or multi-dose sealed containers, for example, ampoules and vials, and may be stored in a freeze-dried (lyophilized) condition requiring only the addition of the sterile liquid carrier, for example water or injections, immediately prior to use. Extemporaneous injection solutions and suspensions may be prepared from sterile powders, granules and tablets of the kind previously described.

Preferred unit dosage formulations are those containing a daily dose or unit, daily subdose, as herein above-recited, or an appropriate fraction thereof, of an active ingredient.

It should be understood that in addition to the ingredients particularly mentioned above, the formulations of this invention may include other agents conventional in the art having regard to the type of formulation in question, for example, those suitable or oral administration may include such further agents as sweeteners, thickeners and flavoring agents.

Compounds of the formula of the present may also be presented for the use in the form of veterinary formulations, which may be prepared, for example, by methods that are conventional in the art.

C. Synthesis of Compounds

The following equipment, solvents, chemicals, and analytical methodology were employed in preparing the compounds of the present invention. $^1$H NMR spectra were recorded on a Bruker 300 or 500 MHz spectrometer with dmso-$d_6$ and CDCl$_3$, as solvents. Chemical shifts were reported in δ values (ppm) relative to the internal standard tetramethylsilane (TMS). Elemental analyses were performed by analytical services, department of chemistry, The University of Michigan. Melting points were taken on a Laboratory Device capillary melting point apparatus and are uncorrected. Thin-layer chromatography (TLC) was run on silica gel 60F-254 plates (Analtech, Inc.). Detection of components on TLC was made by UV light absorption at 254 nm. Silica gel(230–400 mesh) that was used for flash chromatography was obtained from Lagand Chemical Company, Inc. Evaporations were carried out on a rotary evaporator under reduced pressure (water aspirator) with the varying bath temperatures. Dry solvents were obtained from stills. THF was dried over sodium and acetonitrile was dried over calcium hydride. Yields were not optimized.

1. General Synthetic Methods

The compounds of the present invention can be synthesized in accordance with the procedures described below.

a. General procedure to prepare 7-alkylated-4-amino-6-bromo-5-cyanopyrrolo[2,3-d]pyrimidines (6)

The general procedure to prepare 7-alkylated-4-amino-6-bromo-5-cyanopyrrolo[2,3-d]pyrimidines (6) from tetracyanoethylene is illustrated in Scheme 1 as below.

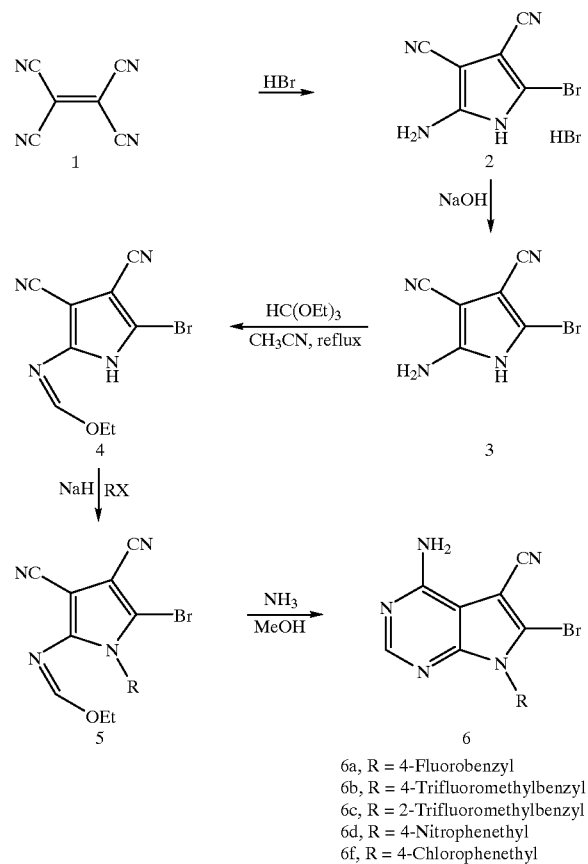

Tetracyanoethylene (1) is reacted with HBr followed by treatment with a base such as NaOH produced 2-amino-5-bromo-3,4-dicyanopyrrole (3). Treatment of 3 with triethyl orthoformate followed by the addition of sodium hydride and 1 equivalent of the appropriate alkylating agent, with a catalytic amount of tetrabutylammonium iodide, gives the intermediate (5). The synthetic route is dependent upon correctly placing the alkyl substituents on the N7 position. Alkylation of 5 before cyclization controls the regiochemistry. Reaction of 5 with methanolic ammonia affords the 7-alkylated-4-amino-6-bromo-5-cyanopyrrolo[2,3-d] pyrimidines (6). Thus, by selecting the appopriate alkyl substiuent, the desired 7-alkylated-4-amino-6-bromo-5-cyanopyrrolo[2,3-d]pyrimidines can be prepared.

A variety of alkylating groups (17a–e) was needed in order to synthesize new phenethyl derivatives of the pyrrolo [2,3-d]pyrimidine. These alkylating agents can be prepared according to Scheme 2.

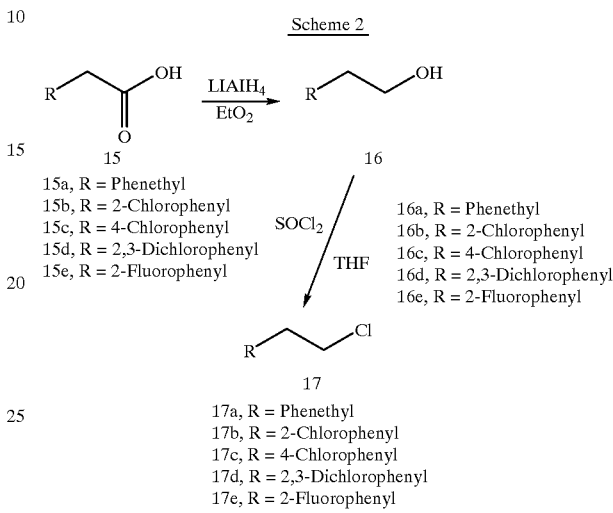

Using the substituted carboxylic acids (15a–e) as precursors, the corresponding alcohols (16a–e) could be synthesized in high yields by the action of lithium aluminum hydride. Treatment of 16a–e with thionyl chloride, using lithium chloride to aid in substitution, produces the chlorides (17a–e).

The majority of the phenethyl halide alkylating agents, through multiple trials, gave poor yields. A change in solvent and temperature did not appreciably affect the reaction rates or yields. Accordingly, different leaving groups, in place of the halides, need to be tried to create the desired products in more efficient yields.

b. General procedure to prepare 7-alkylated-4-amino-5-cyanopyrrolo[2,3-d]pyrimidines (7)

7-alkylated-4-amino-5-cyanopyrrolo[2,3-d]pyrimidines can be prepared from the 7-alkylated-4-amino-6-bromo-5-cyanopyrrolo[2,3-d]pyrimidines (6) via catalytic hydrogenation. This procedure is illustrated in Scheme 3 and can be can be described in detail as follows.

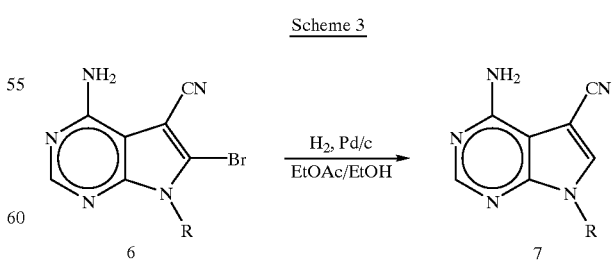

To a mixture of EtOAc/EtOH (2:1 v:v) is added the 6-bromo compound with 1.0% Pd/C (10% by weight) and 1N NaOH. The mixture is hydrogenated at room temperature and after 30 min the mixture is filtered, washed with hot EtOAc (2 times) and the filtrate evaporated to dryness. The resulting solid is suspended in $H_2O$/MeOH (3:1 v:v) and heated to boiling. To this solution is added decolorizing charcoal which was filtered over Celite and the filtrate cooled overnight at 4° C. The resulting solid can be collected by filtration and dried overnight to yield the desired compound (7).

c. General Procedure to Prepare 7-alkylated-4-amino-5-thiocarboxamido pyrrolo [2,3-d]pyrimidines (8)

The 7-alkylated-4-amino-5-thiocarboxamido pyrrolo[2,3-d]pyrimidines can be prepared from the correpsonding 7 compounds by reacting with methanolic sodium sulfide in a sealed vessel at 95° C. Thus, dry $H_2S$ is passed through a solution of sodium methoxide in dry methanol for 0.5 h. The 7 compound is added in one portion, and the mixture is stirred in a sealed pressure tube at 95° C. for 2 h. The resulting solution is allowed to cool to room temperature, then adjusted to pH 7 with 1N HCl. The solvent is evaporated to dryness and the resulting compound (8) is recrystallized from $H_2O$ containing a small amount of EtOH. This procedure is illustrated in Scheme 4.

Scheme 4

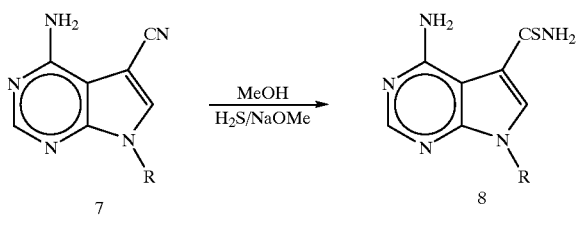

Similarly, reaction of the 7 compounds with methanolic sodium selenide would yield the selenoamide analogs.

d. General procedure to prepare a 7-alkylated-4-oxo-5-cyano pyrrolo[2,3-d]pyrimidines (9)

A 7-alkylated-4-oxo-5-cyano pyrrolo[2,3-d]pyrimidine (9) can be prepared from a corresponding 7 compound, according to the general procedure shown in Scheme 5.

Scheme 5

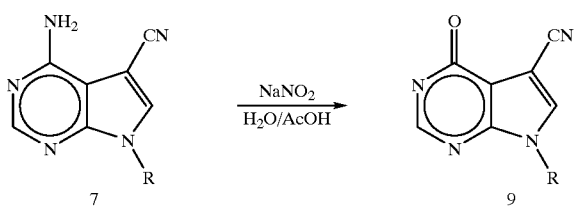

The 7 compound is suspended in distilled $H_2O$ and AcOH (about 11:1) and heated to 50° C. and $NaNO_2$ is added batch-wise over a period of 4.5 h. Then, the reaction is heated to 70° C. for 16 h. The resulting solid is cooled to 4° C. for 24 h, collected by filtration and dried in vacuo at 60° C. overnight to yield the desired 4-oxo product (9).

e. General procedure to prepare a 7-alkylated-4-methylamino-5-cyano pyrrolo [2,3-d]pyrimidines (10)

A 4-chloro compound is first prepared as follows. A corresponding 9 compound is dissolved in $POCl_3$ and the solution is heated at reflux for 12 min. The hot solution is poured onto ice water and the pH of the resulting mixture adjusted to 7 with $NH_4OH$ (38%). The solution is extracted with $CH_2Cl_2$ (2 times) from distilled $H_2O$ and $NaHCO_3$. The organic layer is collected and dried over $MgSO_4$, filtered and the filtrate evaporated to dryness. The solid is recrystallized from a MeOH/$H_2O$ mixture and decolorizing charcoal to provide the 4-chloro compound.

This 4-chloro compound is dissolved in methylamine (33% in abs. EtOH) and the solution stirred at room temperature for 2.5 h. The solution is then allowed to stand at 4° C. for 16 hr and the solid collected by filtration to furnish the product (10). This general procedure is illustrated in Scheme 6.

Scheme 6

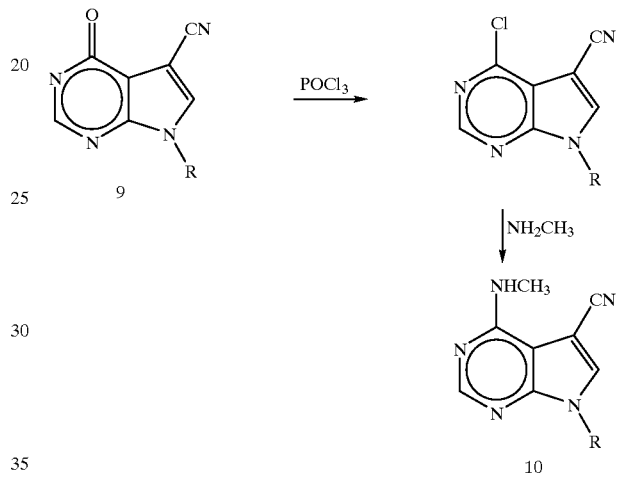

f. General procedure to prepare a 4-Methylamino-7-alkylated-pyrrolo[2,3-d]pyrimidine-5-thiocarboxamide (11)

A 4-Methylamino-7-(substituted)pyrrolo[2,3-d] pyrimidine-5-thiocarboxamide (11) can be prepared from its corresponding 10 compound as follows. NaOMe in dry MeOH is saturated with $H_2S$ (g) for 30 min. This solution is transferred to a steel vessel containing a corresponding 10 compound. The vessel is sealed and heated at 100° C. in an oil bath for 24 h. The solution is allowed to cool to room temperature and the pH adjusted to 7 with 1N HCl. To this solution is added silica which is applied to a column prepacked with silica. The column is eluted with hexanes/ EtOAc (70:30, v:v) to afford 11. The compound can be recrystallized from a $H_2O$/EtOH mixture to yield the product. This procedure is shown in Scheme 7.

Scheme 7

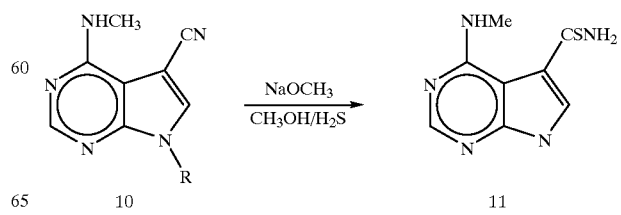

g. General procedure to prepare a 4,6-Diamino-7-alkylated-pyrrolo[2,3-d]pyrimidine-5-carbonitrile (12)

A corresponding 6 compound is placed in a steel vessel and the vessel is charged with liquid $NH_3$. The vessel should be sealed and the reaction heated at 100° C. for 16 h. The vessel should be allowed to cool to room temperature and further cooled to −75° C. at which time the vessel should be vented. The resulting solid is suspended in $H_2O$ and heated to boiling. Following filtration, the filtrate is allowed to stand at 4° C. for 16 hr and the product (12) can be collected by filtration. This general procedure is illustrated in Scheme 8.

Scheme 8

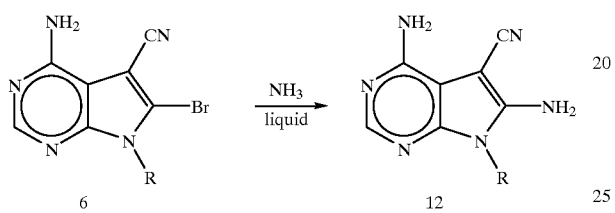

h. General procedure to prepare a 4,6-Diamino-7-alkylated pyrrolo[2,3-d]pyrimidine-5-thiocarboxamide (13)

NaOMe in dry MeOH is saturated with $H_2S$ (g) for 30 min. This solution is transferred to a steel vessel containing the corresponding a 4,6-Diamino-7-alkylated pyrrolo[2,3-d]pyrimidine-5-carbonitrile (12). The vessel should be sealed and heated at 100° C. in an oil bath for 19 hr. The solution should be allowed to cool to room temperature and the pH of the solution adjusted to 7 with 1N HCl. The resulting solution should be evaporated to dryness and the solid recrystallized from $H_2O$/MeOH and decolorizing charcoal. This procedure is illustrated in Scheme 9.

Scheme 9

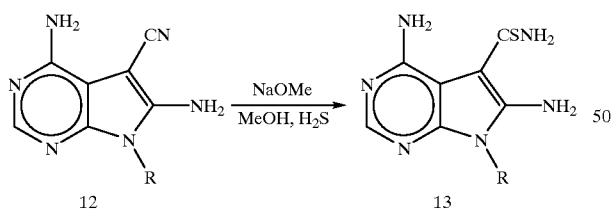

The compounds disclosed and tested for antiviral activity (see infra) have been prepared according to one or more of the above-described general procedures, or suitable modifications of the above-described general procedures. Such modifications are within the ordinary skill of the chemical and pharmaceutical arts.

An example of the application of the general procedures to prepare a specific compound is shown in Scheme 10, which illustrates the synthesis of 4-amino-5-thiocarboxamide-7-(4-fluorobenzyl) pyrrolo[2,3-d]pyrimidine.

Scheme 10

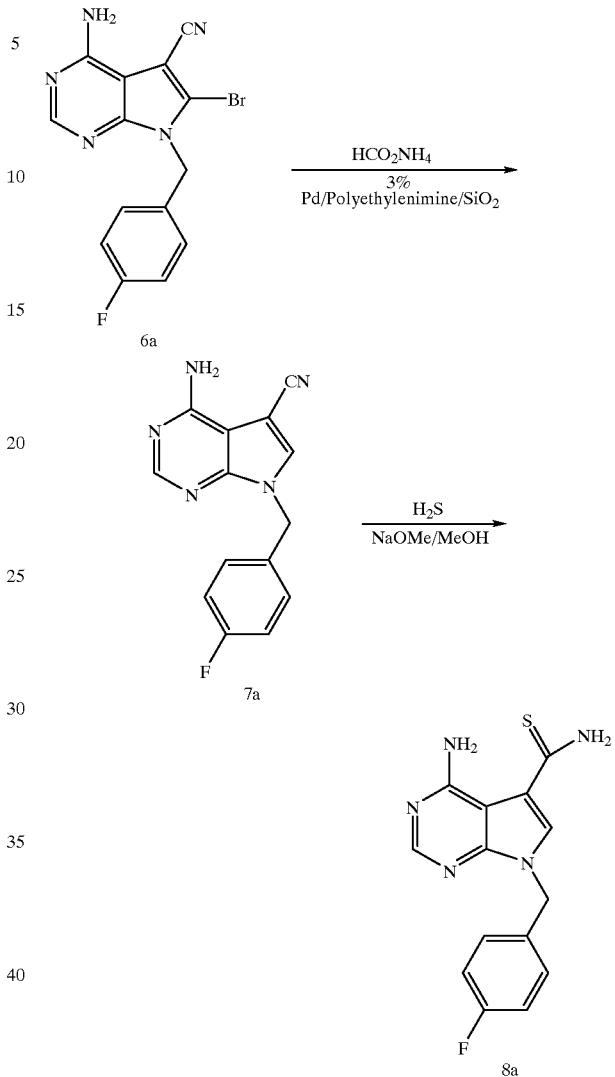

Some additional specific examples are described below which further illustrate the invention.

2. Specific Examples of Chemical Synthesis (i) 2-Amino-5-bromo-3,4-dicyanolpyrrole (3)

Compound 3 can be prepared according to Schemes 1 and 3, as discussed above. The more detailed procedure is as follows. A twelve-liter flask was fitted with an overhead stirrer, a condenser, a drying tube, and an internal thermometer. The flask was cooled in a MeOH/ice bath. Ethyl acetate (4 L), acetone (670 mL), and tetracyanoethylene (1) (128.09 g, 1 mol) were added. The solution was cooled to −10° C. HBr (1 L 33% w/w in AcOH, 4.1 M solution) was added dropwise at such a rate as to maintain the temperature at −10° C. A yellow solid began to precipitate during the addition. After the addition was complete, the suspension was stirred for an additional 3 hours. The yellow precipitate was collected by filtration, washed with ethyl acetate and ethyl ether, suspended in water (3 L), and was adjusted to pH 11 with 50% NaOH giving a dark solution. Decolorizing charcoal was then added to this solution, filtered through Celite, and the filtrate was acidified to pH 5 with glacial acetic acid. The mixture was allowed to stand at 5° C. for 18 hours. The product was then collected by filtration and oven dried (40° C., atmospheric pressure) for 7 days (117.4 g of brown solid, 56% yield): Mp: 180° C. decomp. TLC: Rf=0.71 (2%MeOH/CH$_2$Cl$_2$), Rf=0.32 (EtOAc-Hexanes, 2:1).

(ii) 7-Alkyl-4-amino-6-bromo-5-cyanpyrrolo[2,3-d]pyrimidine (6a–g)

The preparation of compounds 6a–g is illustrated in Scheme 1. Under an argon atmosphere, a mixture of 2-amino-5-bromo-3,4-dicyanopyrrole (3) (10.6g, 50mmol) and triethyl orthoformate (30 mL) in acetonitrile (300 mL) was heated under reflux for 3 hours at which time no starting material was detected by TLC. The solution was then concentrated under reduced pressure and coevaporated with toluene (3×125 mL) to give a dark brown solid. The solid was then suspended in CH$_2$Cl$_2$ and filtered through a bed of Celite to remove particulate matter. The CH$_2$Cl$_2$ solution was then concentrated under reduced pressure to give a light brown solid, which was dissolved in dry THF (125 mL). Under an atmosphere of argon. the THF solution of 2-bromo-3,4-dicyano-5-(ethoxymethylene)iminopyrrole (4) (theoretical, 14.2 g, 50 mmol) was added dropwise to a stirred suspension of NaH (1.44 g, 60 mmol, 2.4 g of a 60% dispersion in mineral oil) in THF (30 mL).

On completion of addition, the solution was stirred for 20 minutes. Tetrabutylammonium iodide (3.0 g) was added, and then a solution of alkyl halide (60–75 mmol) was added. The mixture was heated under reflux for a minimum of 24 hours and until no starting material was detected by TLC. The mixture was filtered through a bed of Celite to remove insolubles and concentrated under reduced pressure to a brown oil. This oil was dissolved in MeOH (100 mL) and 5N NH3/MeOH (150 mL). The flask was sealed and the mixture stirred for a minimum of 48 hours and until no uncyclized intermediate was detected by TLC. The product was isolated by filteration and recrystallized from AcOH. MP 222–223° C.; UV/.lambda. max nm (.epsilon.mM): (pH 1) 282 (19.1); (MeOH) 284 (22.1); (pH 11) 284 (19.1); 1H NMR (DMSO-d6): a 8.23 (1H, s, H-2), 7.00 (2H, br s, NH2), 5.58 (2H, s, NCH2), 3.46–3.52 (2H, q, OCH2), 1.03–1.07 (3H, t, CH3); Anal. Calc'd for C10 H20 N5 BrO: C, 40.56; H, 3.40; N, 23.65. Found: C, 40.70; H, 3.44; N, 23.58.

The following specific 7-alkylated-4-amino-6-bromo-5-cyanopyrrolo[2,3-d]pyrimidines were prepared from compound 6 and its derivatives. All reactions where the intermediates were not isolated were assumed to be on the 50 mmol scale.

(iii) 4-Amino-6-bromo-5-cyano-7-(4-fluorobenzyvl)pyrrolo[2,3-d]pyrimidine (6a, NE211)

From 4-fluorobenzyl chloride (10.84 g, 75 mmol) was obtained 6a after recrystallization from AcOH (3.06 g, 18% yield of off white powder). Mp: 263–265° C. ref. Mp: 254–265° C. TLC: Rf=0.48 (EtOAc-Hexanes, 2:1) $^1$H-NMR (300 MHz, dmso-d6) δ5.44 (s, 2H, CH$_2$), 7.04 (br. s, 2,NH$_2$), 7.14–7.20 (m, 2H, Ar), 7.24–7.27 (m, 2H, Ar), 8.23 (s, 1H, H-2).

(iv) 4-Amino-6-bromo-5-cyano-7-(4-trifluoromethylbenzyl)pyrrolo[2,3-]pyrimidine (6b, NE227)

From p-trifluoromethylbenzylchloride (10.0 g, 51 mmol) was obtained 6b after recrystallization from AcOH (5.43 g, 34% yield of light pink powder): Mp: 274–275° C. TLC: Rf=0.56 (EtOAc-Hexanes, 2:1). $^1$H-NMR (300 MHz, dmso-d$_6$) δ5.60 (s, 2H, CH$_2$), 7.06 (s, 2H, NH$_2$), 7.36 and 7.72 (dd, 4H, Ar), 8.24 (s, 1H, H-2). Analysis calculated for C$_{15}$H$_9$BrF$_3$N$_5$: C, 45–46%; H, 2.29%; N, 17.67%. Found: C, 45.45%; H, 2.47%; N, 17.67%.

(v) 4-Amino-6-Bromo-5-cyano-7-(2-trifluoromethylbenzyl)pyrrolo[2,3-]pyrimidine (6c, NE233)

From o-trifluoromethylbenzylchloride (10.0 g, 51 mmol) was obtained 6c after recrystallization from AcOH (0.7 g, 5% yield of pink powder): Mp: 280° C. decomp. TLC: Rf=0.77 (EtOAc-Hexanes, 2:1). $^1$H-NMR (300 MHz, dmso-d$_6$) δ5.64 (s, 2H, CH$_2$), 6.47(dd, 1H, Ar-4), 7.10 (br.s, 2H, NH$_2$), 7.54 (m, 2H, Ar-3+5), 7.84 (dd, 1H, Ar-2), 8.21(s, 1H, H-2). Analysis Calculated for C$_{15}$H$_9$BrF$_7$N$_5$: C, 45.46%; 2.29%; N, 17.67%. Found: C, 47.69%; H, 3.03%; N, 16.51%.

(vi) 4-Amino-6-Bromo-5-cyano-7-(4-nitrophenethyl)pyrrolo[2,3-d]pyrimidine (6d, NE241)

From 4-nitrophenylethyl bromide(15.0 g, 65 mmol) was obtained 6d after recrystallization from AcOH (0.7 g, 3.5% yield of white powder): Mp: 250–0.251° C. TLC: Rf=0.53 (EtOAc-Hexanes, 2:1). $^1$H-NMR (300 Mhz, dmso-d$_6$) δ3.22 (t, 2H, CH$_2$), 4.51(t, 2H, CH$_2$), 6.96(br.s., 2H, NH$_2$), 7.33–7.36(d, 2H, Ar), 8.09–8.12(d, 2H, Ar), 8.18(s, 1H, H-2). Analysis Calculated for C$_{15}$H$_{11}$BrN$_6$O$_2$: C, 46.51%; H, 2.87%; N, 21.70%. Found: C, 46.72%; H, 3.02%; N, 21.20%.

(vii) 4-Amino-6-Bromo-5-cyano-7-(4-chlorophenethyl)pyrrolo[2,3]pyrimidine (6f, NE253)

On a 25 mmol scale, 3,4-dicyano-5-(ethoxymethylene)iminopyrrole (7.1 g, 25 mmol) was prepared as described in the general procedure. This was then dissolved in CH$_3$CN (200 mL) and NaH (0.72 g, 30 mmol) was added slowly (in 20 mg portions) over a period 15 minutes. 4-chlorophenylethyl chloride(7.00 g, 40 mmol) was then added and the solution stirred at 54° C. for 10 days. The solution was then concentrated to a brown oil. This was then dissolved in 150 mL 5N NH$_3$ in EtOH, capped and stirred for 3 days. The product was recrystalizecl from AcOH (2.50 g, 26% yield of brown powder); Mp: 280° C. decomp. TLC: Rf=0.54 EtOAc-Hexanes (2;1) $^1$'H-NMR (dmso-d$_6$) δ3.06(t, 2H, CH$_2$), 4.45(t, 2H, CH$_2$.), 6.95(br, s, 2H$_1$NH$_2$), 7.08 and 7.09(d, 2H, Ar), 7.30 and 7.31(d, 2H, Ar), 8.21(s, 1H, H-2).

(viii) 4-Amino-6-Bromo-5-cyano-7-(n-butyl)pyrrolo[2,3-]pyrimidine (6 g, NE270)

On a 25 mmol scale, 3,4-dicyano-5-(ethoxymethylene)iminopyrrole (7.1 g, 25 mmol) was prepared as described in the general procedure. This was then dissolved in CH$_3$CN (200 mL) and NaH (0.72 g, 30 mmol) was added slowly over a period 15 minutes. N,N,N-trimethylbutylamnonium iodide (6.87 g, 28 mmol) was then added and the solution stirred at reflux for 7 days. The solution was then concentrated, dissolved in 150 mL 5N ethanolic ammonia and left.

(ix) 5-Cyano-4,6-diamino-7-(4-trifluoromethylbenzyl)pyrrolo[2,3-d]pyrimidine (12b, NE266)

Scheme 11 outlines the specific procedure to prepare 12b.

Scheme 11

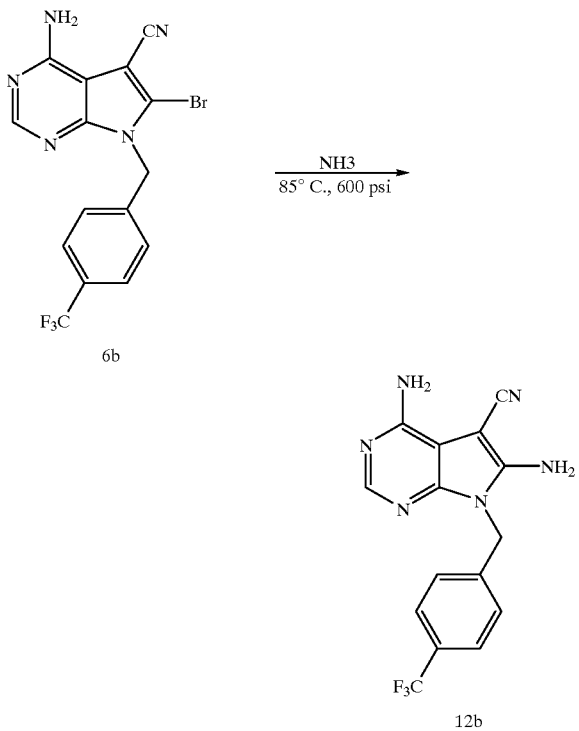

In a 500 mL stainless steel vessel was placed 6b (2.0 g, 5 mmol) and 250 mL of liquid ammonia. The vessel was sealed and heated at 85° C. and 600 psi for 48 hours. The vessel was cooled to room temperature and vented. The solid obtained was collected and suspended in $H_2O$ (75 mL). After stirring for 30 minutes the precipitate was collected by filtration and air-dried. The crude product was recrystallized from AcOH (0.39 g, 23% yield of white powder): Mp: 290° C. sharp TLC: Rf=0.26 in EtOAc-Hexanes (2:1) $^1$H-NMR (dmso-$d_4$) δ5.39(s, 2H, $CH_2$), 6.16(s, 2H, 6-$NH_2$), 7.26(s, 2H, 4-$NH_2$), 7.30 and 7.33(d, 2H, Ar), 7.68 and 7.70(d, 2H, Ar), 7.98(s, 1H, H-2).

(x) Preparation of Alcohols (16a–e) from the Corresponding Carboxylic Acid (15a–e) by Reduction with Lithium Aluminum Hydride The conversion of acids into alcohols is illustrated in Scheme 2, supra. The acids were dissolved in ethyl ether (100–500 mL) and added dropwise over a period of 1 hour to $LiAlH_4$ (1 equivalent) in ether (50 mL). The ethyl ether was kept below reflux with an ice bath as necessary. The reaction was stirred for a minimum of 2 hours and until no starting material was detected by TLC. The reaction was quenched with water until the solution turned white and viscous. The suspension was then filtered through Celite and the ether filtrate was washed with water (500 mL), a 0.5M HCl solution (500 mL), and dried over $MgSO_4$. The ether layer was concentrated under reduced pressure to yield the crude product which was then purified by vacuum distillation.

(xi) 4-Phenylbutyl alcohol (16a, NE230)

4-phenylbutyric acid (23.0 g, 0.14 mol) was used in the general procedure above. After distillation 16a was obtained (17.66 g, 84% yield of clear colorless oil): Bp: 166° C. (atmospheric pressure) TLC; Rf=0.44 ($CH_2Cl_2$). $^1$H-NMR (500 MHz, dmso-$d_4$) δ1.4–1.7(m, 4H, $CH_2CH_2$), 2.55(t, 2H, $ArCH_2$), 3.36(t, 2H, $CH_2OH$), 4.38(s, 1H, OH), 7.13–7.25 (m, 5H, Ar).

(xii) 2-Chlorophenylethyl alcohol (16b, NE23 1)

2-Chlorophenylacetic acid (50.0 g, 0.29 mol) was used in the general procedure above. After distillation 16b was obtained (39.53 g, 87% yield of clear colorless oil): BP: 160° C. (atmospheric pressure) TLC: Rf=0.50 ($CH_2Cl_2$). $^1$H-NMR (500 MHz, dmso-$d_6$) δ2.86(t, 2H, $CH_2OH$), 3.61(t, 2H, $ArCH_2$), 4.78(t, 1H, OH), 7.20–7.35(m, 4H, Ar).

(xiii) 4-Chlorophenylethyl alcohol (16c, NE234)

4-Chlorophenylacetic acid (77.57 g, 0.455 mol) was used in the general procedure above. After distillation 16c was obtained (67.54 g, 95% yield of clear colorless oil): Bp: 167° C. (atmospheric pressure) TLC: Rf=0.40 ($CH_2Cl_2$). $^1$H-NMR (500 MHz, dmso-$_6$) δ2.72(t, 2H, $CH_2OH$), 3.60(t, 2H, $ArCH_2$), 4,68(telH,OH), 7.21–7.30(m, 4H, Ar).

(xiv) 2,4-Dichlorophenylethyl alcohol (16d, NE236)

2,4-Dichlorophenylacetic acid (50.0 g, 0.244 mol) was used in the general procedure above. After distillation 16d was obtained (39.72 g, 85% yield of clear colorless oil): Bp: 186° C. (atmospheric pressure) TLC: Rf=0.38 ($CH_2Cl_2$). $^1$H-NMR (500 MHz, dmso-$d_6$) δ2.83(t, 2H, $CH_2OH$), 3.60 (m, 2H, $ArCH_2$), 4.78(t, 1H, OH), 7.30–7.35(m, 2H, H-5+6), 7.50(s, 1H, H-3).

(xvii) 2-Fluorophenylethyl alcohol (16e, NE238)

2-Fluorophenylacetic acid (28.0 g, 0.182 mol) was used in the general procedure above. After distillation 16e was obtained (22.94 g, 90% yield of clear colorless oil): Bp: 137° C. (atmospheric pressure) TLC: Rf=0.38 ($CH_2Cl_2$). $^1$H-NMR (500 MHz, dmso-$d_6$) δ2.78(t, 2H, $CH_2OH$), 3.63 (m, 2H, $ArCH_2$), 4.78(t, 1H, OH), 7.10–7.30(m, 4H, Ar).

(xviii) Conversion of Alkyl Alcohols (16a–e) to Alkyl Chlorides(17a–e)

The purified alcohol was then dissolved in THF (100–500 mL) and added in one portion to $SOCl_2$ (1.20 equivalents) in THF (50 mL). LiCl (1 g) was added and the solution was heated at reflux for 2 hours. The reaction was then dissolved in water (500 mL) and ethyl ether (500 mL) and the ether layer was washed with saturated solution of $NaHCO_{3(Sat. Sol'n)}$, 0.5M HCl solution (pH 2) and dried over $MgSO_4$. The ether layer was concentrated under reduced pressure to a light yellow oil. The crude product was purified by vacuum distillation.

(xix) 1-Chloro-4-phenylbutyl chloride -(17a, NE242)

4-phenylbutyl alcohol (17.66 g, 0.12 mol) was used in the above general procedure. After distillation 17a was obtained (12.15 g, 60% yield of clear colorless oil): Bp: 152° C. (atmospheric pressure) TLC: Rf.=0.86 ($CH_2Cl_2$). $^1$H-NMR (500 MHz, $CDCl_3$) δ1.91(t, 4H, $CHI_2CH_2$), 2.76(t, 2H, $CH_2Cl$), 3.65(t, 2H, $ArCH_2$) 7.30–7.55(m, 5H, Ar).

(xx) 2-Chlorophenylethyl chloride (17b, NE244)

2-Chlorophenylethyl alcohol (39.53 g, 0.252 mol) was used in the above general procedure. After distillation 17b was obtained (39–09 g, 89% yield of clear slightly yellow oil): Bp: 160° C.(atmospheric pressure)TLC: Rf=0.86 (CH$_2$Cl$_2$). $^1$H-NMR (500 MHz, CDCl$_j$) δ3.11(t, 2H, CH$_2$Cl), 3.67(t, 2H, ArCH$_2$), 7.10–7.20(m,4H,Ar).

(xxi) 4-Chlorophenylethyl chloride (17c, NE246)

4-Chlorophenylethyl alcohol (67.54 g, 0.43 mol) was used in the above general procedure. After distillation 17c was obtained (60.88 g, 81% yield of clear colorless oil): Bp: 147° C. (atmospheric pressure) TLC: Rf=0.89 (CH$_2$Cl$_2$). $^1$H-NMR (500 MHz, dmso-d$_6$) δ3.02(t,2H, CH$_2$Cl), 3.83(t, 2H, ArCH$_2$), 7.27–7.36(m, 4H, Ar).

The following additional compounds were prepared according to the above described general methods.

4- Amino-6-bromo-7-(ethoxymethyl)pyrrolo[2,3-d] pyrimidine-5-carbonitrile (JJ 164); 4-Amino-6-bromo-7-[(2-methoxyethoxy)methyl]pyrrolo[2,3-d]pyrimidine-5-carbonitrile (JJ 194); 4- Amino-6-bromo-7-(benzyloxymethyl)pyrrolo[2,3-d]pyrimidine-5-carbonitrile (JJ 078); 4-Amino-6-bromo-7-(benzyl)pyrrolo[2,3-d] pyrimidine-5-carbonitrile(LI90); 4-Amino-6-bromo-7-(4-methylbenzyl)pyrrolo[2,3-d]pyrimidine-5-carbonitrile (LI 126); 4- Amino-6-bromo-7-(3-methylbenzyl)pyrrolo [2,3-d] pyrimidine-5-carbonitrile (JJ 022); 4-Amino-6-bromo-7-(2-methylbenzyl)pyrrolo[2,3-d]pyrimidine-5-carbonitrile (MC 158); 4-Amino-6-bromo-7- (4-tert-butylbenzyl)pyrrolo [2,3-d]pyrimidine -5-carbonitrile (MC 160); 4-Amino-6-bromo-7-(4-methoxybenzyl)pyrrolo[2,3-d]pyrimidine-5-carbonitrile (MC 166); 4-Amino-7-(ethoxymethyl)pyrrolo [2,3-d]pyrimidine-5-carbonitrile (JJ 176); 4-Amino-7-[(2-methoxyethoxy)methyl]pyrrolo[2,3-d]pyrimidine-5-carbonitrile (JJ 202); 4-Amino-7-(benzyloxymethyl)pyrrolo [2,3-d]pyrimidine-5-carbonitrile (LI 240); 4-Amino-7-(benzyl)pyrrolo[2,3-d]pyrimidine-5-carbonitrile (LI 110); 4-Amino-7-(4-methylbenzyl)pyrrolo[2,3-d]pyrimidine-5-carbonitrile (LI 130): 4-Amino-7-(3-methylbenzyl)pyrrolo [2,3-d]pyrimidine-5-carbonitrile (MC 168); 4-Amino-7-(2-methylbenzyl)pyrrolo[2,3-d]pyrimidine-5-carbonitrile (LI 246); 4-Amino-7-(4-tert-butylbenzyl)pyrrolo[2,3-d] pyrimidine-5-carbonitrile (JJ 104); 4-Amino-7-(4-methoxybenzyl)pyrrolo[2,3-d]pyrimidine-5-carbonitrile (JJ 092); 4-Amino-7-(ethoxymethyl)pyrrolo[2,3-d]pyrimidine-5-thiocarboxamide (LI 216); 4-Amino-7-[(2-methoxyethoxy)methyl]pyrrolo[2,3-d]pyrimidine-5-thiocarboxamide (JJ 048); 4-amino-7-(benzyloxymethyl) pyrrolo[2,3-d]pyrimidine-5-thiocarboxamide (LI 250); 4-Amino-7-(benzyl)pyrrolo[2,3-d]pyrimidine-5-thiocarboxamide (LI 128); 4-Amino-7-(4-methylbenzyl) pyrrolo [2,3-d]pyrimidine-5-thiocarboxamide (LI 144); 4-Amino-7-(3-methylbenzyl)pyrrolo[2,3-d]pyrimidine-5-thiocarboxamide (JJ 072); 4-Amino-7-(2-methylbenzyl) pyrrolo[2,3-d]pyrimidine-5-thiocarboxamide (JJ 026); 4-Amino-7-(4-tert-butylbenzyl)pyrrolo[2,3-d]pyrimidine-5-thiocarboxamide (JJ 114); 4-Amino-7-(4-methoxybenzyl) pyrrolo[2,3-d]pyrimidine-5-thiocarboxamide (JJ 098); 4-Amino-7-(ethoxymethyl)pyrrolo[2,3-d]pyrimidine-5-selenocarboxamide; 5-Cyano-7-(ethoxymethyl)pyrrolo[2,3-d]pyrimidin-4-one (JJ 178). 5-Cyano-7-[(2-methoxyethoxy)methyl]pyrrolo[2,3-d]pyrimidin-4-one (JJ 192); 4-Chloro-7-ethoxymethyl)pyrrolo[2,3-d] pyrimidine-5-carbonitrile (JJ 172); 4-Chloro-7-[(2-methoxyethoxy)methyl]pyrrolo[2,3-d]pyrimidine-5-carbonitrile (JJ 242); 4-Methylamino-7-(ethoxymethyl) pyrrolo[2,3-d]pyrimidine-5-carbonitrile (JJ 278); 4-Methylamino-7-[(2-methoxyethoxy)methyl]pyrrolo[2,3-d]pyrimidine -5-carbonitrile (MC 014); 4-Methylamino-7-(ethoxymethyl)pyrrolo[2,3-d]pyrimidine-5-thiocarboxamide (MC 032); 4-Methylamino-7-[(2-methoxyethoxy)methyl]pyrrolo[2,3-d]pyrimidine-5-thiocarboxamide (MC 030); 4,6-Diamino-7-(ethoxymethyl)pyrrolo[2,3-d]pyrimidine-5-carbonitrile (JJ 028); 4,6-Diamino-7-[(2-methoxyethoxy)methyl]pyrrolo[2,3-d]pyrimidine -5-carbonitrile (JJ 070); 4,6-Diamino-7-(benzyloxymethyl)pyrrolo[2,3-d]pyrimidine-5-carbonitrile (JJ 082); 4,6-Diamino-7-(ethoxymethyl)pyrrolo[2,3-d] pyrimidine-5-thiocarboxamide (JJ 076); 4,6-Diamino-7-[(2-methoxyethoxy)methyl] pyrrolo[2,3-d]pyrimidine-5-thiocarboxamide (JJ 088); and 4,6-Diamino-7-(benzyloxymethyl)pyrrolo[2,3-d]pyrimidine-5-thiocarboxamide (JJ 100).

The above reaction schemes and procedures are for illustrative purposes only and should not be considered as limiting in any way the scope of the invention disclosed herein. Moreover, the pyrrolo[2,3-d]pyridines disclosed herein can be prepared by other methods than those disclosed hereinabove, wherein such other methods are known to those of ordinary skill in the art. For further guidance, see Swayze, E. E., et al, in: L. B. Townsend and R. S. Tipson (Eds), *Nucleic acid chemistry; improved and new synthetic procedures, methods and techniques,* Part IV, pp. 16–18, Wiley-Interscience, New York, 1991 and U.S. Pat. No. 5,543,413, the contents of which are incorporated by reference herein to illustrate the synthetic aspects of the present invention further.

D. In Vitro Antiviral Evaluation Methods (a) Cells and Viruses

The routine growth and passage of KB and BSC-1 cells was performed in monolayer cultures using minimal essential medium (MEM) with either Hanks salts [MEM(H)] or Earle salts [MEM(E)] supplemented with 10% calf serum. The sodium bicarbonate concentration was varied to meet the buffering capacity required. Cultures of diploid human foreskin fibroblast (HFF) or MRC-5 cells were grown in medium consisting of MEM(E) with 10% fetal bovine serum. Cells were passaged at 1:2 to 1:10 dilutions according to conventional procedures by using 0.05% trypsin plus 0.02% EDTA in a HEPES buffered salt solution (HBS) [Shipman, C., Jr., *Proc. Soc. Exp. Biol.,* 130: 305–310, 1969] as described previously [Turk, S. R., et. al, *Antimicrob. Agents Chemother.,* 31:544–550, 1987]. HFF and MRC-5 cells were passaged only at 1:2 dilutions. The Towne strain, plaque-purified isolate Po, of HCMV was kindly provided by Dr. Mark Stinski, University of Iowa. The KOS strain of HSV-1 was used in most experiments and was provided by Dr. Sandra K. Weller, University of Conn.

(b) Virological Procedures

Stock HCMV was prepared by infecting HFF cells at a multiplicity of infection (m.o.i.) of <0.01 plaque-forming units (p.f.u.) per cell. Cell growth medium was changed every four days until cytopathology was evident in all cells (approximately 21 days). Supernatant fluids were retained as the virus stock.

High titer HSV-1 stocks were prepared by infecting BSC cells at an m.o.i. of <0.1 as detailed previously [Turk, S. R., et al., *Antimicrob. Agents Chemother.,* 31:544–550, 1987].

Virus titers were determined using monolayer cultures of HFF cells for HCMV and monolayer cultures of BSC-1 cells for HSV-1 as described earlier [Prichard, M. N., et al., *J. Virol. Methods,* 28:101–106, 1990]. Briefly, HFF or BSC-1 cells were planted as described above in 96-well cluster dishes and incubated overnight at 37. degree. C. in a humidified 3% C02 -97% air atmosphere. The next day cultures were inoculated with HCMV or HSV-1 and serially diluted 1:3 across the remaining eleven columns of the 96-well plate. Cultures were incubated at 37. degree. C. for 2 hr to permit virus adsorption and then virus inoculum was replaced with 0.2 ml of fresh medium. Cultures were incubated for seven days for HCMV, two or three days for HSV-1, the medium was removed, and the cell sheets were stained with 0.1% crystal violet in 20% methanol.

HCMV plaques were enumerated under 20-fold magnification in wells having the dilution which gave 5 to 20 plaques per well. HSV-1 plaques were counted with the unaided eye or at 3–10 fold magnification. Virus titers were calculated according to the following formula: Titer (p.f.u./ml)=number of plaques.times.5.times.3n; where n represents the nth dilution of the virus used to infect the well in which plaques were enumerated.

(c) Assays for Antiviral Activity

1. HCMV Plaque Reduction Assay

HFF cells in 24-well cluster dishes were infected with approximately 100 p.f.u. of HCMV per $cm^2$ cell sheet using the procedures detailed above. Following virus adsorption, compounds dissolved in growth medium were added to duplicate wells in four to eight selected concentrations. After incubation at 37° C. for 7 to 10 days, cell sheets were fixed, stained with crystal violet and microscopic plaques enumerated as described above. Drug effects were calculated as a percentage of reduction in number of plaques in the presence of each drug concentration compared to the number observed in the absence of drug.

2. HCMV Yield Assay

HFF cells were planted as described above in 96-well cluster dishes, incubated overnight, medium removed and the cultures were inoculated with HCMV at a m.o.i. of 0.5 to 1 p.f.u. per cell as reported elsewhere (see Prichard, M. N et al., *J. Virol. Methods* 1990, 28, 101–106). After virus adsorption, inoculum was replaced with 0.2 mL of fresh medium containing test compounds. The first row of 12 wells was left undisturbed and served as virus controls. Each well in the second row received an additional 0.1 mL of medium with test compound at three times the desired final concentration. The contents of the 12 wells were mixed by repeated pipetting and then serially diluted 1:3 along the remaining wells. In this manner, six compounds could be tested in duplicate on a single plate with concentrations from 100 mM to 0.14 mM. Plates were incubated at 37° C. for seven days, subjected to one cycle of freezing and thawing; aliquots from each of the eight wells of a given column were transferred to the first column of a fresh 96-well monolayer culture of HFF cells. Contents were mixed and serially diluted 1:3 across the remaining eleven columns of the secondary plate. Each column of the original primary plate was diluted across a separate plate in this manner. Cultures were incubated, plaques were enumerated, and titers calculated as described above.

3. HSV-1 ELISA

An ELISA was employed (see Prichard, M. N. and Shipman, C., Jr., *Antiviral Res.* 1990, 14, 181–206) to detect HSV-1. Ninety-six-well cluster dishes were planted with 10,000 BSC-1 cells per well in 200 $\mu$L per well of MEM(E) plus 10% calf serum. After overnight incubation at 37° C., selected drug concentrations in quadruplicate and HSV-1 at a concentration of 100 p.f.u./well were added. Following a 3-day incubation at 37° C., medium was removed, plates were blocked, rinsed, and horse radish peroxidase conjugated rabbit anti-HSV-1 antibody was added. Following removal of the antibody containing solution, plates were rinsed, and then developed by adding 150 $\mu$L per well of a solution of tetramethylbenzidine as substrate. The reaction was stopped with $H_2SO_4$ and absorbance was read at 450 and 570 nm. Drug effects were calculated as a percentage of the reduction in absorbance in the presence of each drug concentration compared to absorbance obtained with virus in the absence of drug.

4. HHV-6 (ELISA)

An enzyme-linked immunosorbent assay (ELISA) is performed in covalent amine plates (Costar, Cambridge, Mass.). The plates are activated by the addition of a homobifinctional crosslinking agent, bis(sulfosuccinimidyl) suberate and then washed with PBS. Samples consisting of 150 $\mu$l of suspended HSB2 cells are infected with HHV-6 and previously incubated with drug on a separate plate are solubilized in Triton X-100 in coating buffer. The plate is covered and incubated for 1 hour at 37° C. in a 5% $CO_2$ atmosphere. These binding conditions facilitated covalent attachment of the antigen to the free end of the crosslinker. After covalent binding, the antigen solution is decanted and the plate is washed six times in HEPES buffered saline (see Shipman, C., Jr., *Proc. Soc. Exp. Biol.* 1969, 130, 305–310) with 0.05% Tween 20 (HBS-T), and soaked for three minutes for each wash. Unbound sites on the plate are blocked, the blocker decanted, and diluted primary monoclonal antibody, specific for HHV-6 (GS) is added. The plate is then covered and incubated for 1 hour at 37° C. The plate is washed again, blocker is added again, and horse radish peroxidase-labeled rabbit anti-mouse antibody added to each well. The plate is incubated for 1 hour at 37° C., washed again as described above, and developed using TMB-Turbo (Pierce, Rockford, Ill.) for 30 minutes at room temperature. The reaction is stopped with 2 M $H_2SO_4$. Absorbance in each well is determined at 450/570 nanometers.

5. HIV-1

This assay measures the presence of HIV in supernatants of CEM cells (ATCC) infected with strain IIIB of HIV-1 by the amount of RT activity. Reverse transcriptase (RT) is employed as a marker for HIV-1. Cells are grown, infected, and incubated in the presence of seven concentrations (one-half log 10 dilutions) beginning at 1 or 100 $\mu$M of compounds to be assayed. Procedures and the RT assay are performed as detailed in Kucera, L. S. et al., *AIDS Res. Human Retroviruses* 1993, 9, 307–314; White, E. L. et al., *Antiviral Res.* 1991, 16, 257–266.

Although the compounds are shown to be particularly effective against HCMV and HSV-1, it is within the scope of this invention that other viruses are effectively treated with the compounds of this invention by use of methods described herein and others well known to those of skill in the art. Other viruses that can be treated as defined herein and within the scope of the present invention include all members of the herpes family, and human immunodeficiency virus (HIV) and hepatitis viruses, for example, hepatitis B virus (HBV). Methods of determining the efficiency of any of the compounds of this invention against HBV are well known in the art; see for example, the methods shown in U.S. Pat. No. 5,399,580 to Daluge.

An additional member of the hepatitis virus family that can be treated as defined herein is hepatitis C virus (HCV). U.S. Pat. No. 5,679,342, issued to Houghton et al. describes in detail methods for employing an extracorporeal cell system infected with HCV to screen for the compounds most active against HCV. In brief, the method comprises: (a) providing a composition containing the compound of this invention to be tested; (b) providing an extracorporeal cell system capable of being infected by HCV; (c) providing a biological sample containing infective HCV; (d) incubating the compositions of (a) and (c) with the cell system of (b)

under conditions that would, in the absence of (a), allow infection of HCV in the cell system; and (e) detecting inhibition of viral infection after incubation. Preferred cell systems as disclosed in U.S. Pat. No. 5,679,342, include hepatocytes, macrophages, more preferably Kupffer macrophages, and B lymphocytes. Cell lines derived from organs of hepatocytic origin also are suitable for use in the assay described above. One can also use the above noted assay to test for the inhibition of viral replication by incubating the compositions of (a) and (b) under conditions that would, in the absence of (a), allow replication of HCV in the cell line and then detecting inhibition of viral replication after incubation.

Another method well known in the art for testing the antiviral activity of compounds against HCV is the helicase inhibition assay described, for example, in Lain et al., (1991) *Nucleic Acids Res.* 69:1720–1726 and Kim et al., (1995) *Biochem. Biophys*, Res. Comm. 160–166.

When the method is practiced in vivo in a subject such as a human patient, the compound can be added to a pharmaceutically acceptable carrier and systemically or topically administered to the subject, such as a human patient or a mammal such as a mouse, a rat, a woodchuck, or a simian.

The compositions also can be administered to subjects or individuals susceptible to or at risk of a viral infection, such as HCMV, HSV-1 or herpes virus infection. Thus, this invention also provides a prophylactic method of inhibiting viral replication, proliferation and/or viral infection in a subject by administering to a subject a prophylactically effective amount of the compound or composition under suitable conditions such that viral replication, proliferation or infection is inhibited. A "prophylactically effective amount" is an amount which inhibits viral infection, reproduction and proliferation in a subject challenged with the virus without toxicity to the cells and subject being treated.

(d) Cytotoxicity Assays

Two different assays were used to explore cytotoxicity of selected compounds: (i) Cytotoxicity produced in stationary HFF cells was determined by microscopic inspection of cells used in plaque assays which were not affected by the virus [Turk, S. R., et al, *Antimicrob. Agents Chemother.,* 31: 544–550, 1987], and (ii) The effect of compounds during two population doublings of KB cells was determined by crystal violet staining and spectrophotometric quantitation of dye eluted from stained cells as described in, for example, Prichard, M. N., et al, *Antimicrob. Agents Chemother.,* 35:1060–1065, 1991.

Briefly, 96-well cluster dishes were planted with KB cells at 3000–5000 cells per well. After overnight incubation at 37° C., test compound was added in quadruplicate at six to eight concentrations. Plates were incubated at 37° C for 48 hours in a $CO_2$ incubator, rinsed, fixed with 95% ethanol, and stained with 0.1% crystal violet. Acidified ethanol was added and plates read at 570 nm in a spectrophotometer designed to read 96-well ELISA assay plates.

(e) Data Analysis

Dose-response relationships were constructed by linearly regressing the percent inhibition of parameters derived in the preceding sections against logarithm 10 drug concentrations. Fifty-percent inhibitory (IC50) concentrations were calculated from the regression lines [Goldstein, A., *Biostatistics: An Introductory Text,* MacMillan, New York, pp. 156–161 (1964)]. Samples containing positive controls (acyclovir for HSV-1 and ganciclovir for HCMV) were used in all assays.

2. Results (a) Antiviral Evaluation

Compounds were evaluated for activity against human cytomegalovirus (HCMV) and herpes simplex virus type 1 (HSV-1). The cytotoxicity of each compound was determined as detailed above in both human foreskin fibroblasts (HFF cells) and in KB cells. These results are presented in Table 1.

TABLE 1

| Compound # | HCMV | HSV-1 | HFF | KBgrv |
|---|---|---|---|---|
| 1414 | 17 | 45 | >120 | 20 |
| 1429 | 1.8 | 33 | >100 | 60 |
| 1444 | 0.8 | 85 | >10 | >100 |
| 1360 | 1.6 | >100 | >10 | >100 |
| 1382 | >10 | >100 | >10 | >100 |
| 659 | 171.33 | 32.6 | 118 | 75 |
| 1428 | 38 | 50 | 45 | 20 |
| 636 | 14.50 | >100 | 100 | 222 |
| 826 | 222.00 | >100 | 222 | 222 |
| 658 | 181.33 | >100 | 141 | 222 |
| 845 | 28 | 50 | 100 | 1 |
| 839 | 13.00 | 35 | 127 | 47 |
| 1419 | 4.2 | 16 | 100 | 50 |
| 1412 | 5 | 45 | 100 | >100 |
| 1421 | 42 | >100 | >100 | >100 |
| 1441 | 21 | 90 | 100 | 16 |
| 1363 | 2.7 | 90 | >100 | 50 |
| 1353 | 1.4 | 60 | 116.5 | >100 |
| 1443 | >10 | >100 | >10 | >100 |
| 1388 | 116.5 | >100 | 116.5 | >100 |
| 1461 | >100 | >100 | >100 | >100 |
| 1462 | >100 | >100 | >100 | >100 |
| 1373 | 10.5 | >100 | 10.5 | >100 |
| 1331 | >10 | >100 | >10 | >100 |
| 1374 | >10 | >100 | >10 | >100 |
| 1427 | >10 | >100 | >10 | >100 |
| 1451 | 12 | 50 | >100 | 40 |
| 1365 | .3 | 33 | >100 | 60 |
| 1356 | .2 | 17.041 | 46 | 76 |
| 1389 | .2 | >100 | >10 | 15 |
| 1348 | .6 | 155.92 | >10 | >100 |
| 1352 | >100 | 100 | >100 | 146 |
| 1425 | 5 | >100 | >100 | >100 |
| 1455 | 6.5 | >100 | >100 | 40 |
| 1368 | .7 | 10 | 32 | >100 |
| 1396 | 17 | 45 | >100 | 40 |
| 1446 | >1 | 0.65 | 100 | 10 |
| 1463 | >10 | | >10 | |
| 1351 | 1 | 222 | >100 | >100 |
| 1409 | 100 | >100 | >100 | >100 |
| 1369 | <0.1 | 0.3 | 100 | 82 |
| 1413 | .5 | 1.5 | 32 | 38 |
| 1376 | 28 | 35 | 100 | 70 |
| 1362 | >10 | >100 | >10 | >100 |
| 1347 | >10 | 222 | >10 | >100 |
| 1350 | 5 | 121 | >100 | 50 |
| 1372 | >10 | >100 | >10 | >100 |
| 1361 | >100 | >100 | >100 | >100 |
| 1329 | 19 | 40 | 46 | 33 |

In general, the 4-substituted-benzyl group at the N7 position produced good to excellent antiviral activity against HCMV. See compounds 1429, 1444, 1360, 1536, 1428, 839, 1419, 1412, 1363, 1352, 1365, 1356, 1389, 1348. Of these compounds, many of the compounds with an electron withdrawing group such as a halo, or nitro group at the 4-position of the benzyl group show excellent activity. See for example compounds 1429, 1444, 1360, 1352, 1356, 1365, 1389, and 1348. This is a novel finding of this invention.

In addition, the data reveal that, surprisingly, those compounds with a N7 substitution having an aralky group with longer alkyl chain such as phenethyl, or phenpropyl also showed excellent activity against HCMV. See for example compounds 1368, 1446, 1351, 1369, 1413, 1350.

The antiviral activity is also influenced by the substitutions at other positions on the pyrrolo[2,3-d]pyrimidine ring. For example, the excellent of longer alky chain phenyls at the 7-position is lost if the cyano group at the 5-position of the pyrrolo[2,3-d]pyrimidine is replaced with another nitro group such as a carboxamido group. See for example compound 1409.

Some activity was also seen in case of compounds having a 3-substituted benzyl groups. See compounds 1455 (having a 3-amino benzyl) and 1425 (having a 3-nitrobenzyl).

From the above data, which shows that compounds with an electron withdrawing group at the 4-position of a benzyl and compounds with a longer alkyl chain to attach a phenyl group to the N7 position of the pyrrolo[2,3-d]pyrimidine have excellent antiviral activity, compounds having both the desirable features, (i.e., compounds possessing an aralkyl group at the N7-position wherein the alkyl chain has greater than 2 carbons and the phenyl ring is substituted with various one or more electron-withdrawing groups) would have enhanced antiviral activity are within the scope of this invention. Such compounds would include for example: 4-amino-7-(2-(4-fluorophenyl))ethyl-pyrrolo[2,3-d]pyrimidine-5-carbonitrile; 4-amino-7-(3-(4-fluorophenyl)-propyl)-pyrrolo[2,3-d]pyrimidine-5-thiocarboxamide; 4-6-diamino-7-((2-(4-fluorophenyl))ethyl)-pyrrolo[2,3-d]pyrimidine-5-carbonitrile; 4-amino-6-bromo-7-((2-(4-fluorophenyl))ethyl)-pyrrolo[2,3-d]pyrimidine-5-carbonitrile; 4-amino-7-((2-(4-fluorophenyl))ethyl)-pyrrolo[2,3-d]pyrimidine-5-carbonitrile; and 4-amino-7-(3-(4-fluorophenyl)-propyl)-pyrrolo[2,3-d]pyrimidine-5-carboxamide among others. Since this invention provides methods for preparing such compounds and methods to evaluate their antiviral activity, such compounds are also within the scope of this invention.

We claim:

1. A compound having the structure:

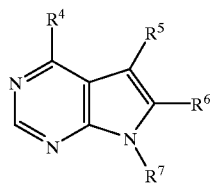

wherein:
$R^4$ is —$NR_1R_2$;
$R^5$ is —CN, —$CSNR_1R_2$ or —$CONR_1R_2$;
$R^6$ is —H, or halo, or —$NR_1R_2$;
wherein $R_1$ and $R_2$ are independently —H or a saturated or unsaturated hydrocarbyl or oxy-hydrocarbyl group containing from 1 to 4 carbons; and $R^7$ is of the formula $R_3$—Ar, wherein $R_3$ is a saturated or unsaturated hydrocarbyl or oxy-hydrocarbyl group containing from 1 to 4 carbons and Ar is an unsubstituted aryl or an aryl independently substituted with halo, nitro, amino, or a saturated or unsaturated hydrocarbyl or oxy-hydrocarbyl group containing from 1 to 4 carbons; provided that when $R^5$ is a —CN or —$CSNH_2$, and $R^6$ is a —H or —$NH_2$, and Ar is a —$C_6H_5$ or a phenyl substituted with only one saturated or unsaturated hydrocarbyl or oxy-hydrocarbyl group containing from 1 to 4 carbons then $R^3$ is not —$CH_2$—; and provided that when $R_1$, $R_2$ and $R^6$ are each H, and Ar is —$C_6H_5$ or a phenyl substituted with only one saturated or unsaturated hydrocarbyl or oxy-hydrocarbyl group containing from 1 to 4 carbons, then $R_3$ is not —$CH_2$—; and pharmaceutically acceptable salts, esters and ethers thereof.

2. A compound having the structure:

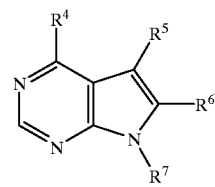

wherein
$R^4$ is —$NR_1R_2$;
$R^5$ is —CN or —$CSNR_1R_2$;
$R^6$ is —H, or halo, or —$NR_1R_2$;
wherein $R_1$ and $R_2$ are independently —H or a saturated or unsaturated hydrocarbyl or oxy-hydrocarbyl group containing from 1 to 4 carbons, and $R^7$ is of the formula $R_3$—Ar, wherein $R_3$ is a saturated or unsaturated hydrocarbyl or oxy-hydrocarbyl group containing from 1 to 4 carbons and Ar is an unsubstituted aryl or an aryl independently substituted with halo, nitro, amino, or a saturated or unsaturated hydrocarbyl or oxy-hydrocarbyl group containing from 1 to 4 carbons; provided that when $R^6$ is an —H or —$NH_2$, and Ar is —$C_6H_5$ or a phenyl substituted with only one saturated or unsaturated hydrocarbyl or oxy-hydrocarbyl group containing from 1 to 4 carbons, $R_3$ is a saturated or unsaturated hydrocarbyl or oxy-hydrocarbyl group containing from 1 to 4 carbons other than methyl such that —$R_3$— is not a —$CH_2$—; and pharmaceutically acceptable salts, esters and ethers thereof.

3. A compound having the structure:

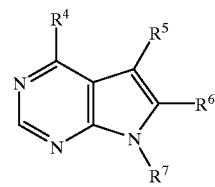

wherein:
$R^4$ is —$NR_1R_2$;
$R^5$ is —CN, —$CSNR_1R_2$ or —$CONR_1R_2$;
$R^6$ is —H or halo, or —$NR_1R_2$;
wherein $R_1$ and $R_2$ are independently —H or a saturated or unsaturated hydrocarbyl or oxy-hydrocarbyl group containing from 1 to 4 carbons and $R^7$ is of the formula $R_3$—Ar, wherein $R_3$ is a saturated or unsaturated hydrocarbyl or oxy-hydrocarbyl group containing from 1 to 4 carbons and Ar is an unsubstituted aryl or an aryl independently substituted with halo, nitro, amino or a saturated or unsaturated hydrocarbyl or oxy-hydrocarbyl group containing from 1 to 4 carbons; provided that when $R^6$ is a bromo and Ar is —$C_6H_5$ or a phenyl substituted with only one saturated or unsaturated hydrocarbyl or oxy-hydrocarbyl group containing from 1 to 4 carbons, then $R_3$ is a saturated or unsaturated hydrocarbyl or oxy-hydrocarbyl group containing from 1 to 4 carbons other than methyl; and provided that when $R_1$, $R_2$ and $R^6$ are each H and Ar is $C_6H_5$ or a phenyl substituted with only one saturated or unsaturated hydrocarbyl or oxy-hydrocarbyl group containing from 1 to 4 carbons, then —$R_3$— is not a —$CH_2$—; and its pharmaceutically acceptable salts, esters and ethers thereof.

4. A compound having the structure:

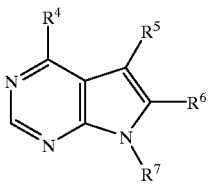

wherein:
R$^4$ is —NR$_1$R$_2$;
R$^5$ is —CN, —CSNR$_1$R$_2$ or —CONR$_1$R$_2$;
R$^6$ is —H or halo, or —NR$_1$R$_2$;
wherein R$_1$ and R$_2$ are independently —H or a saturated or unsaturated hydrocarbyl or oxy-hydrocarbyl group containing from 1 to 4 carbons; and R$^7$ is of the formula R$_3$—Ar, wherein R$_3$ is a saturated or unsaturated hydrocarbyl or oxy-hydrocarbyl group containing from 1 to 4 carbons and Ar is an aryl independently substituted with halo, nitro, amino, or a saturated or unsaturated hydrocarbyl or oxy-hydrocarbyl group containing from 1 to 4 carbons; and provided that when R$_1$, R$_2$ and R$^6$ are each H and Ar is C$_6$H$_5$ or a phenyl substituted with only one saturated or unsaturated hydrocarbyl or oxy-hydrocarbyl group containing from 1 to 4 carbons, then —R$_3$— is not —CH$_2$—; and pharmaceutically acceptable salts, esters and ethers thereof.

5. A compound having the structure:

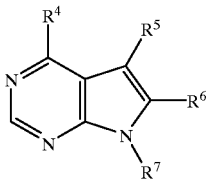

wherein:
R$^4$ is —NR$_1$R$_2$;
R$^5$ is —CN, —CSNR$_1$R$_2$ or —CONR$_1$R$_2$;
R$^6$ is —H or halo, or —NR$_1$R$_2$;
wherein R$_1$ and R$_2$ are independently —H or a saturated or unsaturated hydrocarbyl or oxy-hydrocarbyl group containing from 1 to 4 carbons; and R$^7$ is of the formula R$_3$—Ar, wherein R$_3$ is a saturated or unsaturated hydrocarbyl or oxy-hydrocarbyl group containing from 1 to 4 carbons and Ar is an unsubstituted aryl or an aryl independently substituted with halo, nitro, amino or a saturated or unsaturated hydrocarbyl or oxy-hydrocarbyl group containing from 1 to 4 carbons; provided that when R$_3$ is a saturated or unsaturated hydrocarbyl or oxy-hydrocarbyl group containing from 1 to 4 carbons other than methyl such that R$_3$ is not a —CH$_2$—; and provided that when R$_1$, R$_2$ and R$^6$ are each H and Ar is C$_6$H$_5$ or a phenyl substituted with only one saturated or unsaturated hydrocarbyl or oxy-hydrocarbyl group containing from 1 to 4 carbons, then —R$_3$— is not —CH$_2$— and pharmaceutically acceptable salts, esters and ethers thereof.

6. The compound of claim 2, wherein R$^4$ is —NH$_2$; R$^5$ is —CN and R$^6$ is —H.

7. The compound of claim 2, wherein R$^4$ is —NH$_2$; R$^5$ is —CSNH$_2$ and R$^6$ is —H.

8. The compound of claim 2, wherein R$^4$ is —NH$_2$; R$^5$ is —CN and R$^6$ is —NH$_2$.

9. The compound of claim 2, wherein R$^4$ is —NH$_2$; R$^5$ is —CN and R$^6$ is a halo group.

10. The compound of claim 9, wherein the halo group is a bromo or chloro.

11. The compound of claim 2, wherein:
R$^4$ is —NH$_2$; R$^5$ is —CN; R$^6$ is —H; R$^7$ is —CH(CH$_3$)—C$_6$H$_4$ (1414);
R$^4$ is —NH$_2$; R$^5$ is —CN; R$^6$ is —H; and R$^7$ is —CH$_2$—C$_6$H$_4$-4-F (1429);
R$^4$ is —NH$_2$; R$^5$ is —CN; R$^6$ is —H; and R$^7$ is —CH$_2$—C$_6$H$_4$-4-Cl (1444);
R$^4$ is —NH$_2$; R$^5$ is —CN; R$^6$ is —H; and R$^7$ is —CH$_2$—C$_6$H$_4$-4-NO$_2$ (1360);
R$^4$ is —NH$_2$; R$^5$ is —CN; R$^6$ is —H; and R$^7$ is —CH$_2$—C$_6$H$_4$-3-NO$_2$ (1362);
R$^4$ is —NH$_2$; R$^5$ is —CN; R$^6$ is —NH$_2$; and R$^7$ is —(CH$_2$)$_3$—C$_6$H$_5$ (1350);
R$^4$ is —NH$_2$; R$^5$ is —CSNH$_2$; R$^6$ is —H; and R$^7$ is —CH$_2$—CH$_2$—C$_6$H$_5$ (1446);
R$^4$ is —NH$_2$; R$^5$ is —CSNH$_2$; R$^6$ is —H; and R$^7$ is —CH$_2$—CH$_2$—CH$_2$—C$_6$H$_5$ (1413);
R$^4$ is —NH$_2$; R$^5$ is —CN; R$^6$ is —H; and R$^7$ is —CH$_2$—CH$_2$—C$_6$H$_5$ (1368);
R$^4$ is —NH$_2$; R$^5$ is —CN; R$^6$ is —NH$_2$; and R$^7$ is —CH(CH$_3$)—C$_6$H$_5$ (1451);
R$^4$ is —NH$_2$; R$^5$ is —CN; R$^6$ is —NH$_2$; and R$^7$ is —CH$_2$—C$_6$H$_5$ (1369);
R$^4$ is —NHCH$_3$; R$^5$ is —CN; R$^6$ is —NH$_2$; and R$^7$ is —CH$_2$—C$_6$H$_4$-3-NO$_2$ (1425);
R$^4$ is —NH$_2$; R$^5$ is —CN; R$^6$ is —NH$_2$; and R$^7$ is —CH$_2$—C$_6$H$_4$-3—NH$_2$ (1455);
R$^4$ is —NH$_2$; R$^5$ is —CN; R$^6$ is —NH$_2$ and R$^7$ is —CH$_2$—C$_6$H$_4$-4-F (1365);
R$^4$ is —NH$_2$; R$^5$ is —CN; R$^6$ is —NH$_2$; and R$^7$ is —CH$_2$—C$_6$H$_4$-4-Cl (1356);
R$^4$ is —NH$_2$; R$^5$ is —CN; R$^6$ is —NH$_2$; and R$^7$ is —CH$_2$—C$_6$H$_4$—Br (1389)
R$^4$ is —NH$_2$; R$^5$ is —CN; R$^6$ is —NH$_2$; and R$^7$ is —CH$_2$—C$_6$H$_4$-4-NO$_2$ (1348);
R$^4$ is —NH$_2$; R$^5$ is —CN; R$^6$ is —NH$_2$; and R$^7$ is —CH$_2$—C$_6$H$_4$-4-NH$_2$ (1352);
R$^4$ is —NH$_2$; R$^5$ is —CN; R$^6$ is —H; and R$^7$ is —CH$_2$—CH=CH—CH$_2$—C$_6$H$_5$ (1372);
R$^4$ is —NH$_2$; R$^5$ is —CN; R$^6$ is —NH$_2$; and R$^7$ is —CH$_2$—CH=CH—CH$_2$—C$_6$H$_5$ (1329);
R$^4$ is —NH$_2$; R$^5$ is —CN; R$^6$ is —Br; and R$^7$ is —CH(CH$_3$)—C$_6$H$_5$ (1363);
R$^4$ is —NH$_2$; R$^5$ is —CN; R$^6$ is —Br; and R$^7$ is —CH$_2$—C$_6$H$_4$-4-F (1353);
R$^4$ is —NH$_2$; R$^5$ is —CN; R$^6$ is —Br; and R$^7$ is —CH$_2$—C$_6$H$_4$-4-Cl (1355);
R$^4$ is —NH$_2$; R$^5$ is —CN; R$^6$ is —Br; and R$^7$ is —CH$_2$—C$_6$H$_4$-3-Cl (1461);
R$^4$ is —NH$_2$; R$^5$ is —CN; R$^6$ is —Br; and R$^7$ is —CH$_2$—C$_6$H$_3$-3,4-(Cl)$_2$ (1462);
R$^4$ is —NH$_2$; R$^5$ is —CN; R$^6$ is —Br; and R$^7$ is —CH$_2$—C$_6$H$_4$-4-Br (1373);
R$^4$ is —NH$_2$; R$^5$ is —CN; R$^6$ is —Br; and R$^7$ is —CH$_2$—C$_6$H$_4$-4-NO$_2$ (1374);
R$^4$ is —NH—CH$_3$; R$^5$ is —CN; R$^6$ is —Br; and R$^7$ is —CH$_2$—CH$_2$—C$_6$H$_5$ (1463);
R$^4$ is —NH$_2$; R$^5$ is —CN; R$^6$ is —Br and R$^7$ is —CH$_2$—C$_6$H$_5$ (1351);
R$^4$ is —NH$_2$; R$^5$ is —CN; R$^6$ is —Br; and R$^7$ is —(CH$_2$)$_3$—C$_6$H$_5$ (1347); and R$^4$ is —NH$_2$; R$^5$ is —CN; R$^6$ is —Br; and R$^7$ is —CH$_2$—CH═CH—C$_6$H$_5$ (1361).

12. The compound of claim 1, wherein R$^4$ is —NH$_2$; R$^5$ is —CONR$_1$R$_2$ and R$^6$ is a halo group.

13. The compound of claim 12, wherein R$_1$ and R$_2$ are independently —H or a saturated or unsaturated hydrocarbyl or oxy-hydrocarbyl group containing from 1 to 4 carbons and the halo group is a chloro or bromo.

14. The compound of claim 3, wherein R$^4$ is —NH$_2$; R$^5$ is —CN or —CONR$_1$R$_2$ and R$^6$ is a halo group.

15. The compound of claim 14, wherein R$_1$ and R$_2$ are independently —H or a saturated or unsaturated hydrocarbyl or oxy-hydrocarbyl group containing from 1 to 4 carbons and the halo group is chloro or bromo.

16. The compound of claim 3, wherein:
R$^4$ is -oxo; R$^5$ is —CN; R$^6$ is —Br; and R$^7$ is —CH$_2$—C$_6$H$_4$-4-CH$_3$ (1441);
R$^4$ is —NH$_2$; R$^5$ is —CN; R$^6$ is —Br; and R$^7$ is —CH(CH$_3$)—C$_6$H$_5$ (1363);
R$^4$ is —NH$_2$; R$^5$ is —CN; R$^6$ is —Br; and R$^7$ is CH$_2$—C$_6$H$_4$-4-F (1353);
R$^4$ is —NH$_2$; R$^5$ is —CONH$_2$; R$^6$ is —Br; and R$^7$ is —CH$_2$—C$_6$H$_4$-4-Cl (1443);
R$^4$ is —NH$_2$; R$^5$ is —CN; R$^6$ is —Br; and R$^7$ is —CH$_2$—C$_6$H$_4$-4Cl (1355);
R$^4$ is —NH$_2$; R$^5$ is —CN; R$^6$ is —Br; and R$^7$ is —CH$_2$—C$_6$H$_4$-3-Cl (1461);
R$^4$ is —NH$_2$; R$^5$ is —CN; R$^6$ is —Br; and R$^7$ is —CH$_2$—C$_6$H$_3$-3,4-(Cl)$_2$ (1462);
R$^4$ is —NH$_2$; R$^5$ is —CN; R$^6$ is —Br; and R$^7$ is —CH$_2$—C$_6$H$_4$-4-Br (1373);
R$^4$ is —NH$_2$; R$^5$ is —CN; R$^6$ is —Br; and R$^7$ is —CH$_2$—C$_6$H$_4$-NO$_2$ (1374);
R$^4$ is —NH$_2$; R$^5$ is —CONH$_2$; R$^6$ is —Br; and R$^7$ is —CH$_2$—C$_6$H$_4$-4-CH$_3$ (1427);
R$^4$ is —NH—CH$_3$; R$^5$ is —CN; R$^6$ is —Br; and R$^7$ is —CH$_2$—CH$_2$—C$_6$H$_5$ (1463);
R$^4$ is —NH$_2$; R$^5$ is —CN; R$^6$ is —Br and R$^7$ is —CH$_2$—CH$_2$—C$_6$H$_5$ (1351);
R$^4$ is —NH$_2$; R$^5$ is —CONH$_2$; R$^6$ is —Br; and R$^7$ is —CH$_2$—CH$_2$—C$_6$H$_5$ (1409);
R$^4$ is —NH$_2$; R$^5$ is —CN; R$^6$ is —Br; and R$^7$ is —(CH$_2$)$_3$—C$_6$H$_5$ (1347); and
R$^4$ is —NH$_2$; R$^5$ is —CN; R$^6$ is —Br; and R$^7$ is —CH$_2$—CH═CH—C$_6$H$_5$ (1361).

17. The compound of claim 4, wherein R$^4$ is —NH$_2$; R$^5$ is —CN or —CONR$_1$R$_2$; R$^6$ is —H or a halo group.

18. The compound of claim 17, wherein R$_1$ and R$_2$ are independently —H or a saturated or unsaturated hydrocarbyl or oxy-hydrocarbyl group containing from 1 to 4 carbons and the halo group is chloro or bromo.

19. The compound of claim 4, wherein:
R$^4$ is —NH$_2$; R$^5$ is —CN; R$^6$ is —H; and R$^7$ is —CH$_2$—C$_6$H$_4$-4-F (1429);
R$^4$ is —NH$_2$; R$^5$ is —CN; R$^6$ is —H; and R$^7$ is —CH$_2$—C$_6$H$_4$-4-Cl (1444);
R$^4$ is —NH$_2$; R$^5$ is —CN; R$^6$ is —H; and R$^7$ is —CH$_2$—C$_6$H$_4$-4-NO$_2$ (1360);
R$^4$ is —NH$_2$; R$^5$ is —CN; R$^6$ is —H; and R$^7$ is —CH$_2$—C$_6$H$_4$-3-NO$_2$ (1362)
R$^4$ is —NH$_2$; R$^5$ is —CONH$_2$; R$^6$ is —H; and R$^7$ is —CH$_2$—C$_6$H$_4$-4-F (1419);
R$^4$ is —NH$_2$; R$^5$ is —CONH$_2$; R$^6$ is —H; and R$^7$ is —CH$_2$—C$_6$H$_4$-4-NO$_2$ (1412);
R$^4$ is —NH$_2$; R$^5$ is —CONH$_2$; R$^6$ is —H; and R$^7$ is —CH$_2$—C$_6$H$_4$-3-NO$_2$ (1421);
R$^4$ is —NH$_2$; R$^5$ is —CONH$_2$; R$^6$ is —Br; and R$^7$ is —CH$_2$—C$_6$H$_4$-4-Cl (1443);
R$^4$ is —NH$_2$; R$^5$ is —CN; R$^6$ is —Br; and R$^7$ is —CH$_2$—C$_6$H$_4$-4-Cl (1338);
R$^4$ is —NH$_2$; R$^5$ is —CN; R$^6$ is —Br; and R$^7$ is —CH$_2$—C$_6$H$_4$-3-Cl (1461);
R$^4$ is —NH$_2$; R$^5$ is —CN; R$^6$ is —Br; and R$^7$ is —CH$_2$—C$_6$H$_3$-3,4-(Cl)$_2$ (1462);
R$^4$ is —NH$_2$; R$^5$ is —CN; R$^6$ is —Br; and R$^7$ is —CH$_2$—C$_6$H$_4$-4-Br (1373);
R$^4$ is —NH$_2$; R$^5$ is —CN; R$^6$ is —Br; and R$^7$ is —CH$_2$—C$_6$H$_4$-4-NO$_2$ (1331);
R$^4$ is —NH$_2$; R$^5$ is —CN; R$^6$ is —Br; and R$^7$ is —CH$_2$—C$_6$H$_4$-3-NO$_2$ (1374);
R$^4$ is —NH$_2$; R$^5$ is —CN; R$^6$ is —NH$_2$; and R$^7$ is —CH$_2$—C$_6$H$_4$-4-F (1365);
R$^4$ is —NH$_2$; R$^5$ is —CN; R$^6$ is —NH$_2$; and R$^7$ is —CH$_2$—C$_6$H$_4$-4-Cl (1356);
R$^4$ is —NH$_2$; R$^5$ is —CN; R$^6$ is —NH$_2$; and R$^7$ is —CH$_2$—C$_6$H$_4$-4-Br (1389);
R$^4$ is —NH$_2$; R$^5$ is —CN; R$^6$ is —NH$_2$; and R$^7$ is —CH$_2$—C$_6$H$_4$-4-NO$_2$ (1348);
R$^4$ is —NH$_2$; R$^5$ is —CN; R$^6$ is —NH$_2$; and R$^7$ is —CH$_2$—C$_6$H$_4$-4-NH$_2$ (1352);
R$^4$ is —NH$_2$; R$^5$ is —CN; R$^6$ is —NH$_2$; and R$^7$ is —CH$_2$—C$_6$H$_4$-3-NO$_2$ (1425); and
R$^4$ is —NH$_2$; R$^5$ is —CN; R$^6$ is —NH$_2$; and R$^7$ is —CH$_2$—C$_6$H$_4$-3-NH$_2$ (1455).

20. The compound of claim 5, wherein R$^4$ is —NH$_2$; R$^5$ is —CN or —CONR$_1$R$_2$ or —CSNR$_1$R$_2$; and R$^6$ is —H or —NH$_2$, or a halo group.

21. The compound of claim 20, wherein R$_1$ and R$_2$ are independently —H or a saturated or unsaturated hydrocarbyl or oxy-hydrocarbyl group containing from 1 to 4 carbons and the halo group is chloro or bromo.

22. The compound of claim 5, wherein:
R$^4$ is —NH$_2$; R$^5$ is —CN; R$^6$ is —Br; and R$^7$ is —CH(CH$_3$)—C$_6$H$_5$ (1363);
R$^4$ is —NH$_2$; R$^5$ is —CN; R$^6$ is —NH$_2$; and R$^7$ is —CH(CH$_3$)—C$_6$H$_5$ (1451);
R$^4$ is —NH$_2$; R$^5$ is —CN; R$^6$ is —H; and R$^7$ is —CH$_2$—C$_6$H$_5$ (1368);
R$^4$ is —NH$_2$; R$^5$ is —CONH$_2$; R$^6$ is —H; and R$^7$ is —CH$_2$—CH$_2$—C$_6$H$_5$ (1396);
R$^4$ is —NH$_2$; R$^5$ is —CSNH$_2$; R$^6$ is —H; and R$^7$ is —CH$_2$—CH$_2$—C$_6$H$_5$ (1446);
R$^4$ is —NH$_2$; R$^5$ is —CN; R$^6$ is —NH$_2$; and R$^7$ is —CH$_2$—C$_6$H$_5$ (1369);
R$^4$ is —NH$_2$; R$^5$ is —CSNH$_2$; R$^6$ is —H; and R$^7$ is —CH$_2$—CH$_2$—CH$_2$—C$_6$H$_5$ (1413);
R$^4$ is —NH$_2$; R$^5$ is —CONH$_2$; R$^6$ is —H; and R$^7$ is —CH$_2$—CH$_2$—CH$_2$—C$_6$H$_5$ (1376);
R$^4$ is —NH$_2$; R$^5$ is —CN; R$^6$ is —H; and R$^7$ is —CH$_2$—CH$_2$—C$_6$H$_5$ (1362);
R$^4$ is —NH—CH$_3$; R$^5$ is —CN; R$^6$ is —Br; and R$^7$ is —CH$_2$—CH$_2$—C$_6$H$_5$ (1463);
R$^4$ is —NH$_2$; R$^5$ is —CN; R$^6$ is —Br; and R$^7$ is —CH$_2$—C$_6$H$_5$ (1351);
R$^4$ is —NH$_2$; R$^5$ is —CONH$_2$; R$^6$ is —Br; and R$^7$ is —CH$_2$—CH$_2$—C$_6$H$_5$ (1409);
R$^4$ is —NH$_2$; R$^5$ is —CN; R$^6$ is —Br; and R$^7$ is —(CH$_2$)$_3$—C$_6$H$_5$ (1347);
R$^4$ is —NH$_2$; R$^5$ is —CN; R$^6$ is —Br; and R$^7$ is —CH$_2$—CH═CH—C$_6$H$_5$ (1361);
R$^4$ is —NH$_2$; R$^5$ is —CN; R$^6$ is —NH$_2$; and R$^7$ is —CH$_2$—CH$_2$—C$_6$H$_5$ (1350);
R$^4$ is —NH$_2$; R$^5$ is —CN; R$^6$ is —H; and R$^7$ is —CH$_2$—CH═CH—C$_6$H$_5$ (1372); and
R$^4$ is —NH$_2$; R$^5$ is —CN; R$^6$ is —NH$_2$; and R$^7$ is —CH$_2$—CH═CH—C$_6$H$_5$ (1329).

23. A compound having the following structure: (1429)
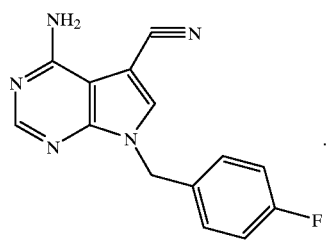
24. A compound having the following structure: (1444)
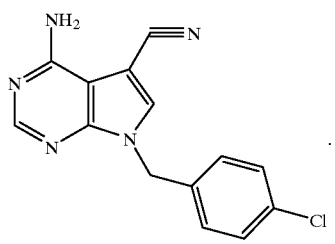
25. A compound having the following structure: (1360)
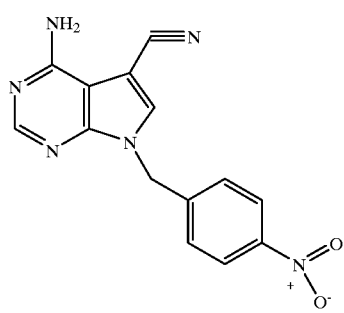
26. A compound having the following structure: (1353)
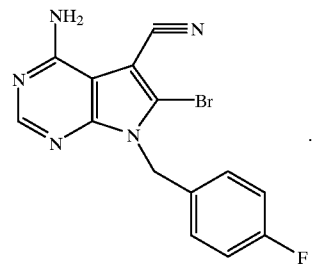
27. A compound having the following structure: (1365)
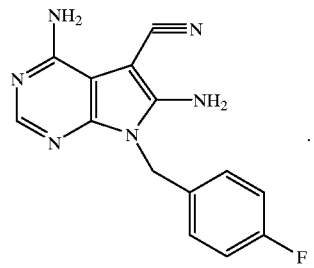
28. A compound having the following structure: (1356)
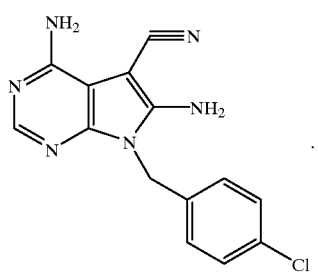
29. A compound having the following structure: (1389)
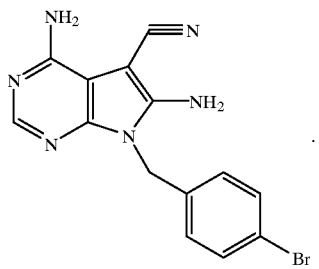
30. A compound having the following structure: (1348)
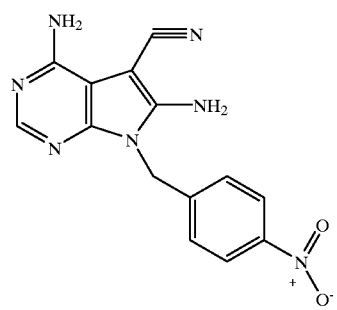

31. A compound having the following structure: (1446)

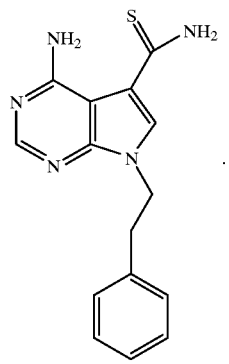

32. A compound having the following structure: (1351)

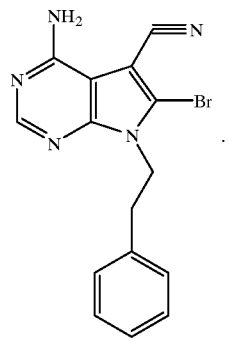

33. A compound having the following structure: (1368)

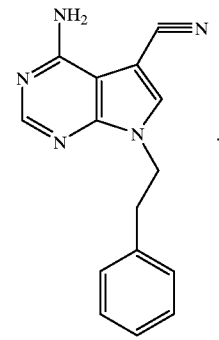

34. A compound having the following structure: (1369)

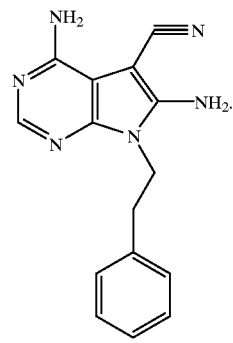

35. A compound having the following structure: (1413)

Note: actually structure (1413) is different image. Replacing with correct reference below.

36. The compound of claim 1, wherein $R^4$ is $NH_2$; $R^5$ is CN; is $R^6$ is $NHCH_3$ and $R^7$ is $(CH_2)_2\ C_6H_5$.

37. The compound of claim 1, wherein $R^4$ is $NH_2$; $R^5$ is CN; $R^6$ is $NH_2$ and $R^7$ is $(CH_2)_2\ C_6H_4$-4-F.

38. The compounds of claim 1, wherein $R^4$ is $NH_2$; $R^5$ is CN; $R^6$ is $N(CH_3)_2$ and $R^7$ is $CH_2CH_2C_6H_5$.

39. A pharmaceutical composition comprising a therapeutically effective amount of one or more compounds of claims 1, 2, 3, 4, or 5 and a pharmaceutically acceptable carrier.

40. A method for treating a viral infection caused by HCMV, HSV-1, HSV-2, varicella zoster virus, hepatitis B virus or hepatitis C virus in a subject comprising administering an effective amount of one or more compounds of the following structure:

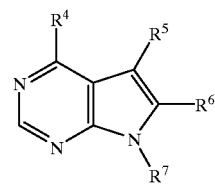

wherein:
- $R^4$ is —$NR_1R_2$;
- $R^5$ is —CN, or —$CSNR_1R_2$, or —$CONR_1R_2$;
- $R^6$ is —H, or halo, or —$NR_1R_2$;

wherein $R_1$ and $R_2$ are independently —H or a saturated or unsaturated hydrocarbyl or oxy-hydrocarbyl group containing from 1 to 4 carbons; and $R^7$ is of the formula $R_3$—Ar, wherein $R_3$ is a saturated or unsaturated hydrocarbyl or oxy-hydrocarbyl group containing from 1 to 4 carbons and Ar is an unsubstituted aryl or an aryl independently substituted with halo, nitro, amino, or a saturated or unsaturated hydrocarbyl or oxy-hydrocarbyl group containing from 1 to 4 carbons; and provided that when $R_1$, $R_2$ and $R^6$ are each H and Ar is $C_6H_5$ or a phenyl group substituted with only one saturated or unsaturated hydrocarbyl or oxy-hydrocarbyl group containing from 1 to 4 carbons, then $R_3$ is not —$CH_2$—; and pharmaceutically acceptable salts, esters and ethers thereof.

41. The method of claim 40, wherein the one or more compounds have the following structure:

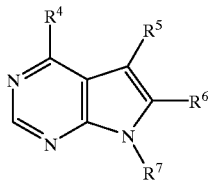

wherein:
- $R^4$ is —$NR_1R_2$;
- $R^5$ is —CN, or —$CSNR_1R_2$;
- $R^6$ is —H, or halo, or —$NR_1R_2$;

wherein $R_1$ and $R_2$ are independently —H or a saturated or unsaturated hydrocarbyl or oxy-hydrocarbyl group containing from 1 to 4 carbons; and $R^7$ is of the formula $R_3$—Ar, wherein $R_3$ is a saturated or unsaturated hydrocarbyl or oxy-hydrocarbyl group containing from 1 to 4 carbons and Ar is an unsubstituted aryl or an aryl independently substituted with halo, nitro, amino, or a saturated or unsaturated hydrocarbyl or oxy-hydrocarbyl group containing from 1 to 4 carbons; and pharmaceutically acceptable salts, esters and ethers thereof.

42. The method of claim 40, wherein the one or more compounds have the following structure:

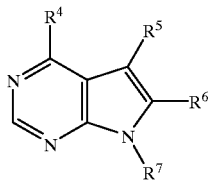

wherein:
- $R^4$ is —$NR_1R_2$;
- $R^5$ is —CN, or —$CSNR_1R_2$, or —$CONR_1R_2$;
- $R^6$ is halo;

wherein $R_1$ and $R_2$ are independently —H or a saturated or unsaturated hydrocarbyl or oxy-hydrocarbyl group containing from 1 to 4 carbons; and $R^7$ is of the formula $R_3$—Ar, wherein $R_3$ is a saturated or unsaturated hydrocarbyl or oxy-hydrocarbyl group containing from 1 to 4 carbons and Ar is an unsubstituted aryl or an aryl independently substituted with halo, nitro, amino, or a saturated or unsaturated hydrocarbyl or oxy-hydrocarbyl group containing from 1 to 4 carbons.

43. The method of claim 40, wherein the one or more compounds have the following structure:

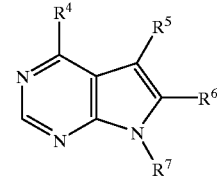

wherein:
- $R^4$ is —$NR_1R_2$;
- $R^5$ is —CN, or —$CSNR_1R_2$, or —$CONR_1R_2$;
- $R^6$ is halo;

wherein $R_1$ and $R_2$ are independently —H or a saturated or unsaturated hydrocarbyl or oxy-hydrocarbyl group containing from 1 to 4 carbons; and $R^7$ is of the formula $R_3$—Ar, wherein $R_3$ is a saturated or unsaturated hydrocarbyl or oxy-hydrocarbyl group containing from 1 to 4 carbons and Ar is an unsubstituted aryl or an aryl independently substituted with halo, nitro, amino, or a saturated or unsaturated hydrocarbyl or oxy-hydrocarbyl group containing from 1 to 4 carbons.

44. The method of claim 40, wherein the one or more compounds have the following structure:

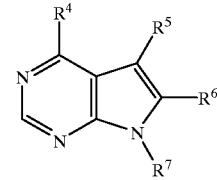

wherein:
- $R^4$ is—$NR_1R_2$;
- $R^5$ is —CN, or —$CSNR_1R_2$, or —$CONR_1R_2$;
- $R^6$ is —H, or halo, or —$NR_1R_2$;

wherein $R_1$ and $R_2$ are independently —H or a saturated or unsaturated hydrocarbyl or oxy-hydrocarbyl group containing from 1 to 4 carbons; and $R^7$ is of the formula $R_3$—Ar, wherein $R_3$ is a saturated or unsaturated hydrocarbyl or oxy-hydrocarbyl group containing from 1 to 4 carbons and Ar is an aryl independently substituted with halo, nitro, amino groups.

45. The method of claim 40, wherein the one or more compounds have the following structure.

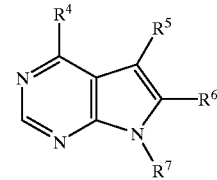

wherein:
- $R^4$ is —$NR_1R_2$;
- $R^5$ is —CN, or —$CSNR_1R_2$, or —$CONR_1R_2$;
- $R^6$ is —H, or halo, or —$NR_1R_2$;

wherein $R_1$ and $R_2$ are independently —H or a saturated or unsaturated hydrocarbyl or oxy-hydrocarbyl group containing from 1 to 4 carbons; and $R^7$ is of the formula $R_3$—Ar, wherein $R_3$ is a saturated or unsaturated hydrocarbyl or oxy-hydrocarbyl group containing from 1 to 4 carbons and Ar is an unsubstituted aryl or an aryl independently substituted with halo, nitro, amino, or a saturated or unsaturated hydrocarbyl or oxy-hydrocarbyl group containing from 1 to 4 carbons.

46. The method of claim 41, wherein $R^4$ is —$NH_2$; $R^5$ is —CN and $R^6$ is —H.

47. The method of claim 41, wherein $R^4$ is —$NH_2$; $R^5$ is —$CSNH_2$ and $R^6$ is —H.

48. The method of claim 41, wherein $R^4$ is —$NH_2$; $R^5$ is —CN and $R^6$ is —$NH_2$.

49. The method of claim 41, wherein $R^4$ is —$NH_2$; $R^5$ is —CN and $R^6$ is a halo group.

50. The method of claim 49, wherein the halo group is a bromo or chloro.

51. The method of claim 41, wherein:

$R^4$ is —$NH_2$; $R^5$ is —CN; $R^6$ is —H; and $R^7$ is —CH($CH_3$)—$C_6H_4$ (1414);

$R^4$ is —$NH_2$; $R^5$ is —CN; $R^6$ is —H; and $R^7$ is —$CH_2$—$C_6H_4$-4-F (1429);

$R^4$ is —$NH_2$; $R^5$ is —CN; $R^6$ is —H; and $R^7$ is —$CH_2$—$C_6H_4$-4-Cl (1444);

$R^4$ is —$NH_2$; $R^5$ is —CN; $R^6$ is —H; and $R^7$ is —$CH_2$—$C_6H_4$-4-$NO_2$ (1360);

$R^4$ is —$NH_2$; $R^5$ is —CN; $R^6$ is —H; and $R^7$ is —$CH_2$—$C_6H_4$-3-$NO_2$ (1362);

$R^4$ is —$NH_2$; $R^5$ is —CN; $R^6$ is —$NH_2$; and $R^7$ is —$(CH_2)_3$—$C_6H_5$ (1350);

$R^4$ is —$NH_2$; $R^5$ is —$CSNH_2$; $R^6$ is —H; and $R^7$ is —$CH_2$—$CH_2$—$C_6H_5$ (1446);

$R^4$ is —$NH_2$; $R^5$ is —$CSNH_2$; $R^6$ is —H; and $R^7$ is —$CH_2$—$CH_2$—$CH_2$—$C_6H_5$ (1413);

$R^4$ is —$NH_2$; $R^5$ is —CN; $R^6$ is —H; and $R^7$ is —$CH_2$—$CH_2$—$C_6H_5$ (1368);

$R^4$ is —$NH_2$; $R^5$ is —CN; $R^6$ is —$NH_2$; and $R^7$ is —CH($CH_3$)—$C_6H_5$ (1451);

$R^4$ is —$NH_2$; $R^5$ is —CN; $R^6$ is —$NH_2$; and $R^7$ is —$CH_2$—$C_6H_5$ (1369);

$R^4$ is —$NHCH_3$; $R^5$ is —CN; $R^6$ is —$NH_2$; and $R^7$ is —$CH_2$—$C_6H_4$-3-$NO_2$ (1425);

$R^4$ is —$NH_2$; $R^5$ is —CN; $R^6$ is —$NH_2$; and $R^7$ is —$CH_2$—$C_6H_4$-3-$NH_2$ (1455);

$R^4$ is —$NH_2$; $R^5$ is —CN; $R^6$ is —$NH_2$ and $R^7$ is —$CH_2$—$C_6H_4$-4-F (1365);

$R^4$ is —$NH_2$; $R^5$ is —CN; $R^6$ is —$NH_2$; and $R^7$ is —$CH_2$—$C_6H_4$-4-Cl (1356);

$R^4$ is —$NH_2$; $R^5$ is —CN; $R^6$ is —$NH_2$; and $R^7$ is —$CH_2$—$C_6H_4$-4-Br (1389);

$R^4$ is —$NH_2$; $R^5$ is —CN; $R^6$ is —$NH_2$; and $R^7$ is —$CH_2$—$C_6H_4$-4-$NO_2$ (1348);

$R^4$ is —$NH_2$; $R^5$ is —CN; $R^6$ is —$NH_2$; and $R^7$ is —$CH_2$—$C_6H_4$-4-$NH_2$ (1352);

$R^4$ is —$NH_2$; $R^5$ is —CN; $R^6$ is —H; and $R^7$ is —$CH_2$—CH=CH—$CH_2$—$C_6H_5$ (1372);

$R^4$ is —$NH_2$; $R^5$ is —CN; $R^6$ is —$NH_2$; and $R^7$ is —$CH_2$—CH=CH—$CH_2$—$C_6H_5$ (1329);

$R^4$ is -oxo; $R^5$ is —CN; $R^6$ is —Br; and $R^7$ is —$CH_2$—$C_6H_4$-4-$CH_3$ (1441);

$R^4$ is —$NH_2$; $R^5$ is —CN; $R^6$ is —Br; and $R^7$ is —CH($CH_3$)—$C_6H_5$ (1363);

$R^4$ is —$NH_2$; $R^5$ is —CN; $R^6$ is —Br; and $R^7$ is —$CH_2$—$C_6H_4$-4-F (1353);

$R^4$ is —$NH_2$; $R^5$ is —CN; $R^6$ is —Br; and $R^7$ is —$CH_2$—$C_6H_4$-4-Cl (1355)

$R^4$ is —$NH_2$; $R^5$ is —CN; $R^6$ is —Br; and $R^7$ is —$CH_2$—$C_6H_4$-3-Cl (1461);

$R^4$ is —$NH_2$; $R^5$ is —CN; $R^6$ is —Br; and $R^7$ is —$CH_2$—$C_6H_3$-3,4-$(Cl)_2$ (1462);

$R^4$ is —$NH_2$; $R^5$ is —CN; $R^6$ is —Br; and $R^7$ is —$CH_2$—$C_6H_4$-4-Br (1373);

$R^4$ is —$NH_2$; $R^5$ is —CN; $R^6$ is —Br; and $R^7$ is —$CH_2$—$C_6H_4$-4-$NO_2$ (1374);

$R^4$ is —NH—$CH_3$; $R^5$ is —CN; $R^6$ is —Br; and $R^7$ is —$CH_2$—$CH_2$—$C_6H_5$ (1463);

$R^4$ is —$NH_2$; $R^5$ is —CN; $R^6$ is —Br and $R^7$ is —$CH_2$—$CH_2$—$C_6H_5$ (1351);

$R^4$ is —$NH_2$; $R^5$ is —CN; $R^6$ is —Br; and $R^7$ is —$(CH_2)_3$—$C_6H_5$ (1347); and $R^4$ is —$NH_2$; $R^5$ is —CN; $R^6$ is —Br; and $R^7$ is —$CH_2$—CH=CH—$C_6H_5$ (1361).

* * * * *